US012697439B2

(12) United States Patent
Hamlin et al.

(10) Patent No.: US 12,697,439 B2
(45) Date of Patent: Aug. 4, 2026

(54) INJECTION DEVICE AND INJECTION SOLUTION TRANSFERRING SYSTEM

(71) Applicant: Novartis AG, Basel (CH)

(72) Inventors: Frederick William Hamlin, Boston, MA (US); Anthony Jonathan Bedford, Cambridge (GB); Duncan Aleck Bishop, Cambridgeshire (GB); Andrew Murray Gow, Wellington (NZ); David Stuart Harris, Cambridge (GB); Nicholas Lee Hawson, Brier, WA (US); Jean-Paul Kleeven, Wijchen (NL); Dominic Lloyd-Lucas, Cambridge (GB); David Mucientes, Basel (CH); Martin Joseph Murphy, Cambridge (GB); Stephen Paboojian, Basel (CH)

(73) Assignee: Novartis AG, Basel (CH)

( * ) Notice: Subject to any disclaimer, the term of this patent is extended or adjusted under 35 U.S.C. 154(b) by 1029 days.

(21) Appl. No.: 17/784,373

(22) PCT Filed: Dec. 11, 2020

(86) PCT No.: PCT/US2020/064698
§ 371 (c)(1),
(2) Date: Jun. 10, 2022

(87) PCT Pub. No.: WO2021/119544
PCT Pub. Date: Jun. 17, 2021

(65) Prior Publication Data
US 2023/0052782 A1     Feb. 16, 2023

Related U.S. Application Data

(60) Provisional application No. 62/947,462, filed on Dec. 12, 2019.

(51) Int. Cl.
*A61M 5/315* (2006.01)
*A61M 5/31* (2006.01)

(52) U.S. Cl.
CPC ...... *A61M 5/31501* (2013.01); *A61M 5/3137* (2013.01); *A61M 5/31583* (2013.01);
(Continued)

(58) Field of Classification Search
CPC ........... A61M 2005/3139; A61M 2005/31508; A61M 2210/0612; A61M 5/3137;
(Continued)

(56) References Cited

U.S. PATENT DOCUMENTS

| 3,608,550 A | 9/1971 | Stawski |
| 4,475,905 A | 10/1984 | Himmelstrup |
| | (Continued) | |

FOREIGN PATENT DOCUMENTS

| AT | 178217 T | 4/1999 |
| AT | 193215 T | 6/2000 |
| | (Continued) | |

OTHER PUBLICATIONS

Non-Final Office Action received for U.S. Appl. No. 16/620,334, mailed on Jul. 11, 2022, 12 pages.
(Continued)

*Primary Examiner* — Shefali D Patel
(74) *Attorney, Agent, or Firm* — YHE Law LLP

(57) ABSTRACT

The present disclosure relates to an injection device, in particular a micro dose injection device such as, for example, an ophthalmic injection device. An example injection device comprises a rotatable plunger; a solution receptacle having a first end configured to slidably receive the rotatable plunger and a second end configured to dispense solution contained in the solution receptacle; a first stop member configured to prevent the rotatable plunger from
(Continued)

being slidably displaced to a second position while the rotatable plunger is at a first position and in a first orientation; and a second stop member configured to prevent the rotatable plunger from rotating in a first direction about a first axis while the rotatable plunger is at the first position and in the first orientation, wherein slidably displacing the rotatable plunger from the first position to the second position dispenses a quantity of the solution contained in the solution receptacle.

26 Claims, 43 Drawing Sheets

(52) U.S. Cl.
CPC . *A61M 5/31595* (2013.01); *A61M 2005/3114* (2013.01); *A61M 2005/3139* (2013.01); *A61M 2210/0612* (2013.01)

(58) Field of Classification Search
CPC .............. A61M 5/315; A61M 5/31501; A61M 5/31565; A61M 5/31576; A61M 5/31583; A61M 5/3159; A61M 5/31593; A61M 5/31595
See application file for complete search history.

(56) References Cited

U.S. PATENT DOCUMENTS

| | | | |
|---|---|---|---|
| 5,807,374 A | 9/1998 | Caizza et al. | |
| 5,820,602 A | 10/1998 | Kovelman et al. | |
| 5,928,215 A | 7/1999 | Caizza et al. | |
| 6,149,623 A | 11/2000 | Reynolds | |
| 6,174,304 B1 | 1/2001 | Weston | |
| 6,638,244 B1 | 10/2003 | Reynolds | |
| 6,663,602 B2 | 12/2003 | Møller | |
| 6,681,810 B2 | 1/2004 | Weston | |
| 6,685,693 B1 | 2/2004 | Casso | |
| 7,241,278 B2 | 7/2007 | Moller | |
| 7,470,258 B2 | 12/2008 | Barker et al. | |
| 7,736,343 B2 | 6/2010 | Marshall et al. | |
| 7,811,263 B2 | 10/2010 | Burren et al. | |
| 7,867,202 B2 | 1/2011 | Moser et al. | |
| 7,896,850 B2 | 3/2011 | Kronestedt et al. | |
| 8,202,256 B2 | 6/2012 | Moller | |
| 8,206,361 B2 | 6/2012 | Moller | |
| 8,267,899 B2 | 9/2012 | Moller | |
| 8,333,739 B2 | 12/2012 | Moller | |
| 8,409,138 B2 | 4/2013 | James et al. | |
| 8,617,109 B2 | 12/2013 | Kronestedt et al. | |
| 8,834,954 B2 | 9/2014 | Felts et al. | |
| 8,869,635 B2 | 10/2014 | Daniel et al. | |
| 8,973,621 B2 | 3/2015 | Matusch | |
| 9,011,386 B2 | 4/2015 | Kronestedt et al. | |
| 9,022,991 B1 | 5/2015 | Moeller | |
| 9,272,095 B2 | 3/2016 | Felts et al. | |
| 9,345,846 B1 | 5/2016 | Rabinne et al. | |
| 9,381,687 B2 * | 7/2016 | Felts .................. | A61M 5/3134 |
| 9,458,536 B2 | 10/2016 | Felts et al. | |
| 9,475,225 B2 | 10/2016 | Giraud et al. | |
| 9,545,360 B2 | 1/2017 | Felts et al. | |
| 9,554,968 B2 | 1/2017 | Weikart et al. | |
| 9,572,526 B2 | 2/2017 | Felts et al. | |
| 9,662,450 B2 | 5/2017 | Jones et al. | |
| 9,664,626 B2 | 5/2017 | Fisk | |
| 9,764,093 B2 | 9/2017 | Weikart et al. | |
| 9,855,577 B1 | 1/2018 | Belfance et al. | |
| 9,863,042 B2 | 1/2018 | Jones et al. | |
| 9,878,101 B2 | 1/2018 | Felts et al. | |
| 9,903,782 B2 | 2/2018 | Fisk et al. | |
| 9,937,099 B2 | 4/2018 | Weikart et al. | |
| 9,952,147 B2 | 4/2018 | Fisk et al. | |
| 9,981,794 B2 | 5/2018 | Sagona et al. | |

| | | | |
|---|---|---|---|
| 10,016,338 B2 | 7/2018 | Weikart et al. | |
| 10,059,047 B2 | 8/2018 | Giraud et al. | |
| 10,189,603 B2 | 1/2019 | Felts et al. | |
| 10,201,660 B2 | 2/2019 | Weikart et al. | |
| 10,258,718 B2 | 4/2019 | Belfance et al. | |
| 10,327,986 B2 | 6/2019 | Gross et al. | |
| 10,363,370 B2 | 7/2019 | Weikart et al. | |
| 10,390,744 B2 | 8/2019 | Felts et al. | |
| 11,554,215 B2 | 1/2023 | Hawson et al. | |
| 2001/0051793 A1 | 12/2001 | Weston | |
| 2002/0052578 A1 | 5/2002 | Moller | |
| 2002/0177819 A1 | 11/2002 | Barker et al. | |
| 2004/0024354 A1 | 2/2004 | Reynolds | |
| 2004/0059299 A1 | 3/2004 | Moller | |
| 2005/0090782 A1 | 4/2005 | Marshall et al. | |
| 2005/0209570 A1 | 9/2005 | Moller | |
| 2006/0276753 A1 | 12/2006 | Kronestedt et al. | |
| 2006/0276754 A1 | 12/2006 | Kronestedt et al. | |
| 2007/0016142 A1 | 1/2007 | Burren et al. | |
| 2007/0021718 A1 | 1/2007 | Burren et al. | |
| 2007/0244445 A1 | 10/2007 | Moller | |
| 2008/0065026 A1 | 3/2008 | Moller | |
| 2008/0071227 A1 | 3/2008 | Moser et al. | |
| 2008/0077094 A1 | 3/2008 | Burren et al. | |
| 2008/0183138 A1 | 7/2008 | Moser et al. | |
| 2008/0281275 A1 | 11/2008 | Moller | |
| 2009/0308386 A1 | 12/2009 | Kronestedt et al. | |
| 2010/0049125 A1 | 2/2010 | James et al. | |
| 2010/0186739 A1 | 7/2010 | Kronestedt et al. | |
| 2011/0214777 A1 | 9/2011 | Matusch | |
| 2012/0152039 A1 | 6/2012 | Daniel et al. | |
| 2012/0226240 A1 | 9/2012 | Bedford et al. | |
| 2013/0079728 A1 | 3/2013 | Moeller | |
| 2013/0216466 A1 * | 8/2013 | Traunspurger ........ | C01B 33/037 134/20 |
| 2013/0289518 A1 | 10/2013 | Butler et al. | |
| 2014/0012227 A1 * | 1/2014 | Sigg ..................... | A61M 5/315 604/218 |
| 2014/0107625 A1 * | 4/2014 | Hanlon ............... | A61F 9/00736 604/533 |
| 2014/0150925 A1 | 6/2014 | Sjogren et al. | |
| 2014/0316334 A1 | 10/2014 | Holmqvist et al. | |
| 2015/0100028 A1 | 4/2015 | Moeller | |
| 2015/0157801 A1 | 6/2015 | Tran et al. | |
| 2015/0297453 A1 | 10/2015 | Kim et al. | |
| 2015/0297455 A1 | 10/2015 | Sanders et al. | |
| 2015/0297881 A1 | 10/2015 | Sanders et al. | |
| 2016/0001004 A1 | 1/2016 | Fourt et al. | |
| 2016/0151578 A1 | 6/2016 | Oakley et al. | |
| 2017/0290987 A1 * | 10/2017 | Mandaroux ....... | A61M 5/31513 |
| 2018/0296525 A1 * | 10/2018 | Roizman ................ | A61K 31/40 |

FOREIGN PATENT DOCUMENTS

| | | | |
|---|---|---|---|
| AT | 217181 T | 5/2002 | |
| AT | 303831 T | 9/2005 | |
| AT | 401921 7 | 8/2008 | |
| AU | 725917 B2 | 10/2000 | |
| AU | 726244 B2 | 11/2000 | |
| AU | 2003287059 A1 | 5/2004 | |
| AU | 2003287059 A8 | 5/2004 | |
| AU | 2003287060 A1 | 5/2004 | |
| AU | 2003287060 A8 | 5/2004 | |
| AU | 2006218064 A1 | 8/2006 | |
| AU | 2006251769 A1 | 11/2006 | |
| AU | 2008226638 A1 | 9/2008 | |
| AU | 2006218064 B2 | 5/2009 | |
| AU | 2006251769 B2 | 7/2009 | |
| AU | 2009217376 A1 | 10/2009 | |
| AU | 2009217376 B2 | 1/2013 | |
| AU | 2008226638 B2 | 3/2013 | |
| AU | 2011315626 A1 | 4/2013 | |
| AU | 2011315626 B2 | 1/2015 | |
| AU | 2014241449 A1 | 8/2015 | |
| AU | 2014328035 A1 | 4/2016 | |
| BE | 726863 A | 7/1969 | |
| BR | PI9510212-4 A | 11/1997 | |
| BR | P19802604-6 A | 11/1999 | |
| BR | PI0208064-8 A | 10/2006 | |

(56)  References Cited

FOREIGN PATENT DOCUMENTS

| | | | |
|---|---|---|---|
| BR | PI0808709-1 | A2 | 9/2014 |
| CA | 2231481 | A1 | 3/1997 |
| CA | 2207991 | C | 8/2001 |
| CA | 2242915 | C | 8/2001 |
| CA | 2412229 | A1 | 12/2001 |
| CA | 2243021 | C | 3/2002 |
| CA | 2440888 | A1 | 9/2002 |
| CA | 2231481 | C | 1/2008 |
| CA | 2680335 | A1 | 9/2008 |
| CA | 2412229 | C | 8/2010 |
| CA | 2678198 | A1 | 3/2011 |
| CA | 2813277 | A1 | 4/2012 |
| CA | 2680335 | C | 1/2014 |
| CA | 2899558 | A1 | 10/2014 |
| CA | 2929376 | A1 | 5/2015 |
| CH | 492215 | A | 6/1970 |
| CN | 1175217 | A | 3/1998 |
| CN | 1197398 | A | 10/1998 |
| CN | 1441684 | A | 9/2003 |
| CN | 1509192 | A | 6/2004 |
| CN | 1188181 | C | 2/2005 |
| CN | 101124005 | A | 2/2008 |
| CN | 101184521 | A | 5/2008 |
| CN | 101641125 | A | 2/2010 |
| CN | 101124005 | B | 12/2010 |
| CN | 202113444 | U | 1/2012 |
| CN | 101184521 | B | 2/2012 |
| CN | 102946930 | A | 2/2013 |
| CN | 101641125 | B | 6/2013 |
| CN | 103260675 | A | 8/2013 |
| CN | 105025958 | A | 11/2015 |
| CN | 103260675 | B | 1/2016 |
| CN | 105377329 | A | 3/2016 |
| DE | 1901633 | A1 | 9/1969 |
| DE | 2021253 | A1 | 11/1970 |
| DE | 8509572 | U1 | 8/1985 |
| DE | 69508792 | T2 | 8/1999 |
| DE | 69608567 | T2 | 2/2001 |
| DE | 69712499 | T2 | 11/2002 |
| DE | 69808205 | T2 | 5/2003 |
| DE | 60113256 | T2 | 6/2006 |
| DE | 102005008065 | A1 | 8/2006 |
| DE | 102005023823 | A1 | 11/2006 |
| DE | 102005023854 | A1 | 11/2006 |
| DE | 102005032705 | A1 | 11/2006 |
| DE | 102005044096 | A1 | 11/2006 |
| DE | 102005032705 | B4 | 1/2009 |
| DE | 102005063497 | B4 | 9/2009 |
| DE | 202005021773 | U1 | 1/2010 |
| DE | 102010010699 | A1 | 9/2011 |
| DK | 124660 | B | 11/1972 |
| DK | 0799063 | T3 | 10/1999 |
| DK | 0850079 | T3 | 11/2000 |
| DK | 928182 | T3 | 8/2002 |
| DK | 1294418 | T3 | 1/2006 |
| DK | 1728529 | T3 | 11/2008 |
| DK | 1855742 | T3 | 4/2009 |
| DK | 1888149 | T3 | 6/2009 |
| DK | 1855740 | T3 | 7/2009 |
| DK | 1885414 | T3 | 2/2013 |
| DK | 2065065 | T3 | 6/2013 |
| EA | 201591482 | A1 | 1/2016 |
| EP | 0799063 | A1 | 10/1997 |
| EP | 0850079 | A1 | 7/1998 |
| EP | 0896826 | A1 | 2/1999 |
| EP | 0928182 | A1 | 7/1999 |
| EP | 0850079 | B1 | 5/2000 |
| EP | 0928182 | B1 | 5/2002 |
| EP | 0896826 | B1 | 9/2002 |
| EP | 1294418 | A1 | 3/2003 |
| EP | 1372756 | A2 | 1/2004 |
| EP | 1463550 | A2 | 10/2004 |
| EP | 1568389 | A1 | 8/2005 |
| EP | 1294418 | B1 | 9/2005 |
| EP | 1690561 | A2 | 8/2006 |
| EP | 1690561 | A3 | 12/2006 |
| EP | 1728529 | A1 | 12/2006 |
| EP | 1855740 | A1 | 11/2007 |
| EP | 1855742 | A1 | 11/2007 |
| EP | 1885414 | A1 | 2/2008 |
| EP | 1885415 | A1 | 2/2008 |
| EP | 1888149 | A1 | 2/2008 |
| EP | 1372756 | A4 | 5/2008 |
| EP | 1728529 | B1 | 7/2008 |
| EP | 1855742 | B1 | 12/2008 |
| EP | 1888149 | B1 | 2/2009 |
| EP | 1855740 | B1 | 3/2009 |
| EP | 2065065 | A2 | 6/2009 |
| EP | 2134391 | A2 | 12/2009 |
| EP | 2065065 | A3 | 6/2010 |
| EP | 2364742 | A2 | 9/2011 |
| EP | 2364743 | A1 | 9/2011 |
| EP | 1885415 | A4 | 2/2012 |
| EP | 1885414 | A4 | 4/2012 |
| EP | 2475454 | A1 | 7/2012 |
| EP | 2484395 | A2 | 8/2012 |
| EP | 1885414 | B1 | 11/2012 |
| EP | 2364742 | A3 | 11/2012 |
| EP | 2526987 | A2 | 11/2012 |
| EP | 1885415 | B1 | 5/2013 |
| EP | 2627377 | A1 | 8/2013 |
| EP | 2475454 | B1 | 11/2015 |
| EP | 2968766 | A1 | 1/2016 |
| EP | 3021900 | A1 | 5/2016 |
| EP | 3035983 | A2 | 6/2016 |
| ES | 2129881 | T3 | 6/1999 |
| ES | 2149499 | T3 | 11/2000 |
| ES | 2176661 | T3 | 12/2002 |
| ES | 2185115 | T3 | 4/2003 |
| ES | 2249442 | T3 | 4/2006 |
| ES | 2314568 | T3 | 3/2009 |
| ES | 2423199 | T3 | 9/2013 |
| FR | 2000286 | A1 | 9/1969 |
| FR | 2046102 | A5 | 3/1971 |
| GB | 1261751 | A | 1/1972 |
| GB | 1267419 | A | 3/1972 |
| JP | 10-510740 | A | 10/1998 |
| JP | 11-114064 | A | 4/1999 |
| JP | 11-510087 | A | 9/1999 |
| JP | 11-512303 | A | 10/1999 |
| JP | 2001-505072 | A | 4/2001 |
| JP | 3450011 | B2 | 9/2003 |
| JP | 2004-49726 | A | 2/2004 |
| JP | 2004-503303 | A | 2/2004 |
| JP | 2005-508656 | A | 4/2005 |
| JP | 2005-514120 | A | 5/2005 |
| JP | 3835817 | B2 | 10/2006 |
| JP | 2006-326309 | A | 12/2006 |
| JP | 2006-329423 | A | 12/2006 |
| JP | 2008-529688 | A | 8/2008 |
| JP | 2008-532581 | A | 8/2008 |
| JP | 2008-541803 | A | 11/2008 |
| JP | 2008-541931 | A | 11/2008 |
| JP | 2008-541932 | A | 11/2008 |
| JP | 4187790 | B2 | 11/2008 |
| JP | 4357611 | B2 | 11/2009 |
| JP | 2010-520786 | A | 6/2010 |
| JP | 4550424 | B2 | 7/2010 |
| JP | 4519803 | B2 | 8/2010 |
| JP | 4575327 | B2 | 11/2010 |
| JP | 4755247 | B2 | 6/2011 |
| JP | 2011-156369 | A | 8/2011 |
| JP | 2011-183163 | A | 9/2011 |
| JP | 4837874 | B2 | 10/2011 |
| JP | 5026411 | B2 | 6/2012 |
| JP | 5026412 | B2 | 6/2012 |
| JP | 5118222 | B2 | 10/2012 |
| JP | 2013-511309 | A | 4/2013 |
| JP | 5362591 | B2 | 9/2013 |
| JP | 2013-539697 | A | 10/2013 |
| JP | 2014-87678 | A | 5/2014 |
| JP | 2015-66058 | A | 4/2015 |
| JP | 5881958 | B2 | 2/2016 |
| JP | 5897016 | B2 | 3/2016 |

(56) References Cited

FOREIGN PATENT DOCUMENTS

| | | | |
|---|---|---|---|
| JP | 2016-517301 | A | 6/2016 |
| JP | 2018-519936 | A | 7/2018 |
| KR | 2003-0020299 | A | 3/2003 |
| KR | 10-0721549 | B1 | 5/2007 |
| KR | 10-2009-0109581 | A | 10/2009 |
| KR | 10-1160735 | B1 | 7/2012 |
| KR | 10-2015-0119092 | A | 10/2015 |
| MX | 9704576 | A | 7/1998 |
| MX | PA03007940 | A | 10/2004 |
| MX | 2009009494 | A | 9/2009 |
| NL | 6800629 | A | 7/1969 |
| NO | 312175 | B1 | 4/2002 |
| NO | 20025994 | L | 2/2003 |
| NO | 334665 | B1 | 5/2014 |
| NZ | 330879 | A | 1/2000 |
| RU | 2155609 | C2 | 9/2000 |
| RU | 2270698 | C2 | 2/2006 |
| TW | 503117 | B | 9/2002 |
| TW | 201215424 | A | 4/2012 |
| WO | 1996/19252 | A1 | 6/1996 |
| WO | 1997/01362 | A2 | 1/1997 |
| WO | 1997/09080 | A1 | 3/1997 |
| WO | 1997/25015 | A1 | 7/1997 |
| WO | 1997/46202 | A1 | 12/1997 |
| WO | 2001/95959 | A1 | 12/2001 |
| WO | 2002/072173 | A2 | 9/2002 |
| WO | 2003/057285 | A2 | 7/2003 |
| WO | 2002/072173 | A3 | 10/2003 |
| WO | 2003/057285 | A3 | 12/2003 |
| WO | 2004/032996 | A2 | 4/2004 |
| WO | 2004/032997 | A2 | 4/2004 |
| WO | 2005/121176 | A1 | 12/2005 |
| WO | 2005/123162 | A1 | 12/2005 |
| WO | 2006/089437 | A1 | 8/2006 |
| WO | 2006/089734 | A1 | 8/2006 |
| WO | 2006/125329 | A1 | 11/2006 |
| WO | 2006/130098 | A1 | 12/2006 |
| WO | 2006/130100 | A1 | 12/2006 |
| WO | 2008/112472 | A2 | 9/2008 |
| WO | 2010/146358 | A2 | 12/2010 |
| WO | 2011/029184 | A1 | 3/2011 |
| WO | 2011/073174 | A1 | 6/2011 |
| WO | 2011/073176 | A1 | 6/2011 |
| WO | 2010/146358 | A3 | 8/2011 |
| WO | 2012/049141 | A1 | 4/2012 |
| WO | 2014/159017 | A1 | 10/2014 |
| WO | WO-2014162551 | A1 * | 10/2014 ........ A61M 5/31511 |
| WO | 2015/007808 | A1 | 1/2015 |
| WO | 2015/047758 | A2 | 4/2015 |
| WO | 2015/067548 | A1 | 5/2015 |
| WO | 2015/047758 | A3 | 7/2015 |
| WO | 2015/164377 | A1 | 10/2015 |
| WO | 2015/164413 | A1 | 10/2015 |
| WO | 2015/164416 | A1 | 10/2015 |
| WO | 2017/011599 | A1 | 1/2017 |
| WO | WO-2018160849 | A1 * | 9/2018 ........... A61K 48/005 |
| WO | 2018/224644 | A1 | 12/2018 |
| ZA | 2002/9998 | B | 12/2003 |

OTHER PUBLICATIONS

Notice of Allowance received for U.S. Appl. No. 16/620,334, mailed on Nov. 25, 2022, 7 pages.

Peer at Tamu, "A syringe with a Needle Fills Another Syring", See video at 1.40 min, available at: https://www.youtube.com/watch?v=Ch1murqNz7M, Apr. 9, 2019, 3 pages.

International Search Report and Written Opinion dated Mar. 29, 2021, for International Application No. PCT/US2020/064698, 14 pages.

Japanese Notification of Reasons for Refusal dated Oct. 31, 2023, for Application No. 2022-535507, 5 pages.

* cited by examiner

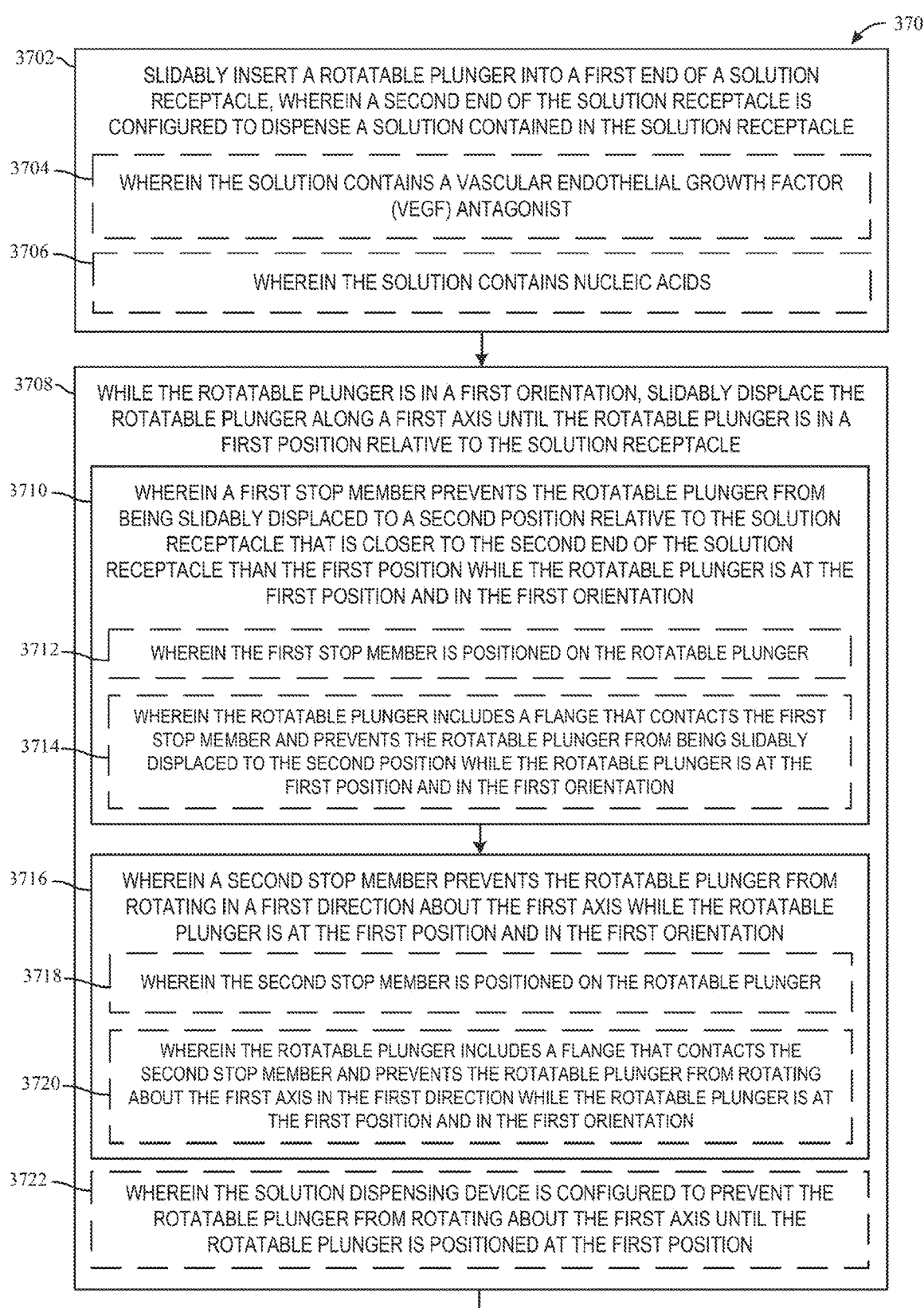

3700

3702 — SLIDABLY INSERT A ROTATABLE PLUNGER INTO A FIRST END OF A SOLUTION RECEPTACLE, WHEREIN A SECOND END OF THE SOLUTION RECEPTACLE IS CONFIGURED TO DISPENSE A SOLUTION CONTAINED IN THE SOLUTION RECEPTACLE

3704 — WHEREIN THE SOLUTION CONTAINS A VASCULAR ENDOTHELIAL GROWTH FACTOR (VEGF) ANTAGONIST

3706 — WHEREIN THE SOLUTION CONTAINS NUCLEIC ACIDS

3708 — WHILE THE ROTATABLE PLUNGER IS IN A FIRST ORIENTATION, SLIDABLY DISPLACE THE ROTATABLE PLUNGER ALONG A FIRST AXIS UNTIL THE ROTATABLE PLUNGER IS IN A FIRST POSITION RELATIVE TO THE SOLUTION RECEPTACLE

3710 — WHEREIN A FIRST STOP MEMBER PREVENTS THE ROTATABLE PLUNGER FROM BEING SLIDABLY DISPLACED TO A SECOND POSITION RELATIVE TO THE SOLUTION RECEPTACLE THAT IS CLOSER TO THE SECOND END OF THE SOLUTION RECEPTACLE THAN THE FIRST POSITION WHILE THE ROTATABLE PLUNGER IS AT THE FIRST POSITION AND IN THE FIRST ORIENTATION

3712 — WHEREIN THE FIRST STOP MEMBER IS POSITIONED ON THE ROTATABLE PLUNGER

3714 — WHEREIN THE ROTATABLE PLUNGER INCLUDES A FLANGE THAT CONTACTS THE FIRST STOP MEMBER AND PREVENTS THE ROTATABLE PLUNGER FROM BEING SLIDABLY DISPLACED TO THE SECOND POSITION WHILE THE ROTATABLE PLUNGER IS AT THE FIRST POSITION AND IN THE FIRST ORIENTATION

3716 — WHEREIN A SECOND STOP MEMBER PREVENTS THE ROTATABLE PLUNGER FROM ROTATING IN A FIRST DIRECTION ABOUT THE FIRST AXIS WHILE THE ROTATABLE PLUNGER IS AT THE FIRST POSITION AND IN THE FIRST ORIENTATION

3718 — WHEREIN THE SECOND STOP MEMBER IS POSITIONED ON THE ROTATABLE PLUNGER

3720 — WHEREIN THE ROTATABLE PLUNGER INCLUDES A FLANGE THAT CONTACTS THE SECOND STOP MEMBER AND PREVENTS THE ROTATABLE PLUNGER FROM ROTATING ABOUT THE FIRST AXIS IN THE FIRST DIRECTION WHILE THE ROTATABLE PLUNGER IS AT THE FIRST POSITION AND IN THE FIRST ORIENTATION

3722 — WHEREIN THE SOLUTION DISPENSING DEVICE IS CONFIGURED TO PREVENT THE ROTATABLE PLUNGER FROM ROTATING ABOUT THE FIRST AXIS UNTIL THE ROTATABLE PLUNGER IS POSITIONED AT THE FIRST POSITION (A)

*FIG. 37a*

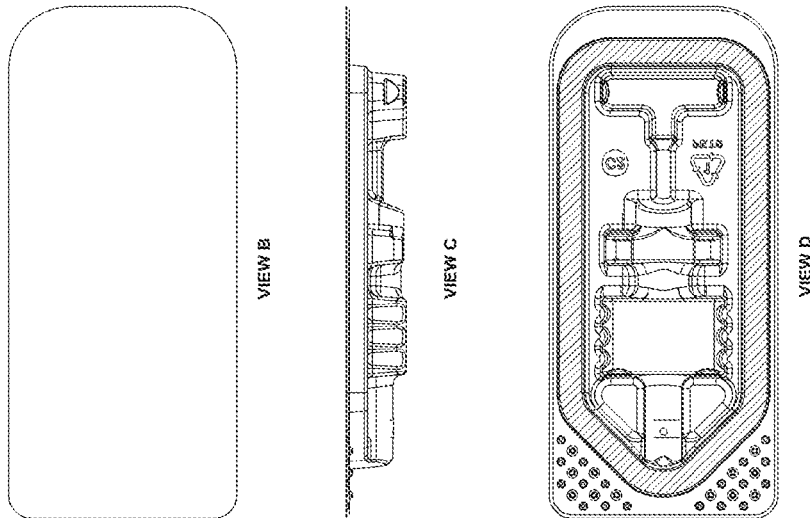
VIEW B
VIEW C
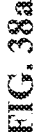
VIEW D
FIG. 38a
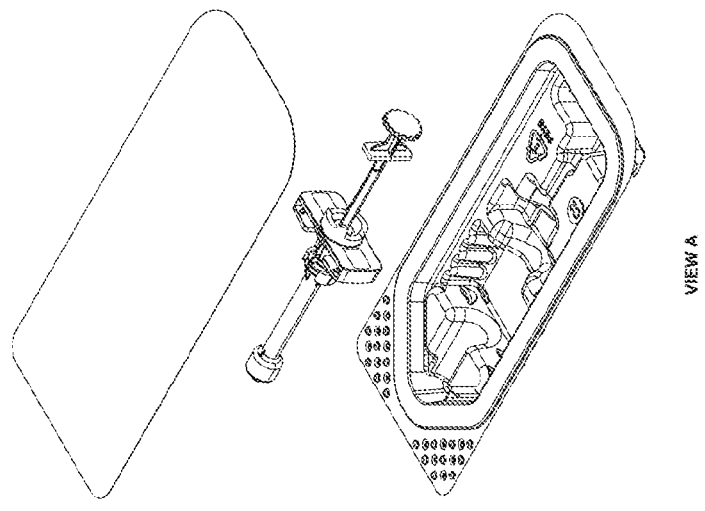
VIEW A

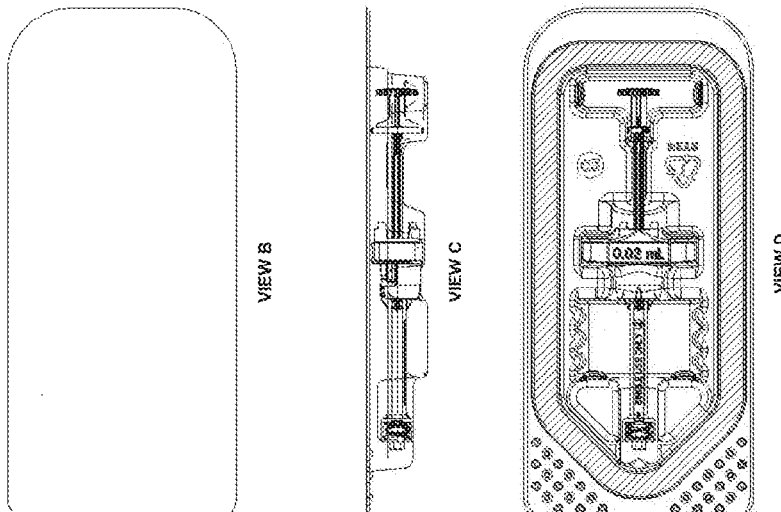
VIEW B
VIEW C
VIEW D
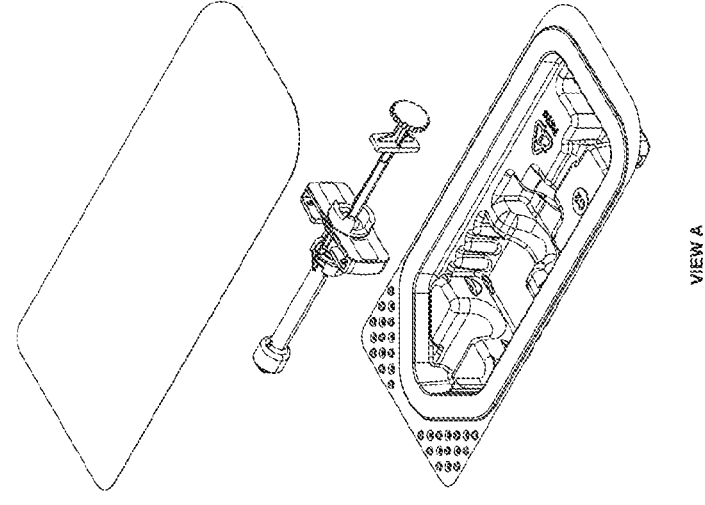
VIEW A
FIG. 38b

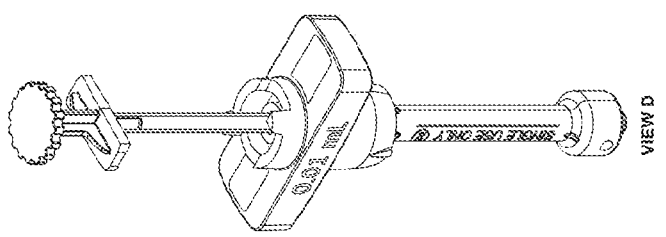
VIEW D
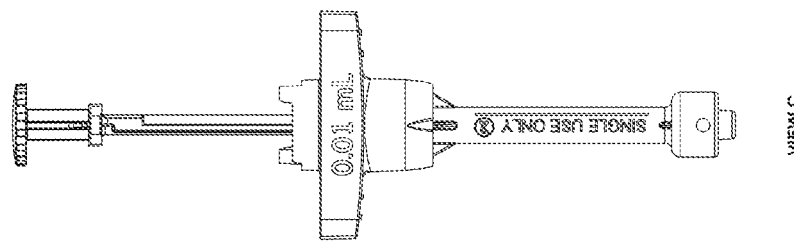
VIEW C
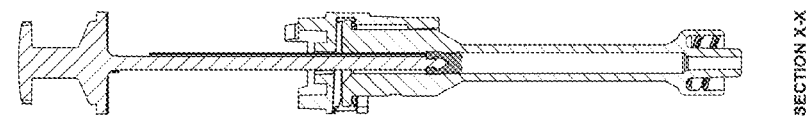
SECTION X-X
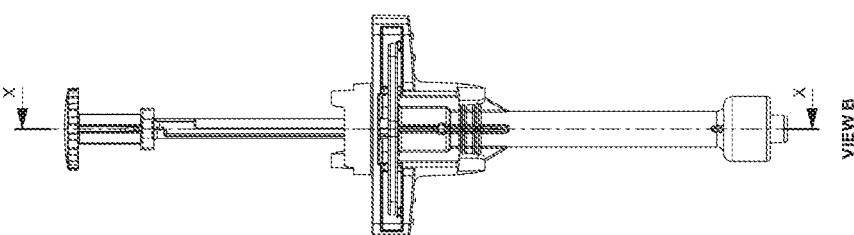
VIEW B
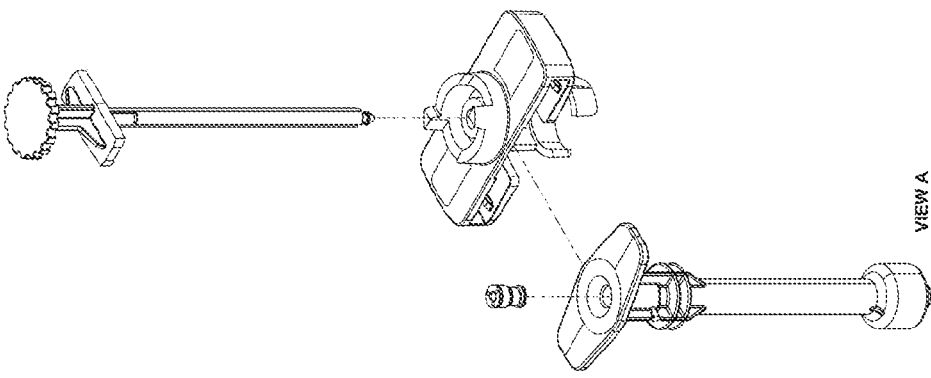
VIEW A
FIG. 38c

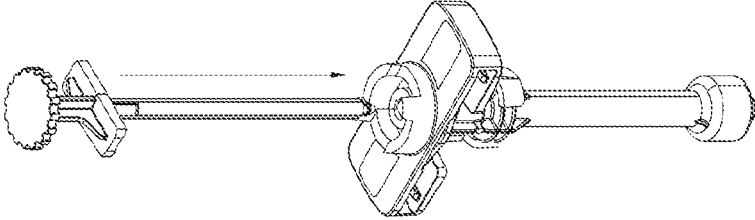
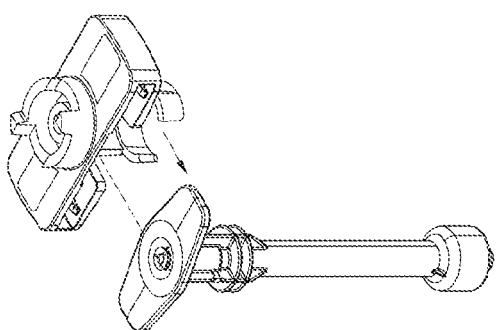
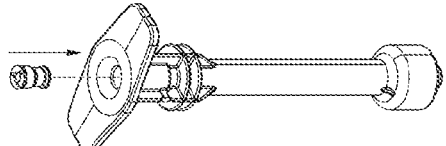
FIG. 38d

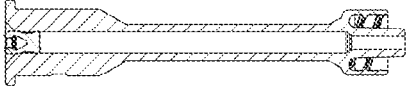
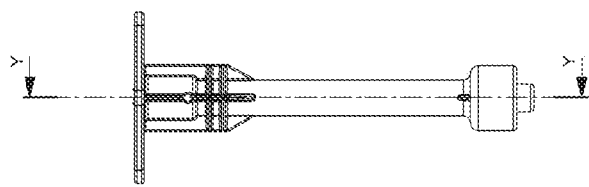
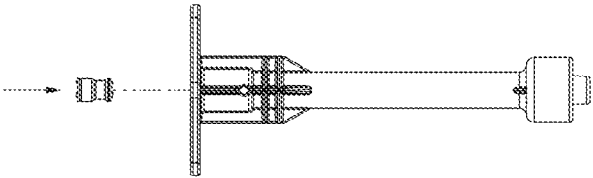
FIG. 38e

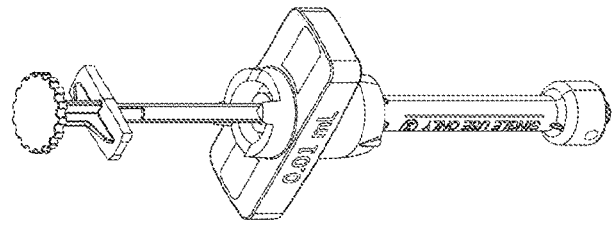
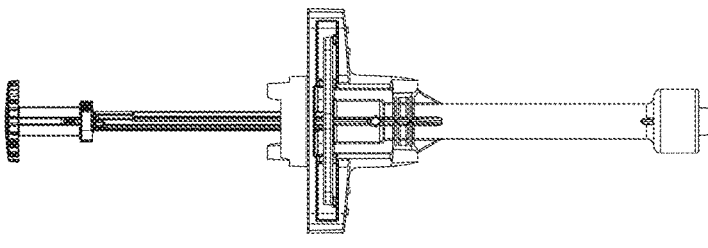
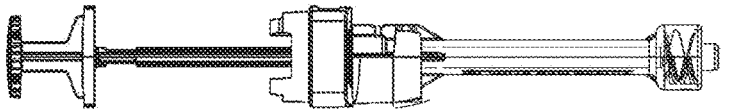
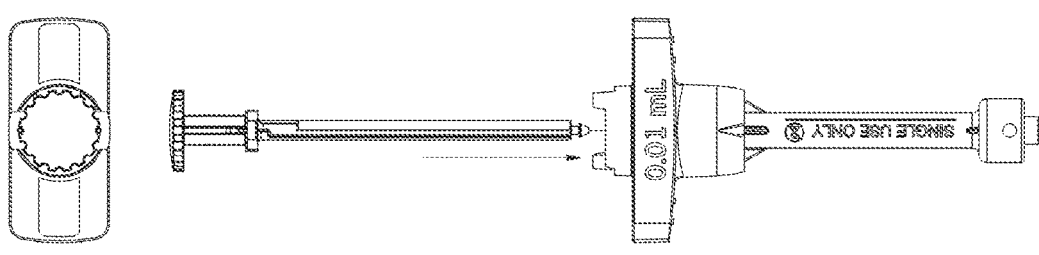
FIG. 38f

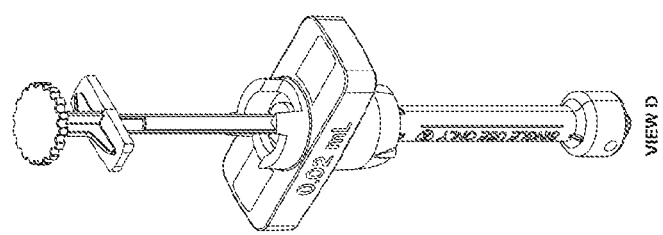
VIEW D
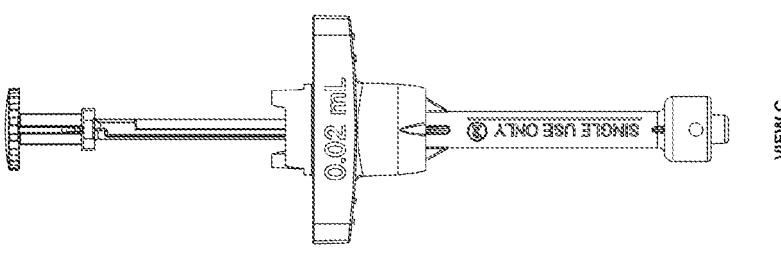
VIEW C
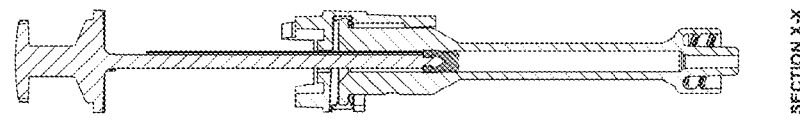
SECTION X-X
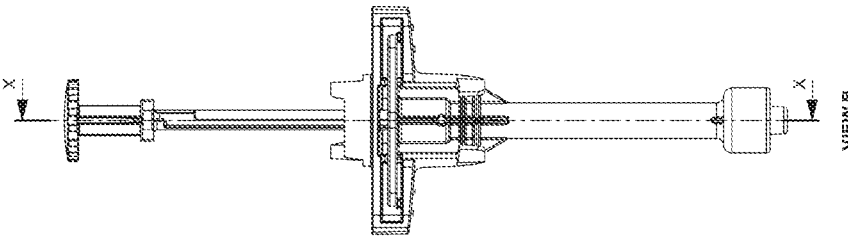
VIEW B
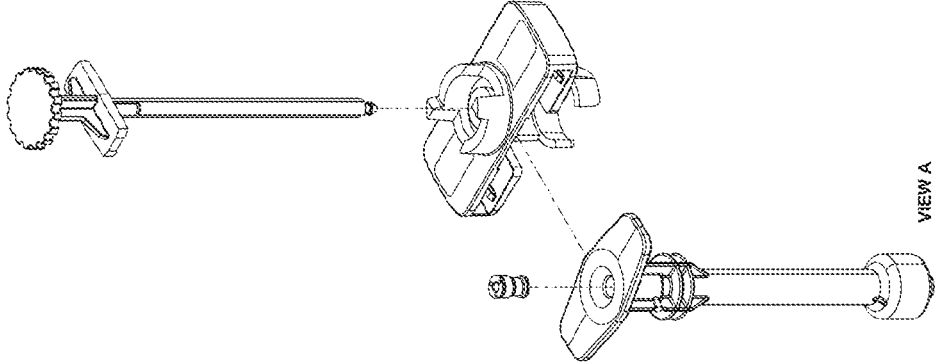
VIEW A
FIG. 38g

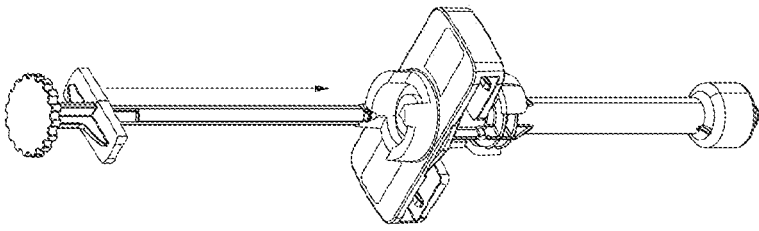
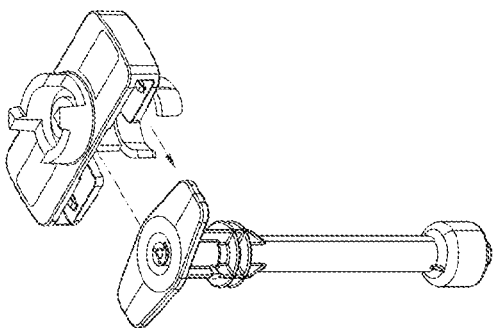
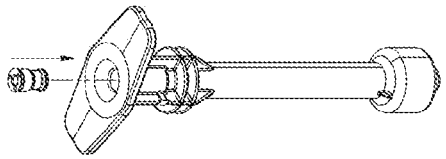
FIG. 38h

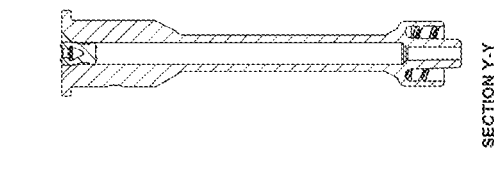
SECTION Y-Y
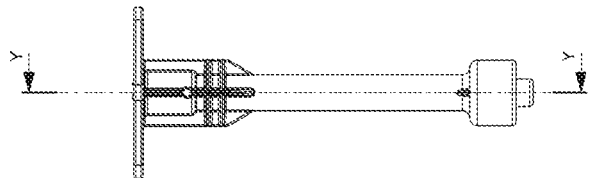
FIG. 38I
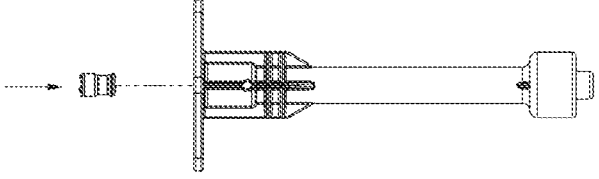

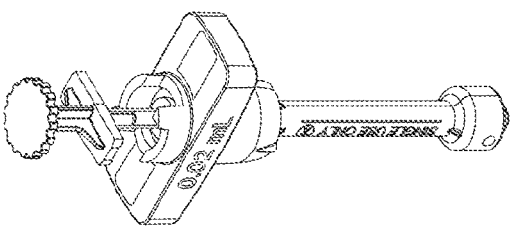
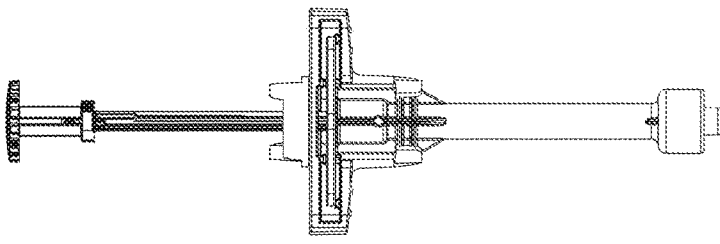
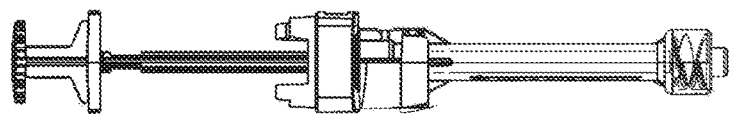
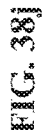
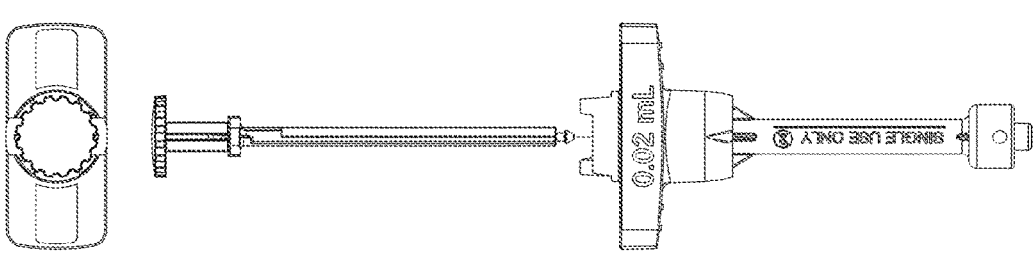
FIG. 38J

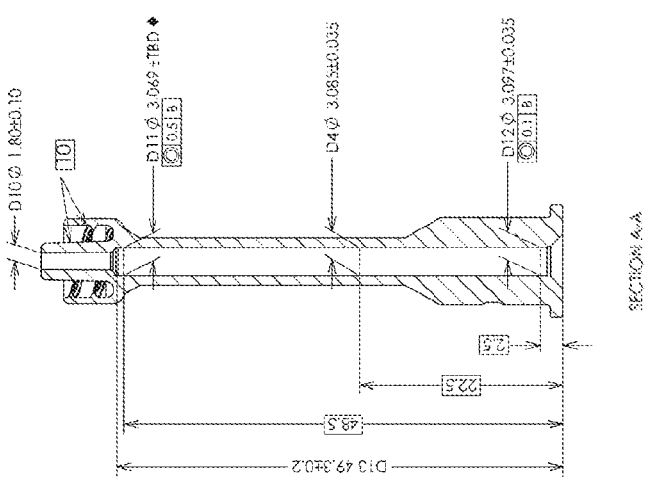
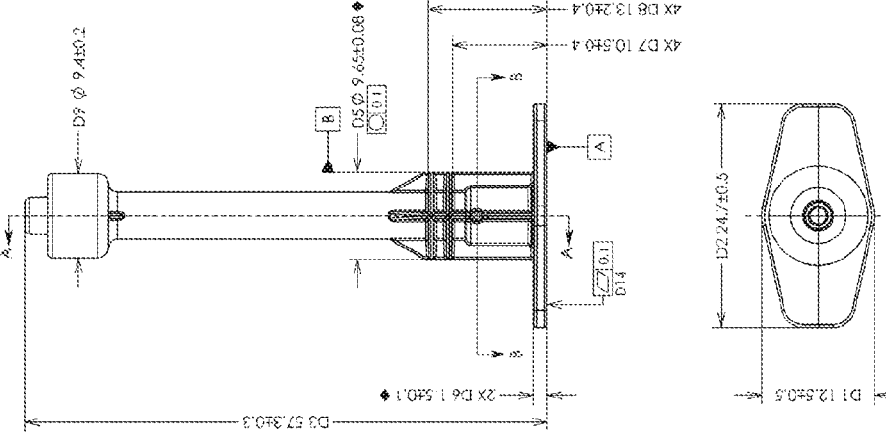
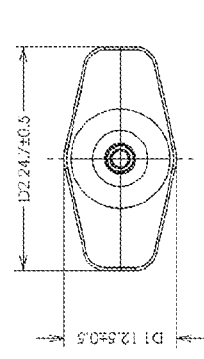
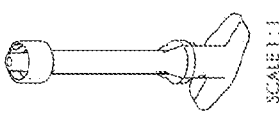
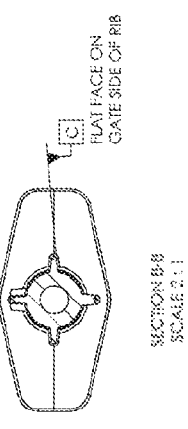
FIG. 38I

Notes:

- Drawing may be not to scale
- Radii without dimension 0.1 - 0.15 [0.004 - 0.006]
- * Dimension with theoretical intersection point

- Development drawing
- Dimension are preliminary and possibly subject to change

- Nominal surface area = 0,79 cm² [0,122 inch²]

GATE AND PERMITTED AREAS FOR EJECTION

VIEW F     VIEW G     VIEW H 0.02 mL

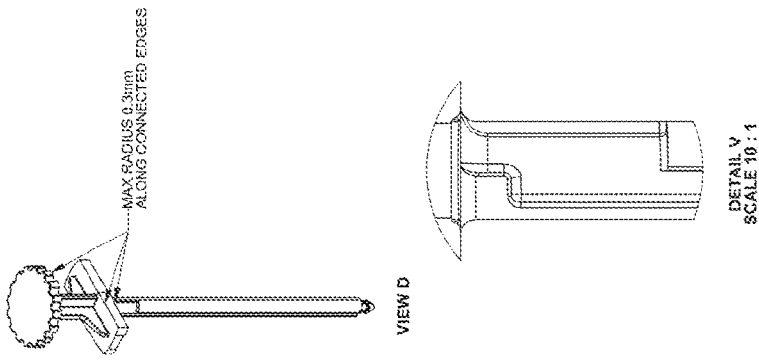
MAX RADIUS 0.3mm
ALONG CONNECTED EDGES
VIEW D
DETAIL V
SCALE 10 : 1
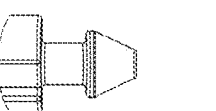
DETAIL U
SCALE 10 : 1
SECTION W-W
SCALE 10 : 1
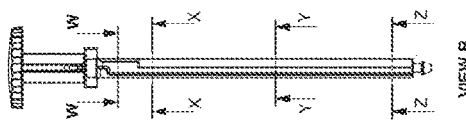
VIEW B
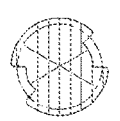
TYP FOR X-X, Y-Y, Z-Z
SCALE 10 : 1
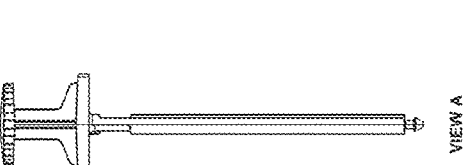
VIEW A
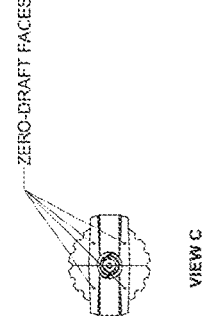
ZERO-DRAFT FACES
VIEW C
FIG. 38r

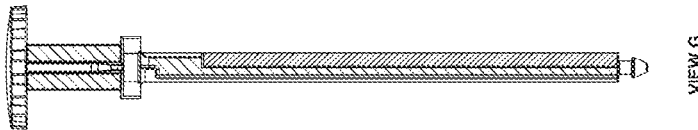
VIEW G
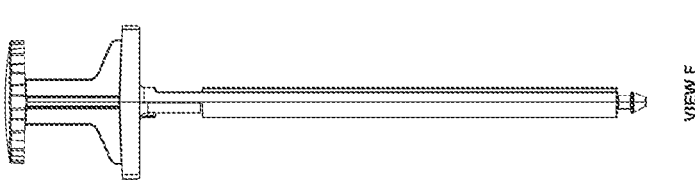
VIEW F
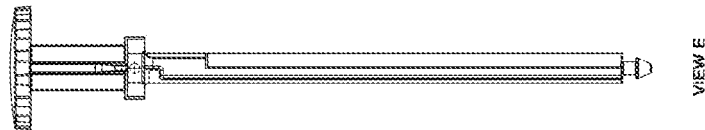
VIEW E
FIG. 38s

INJECTION DEVICE AND INJECTION SOLUTION TRANSFERRING SYSTEM

CROSS-REFERENCE TO RELATED APPLICATIONS

This application is a U.S. National Stage patent application of PCT/US2020/064698, titled "INJECTION DEVICE AND INJECTION SOLUTION TRANSFERRING SYSTEM," filed on Dec. 11, 2020, which claims priority to U.S. Provisional Application Ser. No. 62/947,462, entitled "INJECTION DEVICE AND INJECTION SOLUTION TRANSFERRING SYSTEM," filed on Dec. 12, 2019, the contents of each of which are hereby incorporated by reference in their entirety for all purposes.

FIELD

The present disclosure relates to an injection device, in particular a micro dose injection device such as, for example, an ophthalmic injection device for intraocular use. Further, the present disclosure relates to an injection solution transferring system for transferring an injection solution from a syringe to an injection device of this kind.

BACKGROUND

Typically, an injection solution to be administered to a patient for medical treatment is stored within a syringe having a container for accommodating the injection solution and a plunger which is displaceable relative to the container in order to expel the injection solution from the container. In case the medical treatment plan for a patient provides for the administration of a dose of the injection solution which corresponds to the filling volume of the syringe or in case the dosage of the injection solution is of minor importance for the desired therapeutic effect, the injection solution may be administered to the patient directly from the syringe. However, in case the medical treatment plan for a patient requires the administration of a dose of the injection solution which differs from the filling volume of the syringe and/or in case an accurate dosage of the injection solution is necessary, the injection solution, prior to administration, may be transferred from the syringe to an injection device which finally is used to inject the desired dose of the injection solution into the patient.

SUMMARY

The present disclosure is directed at the object of providing an injection device which allows the accurate and reliable administration of a micro dose of an injection solution to a patient. Further, the present disclosure is directed at the object of providing an injection solution transferring system for transferring an injection solution from a syringe to an injection device of this kind.

An injection device comprises an injection solution receptacle. The injection solution receptacle and the protective outer barrel can be made from any suitable material, or combination of materials, including a plastic material or from glass. Suitable plastic material comprises for example cycloolefin polymer or cycloolefin copolymer. An example of a glass material may be borosilicate glass. Preferably, the glass material is tungsten-free. In one embodiment, the injection solution receptacle may be uncoated. Uncoated means that the injection solution receptacle does not contain any other material other than the material of which the injection solution receptacle is made of. Alternatively, the injection solution receptacle may comprise an internal coating. Internal coating means a coating on the inner side of the injection solution receptacle which is in contact with the injection solution. Examples of such an internal coating comprise silicone coating or a fluorocarbon film made from a modified ethylene-tetrafluoroethylene copolymer. The injection solution receptacle may be silicone free, or substantially silicone free, or may comprise a low level of silicone as lubricant. Preferably, the injection solution receptacle is made of a sterile plastic material. Preferably, the injection solution receptacle is made of a sterile plastic material. Preferably, the injection solution receptacle does not comprise an internal coating. In one embodiment, the injection solution receptacle may meet USP789.

The injection solution receptacle may be designed in the form of an inner injection solution receptacle which is contained within a protective outer barrel. An injection solution receptacle designed in the form of an inner injection solution receptacle may be formed integral with the protective outer barrel. In the region of its proximal end, the protective outer barrel may be provided with a flange element which may serve to connect the protective outer barrel and the inner injection solution receptacle to a housing of the injection device. For example, the housing of the injection device may comprise a suitably shaped and dimensioned receptacle for receiving the flange element and hence fastening the protective outer barrel and the inner injection solution receptacle to the housing.

A distal end of the injection solution receptacle of the injection device may be provided with a male part of a Luer taper which is adapted to interact with a female part of a Luer taper. The female part of a Luer taper may, for example, be provided on a connecting port of an adapter element of a filling adapter which may be used to connect the injection device to a syringe containing an injection solution to be transferred from the syringe to the injection solution receptacle of the injection device. By means of the Luer taper, a fluid-tight connection can be established between the distal end of the injection solution receptacle of the injection device and the adapter element of the filling adapter in a simple manner. The outer barrel of the injection device, in the region of its distal end, may be provided with a Luer thread which is adapted to interact with a complementary Luer thread provided at the second connecting port of the adapter element of the filling adapter, in particular in the region of its outer circumference. As a result, also a reliable connection between the outer barrel of the injection device and the adapter element of the filling adapter can be effected.

The injection device further comprises a plunger. The plunger may be made of polycarbonate. At least a portion of the plunger is slidably received within the injection solution receptacle. The plunger is displaceable relative to the injection solution receptacle in a distal direction along a longitudinal axis of the plunger in order to expel an injection solution contained in the injection solution receptacle from the injection solution receptacle. At its proximal end which may protrude from the injection solution receptacle in a proximal direction, the plunger may carry an actuation button which may be depressed by a user in order to displace the plunger relative to the injection solution receptacle in the distal direction along the longitudinal axis of the plunger. At its distal end, the plunger may be provided with a tip element which may be attached to a plunger rod. A coupling between the plunger rod and the tip element may be effected, for example, by the interaction of a tip barb provided at a distal end of the plunger rod with a barb receptacle of the tip element. Further, the tip element may be provided with a sealing element which, for example, may be provided in the region of an outer circumferential surface of the tip element and which sealingly interacts with an inner circumferential surface of the injection solution receptacle.

The injection device further comprises a first plunger stop mechanism which is adapted to stop a displacement of the plunger relative to the injection solution receptacle in the distal direction at a first dosing position. Further, the injection device comprises a second plunger stop mechanism which is adapted to stop a displacement of the plunger relative to the injection solution receptacle from the first dosing position in the distal direction at a second dosing position. The first and the second dosing position of the plunger are selected in such a manner that the plunger, upon being displaced relative to the injection solution receptacle between the first and the second dosing position is adapted to expel a desired dose of the injection solution contained in the injection solution receptacle from the injection solution receptacle.

After filling the injection solution receptacle with the injection solution to be administered to a patient, a user of the injection device can expel excess injection solution from the injection solution receptacle by displacing the plunger relative to the injection solution receptacle in the distal direction until the plunger reaches the first dosing position. Upon reaching the first dosing position, the first plunger stop mechanism stops further displacement of the plunger in the distal direction. Consequently, the user is prevented from expelling too much injection solution from the injection solution receptacle. The residual injection solution contained in the injection solution receptacle can then be administered to a patient by further displacing the plunger in the distal direction until the plunger reaches the second dosing position. Upon reaching the second dosing position, the second plunger stop mechanism stops further displacement of the plunger in the distal direction and hence prevents that too much injection solution is administered to the patient.

The injection device allows the accurate and reliable administration of a micro dose of an injection solution to a patient. Further, the injection device can easily and comfortably be handled by a user. The injection device therefore is particularly suitable for treating a pediatric patient. In particular, the injection device may be designed in the form of an ophthalmic injection device for intraocular use.

In one embodiment, the injection device is filled with a dosage volume (i.e. the volume of injection solution intended for delivery to the patient) of between about 1 μL to about 50 μL, preferably between about 10 μL to about 20 μL, of an injection solution. In another embodiment, the injection device is filled with a dosage volume of 50 μL to 250 μL of injection solution. In yet another embodiment, the injection device is filled with a dosage volume of 25 μL to 125 μL of injection solution. In a preferred embodiment, the injection device is filled with a dosage volume of 5 μL, or 10 μL, or 20 μL, or 30 μL of an injection solution.

The injection device may be filled with any injection solution, for example an injectable medicament. In one embodiment, the injection device is filled with an injectable medicament comprising an active ingredient suitable for the treatment of an ocular disease. Examples of such ocular diseases include retinopathy of prematurity, geographic atrophy, glaucoma, choroidal neovascularisation, age-related macular degeneration (both wet and dry forms), macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, retinitis pigmentosa, Leber's congential aumaurosis, Bietti crystalline dystrophy, and proliferative retinopathy. In one embodiment, the medicament comprises a small molecule drug. In one embodiment, the medicament comprises a biologic active. The biologic active may be an antibody (or fragment thereof), a non-antibody protein, nucleic acids for gene therapy or cellular material for cell therapy. In one embodiment, the medicament comprises a VEGF antagonist. Suitable VEGF antagonists include ranibizumab (Lucentis™), bevacizumab (Avastin™), brolucizumab (Beovu®; also known as RTH258), aflibercept (Eylea™, also known as VEGF-Trap Eye), conbercept (KH902 from Chengdu Kanghong Biotechnologies Co. Ltd, described as FP3 in WO2005/121176, the contents of which are hereby incorporated by reference) and the related glycoform KH906 or pazopanib (from GlaxoSmithKline).

In a preferred embodiment, the injection device is filled with 0.1 mg or 0.2 mg ranibizumab in 20 μL injection solution. In a most preferred embodiment, the injection device is filled with 20 μL of ranibizumab (0.2 mg) and used for the treatment of retinopathy of prematurity.

In a preferred embodiment of the injection device, the first plunger stop mechanism comprises a dosing element which is attached to the plunger and which is adapted to abut against a first dosing surface provided on a housing element. Alternatively or additionally thereto, the second plunger stop mechanism may comprise a dosing element which is attached to the plunger and which is adapted to abut against a second dosing surface provided on a housing element.

Preferably, the dosing element of the first and/or the second plunger stop mechanism is formed integral with the plunger. For example, the dosing element may be designed in the form of a rib which may protrude from a surface of an actuation button of the plunger in the direction of the inner solution receptacle. Basically, it is conceivable that the injection device comprises a first dosing element associated to the first plunger stop mechanism and a second dosing element associated to the second plunger stop mechanism. Preferably, however, the injection device comprises only one dosing element which is attached to the plunger and which is associated to both the first and the second plunger stop mechanism. A single dosing element may be adapted, upon movement of the plunger in the distal direction, to first abut against the first dosing surface when the plunger reaches the first dosing position and then, upon further movement of the plunger from the first dosing position in the distal direction, against the second dosing surface when the plunger reaches the second dosing position.

The first and the second dosing surface may be provided on different housing elements of the injection device. In a preferred embodiment of the injection device, the first and the second dosing surface, however, both are formed on a first housing element, i.e. on the same housing element of the injection device. The first and the second dosing surface preferably extend substantially parallel to each other, wherein the second dosing surface may be arranged parallel offset relative to the first dosing surface in the distal direction. A distance between the first and the second dosing surface in the distal direction may correspond to a desired travel distance of the plunger in the distal direction between the first and the second dosing position. Hence, by suitably arranging the first and the second dosing surface, the desired plunger displacement between the first and the second dosing position and hence the desired injection solution dose to be expelled from the injection solution receptacle upon displacing the plunger from the first to the second dosing position can be set. The first and the second dosing surface may extend substantially parallel to an abutting surface of the dosing element. For example, the first and the second dosing surface as well as the abutting surface of the dosing element may extend substantially perpendicular to the longitudinal axis of the plunger.

The first plunger stop mechanism may be designed in such a manner that it provides a resistance force that is adapted to stop the displacement of the plunger at the first dosing position, but that can be overcome, for example by increasing the actuation force acting on the plunger. In a particular preferred embodiment of the injection device, the first plunger stop mechanism, however, is adapted to provide a hard stop for the plunger, i.e. is adapted to prevent the plunger from being displaced relative to the injection solution receptacle from the first dosing position in the distal direction without damaging the first plunger stop mechanism. In particular in case the first plunger stop mechanism is designed as a hard stop for the plunger, the injection device preferably further comprises a plunger releasing mechanism which is adapted to deactivate the first plunger stop mechanism in order to release the plunger and to thus allow a displacement of the plunger relative to the injection solution receptacle from the first dosing position in the distal direction, i.e. in the direction of the second dosing position.

Also the second plunger stop mechanism may be designed in such a manner that it provides a resistance force that is adapted to stop the displacement of the plunger at the second dosing position, but that can be overcome, for example by increasing the actuation force acting on the plunger. In a particular preferred embodiment, the second plunger stop mechanism, however, is adapted to provide a hard stop for the plunger, i.e. is adapted to prevent the plunger from being displaced relative to the injection solution receptacle from the second dosing position in the distal direction without damaging the second plunger stop mechanism. The dose of the injection solution to be administered to a patient can then be set in a particularly accurate manner.

Preferably, the plunger releasing mechanism is adapted to allow a movement of at least one of the dosing element and the first dosing surface in order to disengage the dosing element from the first dosing surface. The movement of the dosing element and/or the first dosing surface may be manually induced by a user of the injection device. In a particular preferred embodiment of the injection device, it is sufficient for a user to move only the first dosing surface for disengaging the dosing element from the first dosing surface. As a result, it is not necessary for the user to induce a movement of the plunger for activating the plunger releasing mechanism. For example, only the housing element carrying the first dosing surface may be moved for activating the plunger releasing mechanism, whereas the plunger may remain in its position, which simplifies the use of the injection device.

The plunger releasing mechanism may be adapted to allow a rotational movement of at least one of the dosing element and the first dosing surface in order to disengage the dosing element from the first dosing surface. For example, the plunger releasing mechanism may be activatable by a manually induced rotation of the plunger and/or the first dosing surface. In particular, the plunger releasing mechanism may be adapted to allow a rotational movement of the housing element carrying the first dosing surface for activating the plunger releasing mechanism. The actuation of a rotational movement of the plunger and/or the first dosing surface and in particular of only the first dosing surface can easily be distinguished by a user from the pressing actuation of the plunger so as to move the plunger in the distal direction. As a result, the use of the injection device is further simplified.

In a preferred embodiment of the injection device, the first and the second dosing surface are arranged offset relative to each other, for example on different or the same housing element(s), in a circumferential direction of the plunger. The plunger releasing mechanism then may be adapted to displace the first and the second dosing surface in the circumferential direction of the plunger, in order to disengage the dosing element from the first dosing surface and to simultaneously align the second dosing surface with the dosing element, such that the dosing element abuts against the second dosing surface, when the plunger, upon being displaced relative to the injection solution receptacle from the first dosing position in the distal direction, reaches the second dosing position. Such a design of the plunger releasing mechanism allows a particularly simple and reliable handling of the injection device.

Preferably, the first and the second dosing surface are formed on the first housing element which is rotatable relative to the plunger. In case the first and the second dosing surface are arranged offset relative to each other on the first housing element in a circumferential direction of the plunger, disengagement of the dosing element from the first dosing surface and simultaneous arrangement of the second dosing surface in a position wherein the second dosing surface is ready for engagement with the dosing element, when the plunger, upon being displaced from the first dosing position in the distal direction, reaches the second dosing position can easily be achieved by simply rotating the first housing element by a suitable rotation amount.

The second dosing surface may be defined by a bottom surface of a recess formed in the first dosing surface. Preferably, the recess is designed, i.e. shaped and dimensioned, so as to allow the dosing element to be received in the recess. When the plunger is arranged in its first dosing position and the dosing element abuts against the first dosing surface, the recess defined in the first dosing surface, via a rotational movement of the first housing element, can be brought into alignment with the dosing element. As a result, the dosing element is disengaged from the first dosing surface and the plunger can further be displaced in the distal direction until the dosing element is received in the recess and the abutting surface formed on the dosing element abuts against the second dosing surface defined by the bottom surface of the recess. A depth of the recess which defines the distance between the first and the second dosing surface in the distal direction may correspond to the desired travel distance of the plunger in the distal direction between the first and the second dosing position.

The first housing element which carries the first and the second dosing surface, in particular in the region of an outer surface, may be provided with a gripping structure. For example, the gripping structure may be designed in the form of a gripping rib array with individual gripping ribs extending, in dependence on the shape of the outer surface of the first housing element, substantially in a direction along the longitudinal axis of the plunger. The gripping structure simplifies the handling of the plunger releasing mechanism.

Preferably, the plunger releasing mechanism comprises a marker system which is adapted to indicate an activation of the plunger releasing mechanism. The marker system may, for example, comprise a first marker element which is provided on the first housing element which carries the first and the second dosing surface, for example in the region of an outer surface thereof. The marker system may further comprise a second marker element which is provided on a second housing element of the injection device, in particular in the region of an outer surface thereof. The first and the second marker element may be arranged on the first and the second housing element in such a position that they are positioned offset relative to each other, for example in a circumferential direction of the plunger, when the plunger releasing mechanism is not activated, but positioned in alignment with each other, when the plunger releasing mechanism is activated. The marker system provides a user with guidance information on how to activate the plunger release mechanism and hence simplifies the handling of the injection device.

The injection device preferably further comprises an activation mechanism which is adapted to prevent an activation of the plunger releasing mechanism unless the plunger is arranged at the first dosing position and which is adapted to allow an activation of the plunger releasing mechanism when the plunger is arranged at the first dosing position. The activation mechanism may be adapted to prevent a movement of the dosing element and/or the first dosing surface relative to each other unless the plunger is arranged at the first dosing position. In particular, the activation mechanism may be adapted to prevent a rotation of the first housing element carrying the first and the second dosing surface relative to the plunger carrying the dosing element unless the plunger is arranged at the first dosing position.

In a preferred embodiment of the injection device, the activation mechanism comprises a guiding channel which is provided on a circumferential surface of the plunger, which extends along the longitudinal axis of the plunger and which receives a guiding element provided on a housing element in such a manner that the guiding channel, upon displacement of the plunger relative to the injection solution receptacle, is displaced relative to the guiding element. An interaction between the guiding element and opposing side surfaces of the guiding channel may prevent a rotation of the plunger and the housing element relative to each other. When the activation mechanism comprises a guiding channel extending along the longitudinal axis of the plunger and a corresponding guiding element, the activation mechanism fulfills the double function to provide for a guided displacement of the plunger in the direction of its longitudinal axis on the one hand and to simultaneously prevent an unintentional deactivation of the first plunger stop mechanism when the plunger is not arranged at the first dosing position. The guiding element may be provided on the first housing element which carries the first dosing surface and preferably also the second dosing surface.

The activation mechanism may further comprise an activation channel which branches off from the guiding channel. For example, the activation channel may extend in a circumferential direction of the plunger substantially perpendicular to the guiding channel. The activation channel preferably is adapted to receive the guiding element when the plunger is arranged at the first dosing position and the first housing element which carries the guiding element and preferably also the first and the second dosing surface is rotated relative to the plunger. With such a design of the activation mechanism, the first dosing position of the plunger is defined by the position of the activation channel along the longitudinal axis of the plunger.

The first and the second dosing surface may be formed on the first housing element which is rotatable relative to the plunger. In case the first and the second dosing surface are arranged offset relative to each other on the first housing element in a circumferential direction of the plunger, disengagement of the dosing element from the first dosing surface and simultaneous arrangement of the second dosing surface in a position wherein the second dosing surface is ready for engagement with the dosing element, when the plunger, upon being displaced from the first dosing position in the distal direction, reaches the second dosing position can easily be achieved by simply rotating the first housing element by a suitable rotation amount.

The second dosing surface may be defined by a bottom surface of a recess formed in the first dosing surface. Preferably, the recess is designed, i.e. shaped and dimensioned, so as to allow the dosing element to be received in the recess. When the plunger is arranged in its first dosing position and the dosing element abuts against the first dosing surface, the recess defined in the first dosing surface, via a rotational movement of the first housing element, can be brought into alignment with the dosing element. As a result, the dosing element is disengaged from the first dosing surface and the plunger can further be displaced in the distal direction until the dosing element is received in the recess and the abutting surface formed on the dosing element abuts against the second dosing surface defined by the bottom surface of the recess.

The plunger release mechanism may further comprise a locking arrangement which is adapted to lock the first dosing surface in its position relative to the dosing element after the first dosing surface has been moved relative to the dosing element in order to become disengaged from the dosing element. The locking arrangement thus allows the plunger release mechanism to be used only once for deactivating the first plunger stop mechanism. As a result, reuse of the injection device is reliably prevented.

The locking arrangement may comprise a resilient locking clip which is adapted to be resiliently urged out of a rest position by the interaction with a locking element when the first dosing surface is moved relative to the dosing element so as to become disengaged from the dosing element. For example, the resilient locking clip may be provided on the second housing element, whereas the locking element may be provided on the first housing element which carries the first dosing surface and optionally also the second dosing surface. The resilient locking clip then may be resiliently deformed when the first housing element is rotated relative to the second housing element. The locking clip preferably further is adapted to deform back into its rest position after completion of the movement of the first dosing surface and to interact with the locking element so as to lock the first dosing surface in its position relative to the dosing element. In particular, the locking clip may interact with the locking element so as to prevent a counter rotation of the first housing element relative to the second housing element and the plunger, after the first housing element has been rotated once in order to disengage the first dosing surface from the dosing element and to align the second dosing surface with the dosing element.

The injection device may further comprise a limiting mechanism which is adapted to limit a movement of the dosing element and/or both the first dosing surface and the second dosing surface for disengaging the dosing element from the first dosing surface and for aligning the dosing element with the second dosing surface. The limiting mechanism prevents a user of the injection device from moving the dosing element and the first and the second dosing surface relative to each other in an excessive manner. Further, the limiting mechanism provides an haptic feedback to the user that the dosing element is properly disengaged from the first dosing surface and aligned with the second dosing surface, i.e. that the first plunger stop mechanism has been deactivated.

The limiting mechanism may in particular comprise a first limiting element which is provided on the first housing element carrying the first and the second dosing surface. Further, the limiting mechanism may comprise a second limiting element which is provided on a second housing element, the second housing element being adapted to remain stationary when the first housing element is moved, in particular rotated, for deactivating the first plunger stop mechanism. The first limiting element may be adapted to abut against the second limiting element when the dosing element is disengaged from the first dosing surface and aligned with the second dosing surface.

In case the injection device comprises an above-described activation mechanism with an activation channel and a guiding element formed on the first housing element which also carries the first and the second dosing surface, the movement of the first dosing surface relative to the dosing element attached to the plunger may also be limited by an interaction between the guiding element and an end face of the activation channel which may act as an abutting surface for the guiding element when the first housing element, after being rotated relative to the plunger, has reached a position wherein the dosing element is disengaged from the first dosing surface and aligned with the second dosing surface.

The injection device may further comprise a first drag mechanism adapted to exert a retaining force which retains the plunger in its current position relative to the injection solution receptacle. The first drag mechanism thus prevents an unintentional displacement of the plunger relative to the injection solution receptacle—in other words, due to the presence of the first drag mechanism, active manual actuation, for example by the application of a pressing force, is necessary for displacing the plunger relative to the injection solution receptacle. The first drag mechanism may comprise a resilient drag element which may, for example, be provided on the second housing element. The resilient drag element may be adapted to exert a resilient retaining force on the plunger, i.e. the resilient drag element may be resiliently urged out of a rest position into a biasing position by an interaction with the plunger and, due to its resiliency, may apply a resilient reaction force on the plunger which retains the plunger in its current position. The resilient drag element may in particular interact with a drag rib which is provided on the outer circumferential surface of the plunger and which extends substantially parallel to the longitudinal axis of the plunger.

Alternatively or additionally thereto, the injection device may also comprise a second drag mechanism adapted to exert a retaining force which retains the first housing element in its current position, i.e. which retains the first housing element in its position relative to the second housing element. The second drag mechanism thus prevents an unintentional displacement of the first housing element relative to the second housing element and hence an unintentional deactivation of the first plunger stop mechanism. The second drag mechanism may comprise a friction element which is provided on the first limiting element of the limiting mechanism and which is adapted to interact with a retaining element of the second housing element.

The injection device may further comprise a plunger positioning mechanism which is adapted to prevent a displacement of the plunger relative to the injection solution receptacle from a proximal end position in a proximal direction. The plunger positioning mechanism may, for example, comprise a distal end face of the guiding channel which is provided in the circumferential surface of the plunger. An interaction between the distal end face of the guiding channel and the guiding element received therein then may define the proximal end position of the plunger.

The injection device may be pre-filled with a compound, via a pre-filled syringe (14), a vial, or other reservoir.

In one embodiment, the injection device (whether pre-filled or not) is sterilized and provided in a sealed package. In one embodiment, the injection device is pre-filled with a suitable injection solution and terminally sterilized. Such a terminal sterilization step may comprise known techniques such as ethylene oxide sterilization or hydrogen peroxide sterilization.

Example solution dispensing devices are disclosed herein. An example solution dispensing device comprises: a rotatable plunger; a solution receptacle having a first end configured to slidably receive the rotatable plunger and a second end configured to dispense solution contained in the solution receptacle, wherein the solution dispensing device is configured to: allow the rotatable plunger, while it is in a first orientation, to be slidably displaced along a first axis to be positioned at a first position relative to the solution receptacle, and allow the rotatable plunger, while it is in a second orientation, to be slidably displaced along the first axis from the first position to a second position relative to the solution receptacle, wherein: the second position is closer to the second end of the solution receptacle than the first position, and slidably displacing the rotatable plunger from the first position to the second position dispenses a quantity of the solution contained in the solution receptacle; a first stop member configured to prevent the rotatable plunger from being slidably displaced to the second position while the rotatable plunger is at the first position and in the first orientation; and a second stop member configured to prevent the rotatable plunger from rotating in a first direction about the first axis while the rotatable plunger is at the first position and in the first orientation.

Example methods for dispensing solution from a solution dispensing device having a rotatable plunger, a solution receptacle, a first stop member, and a second stop member are disclosed herein. An example method comprises, slidably inserting the rotatable plunger into a first end of the solution receptacle, wherein a second end of the solution receptacle is configured to dispense a solution contained in the solution receptacle; while the rotatable plunger is in a first orientation, slidably displacing the rotatable plunger along a first axis until the rotatable plunger is in a first position relative to the solution receptacle, wherein: the first stop member prevents the rotatable plunger from being slidably displaced to a second position relative to the solution receptacle that is closer to the second end of the solution receptacle than the first position while the rotatable plunger is at the first position and in the first orientation, and the second stop member prevents the rotatable plunger from rotating in a first direction about the first axis while the rotatable plunger is at the first position and in the first orientation; rotating the rotatable plunger in a second direction about the first axis until the rotatable plunger is in a second orientation at the first position; while the rotatable plunger is in the second orientation, slidably displacing the rotatable plunger along the first axis until the rotatable plunger is in the second position relative to the solution receptacle, wherein slidably displacing the rotatable plunger from the first position to the second position dispenses a quantity of the solution contained in the solution receptacle.

BRIEF DESCRIPTION OF THE DRAWINGS

FIGS. 37a to 37b show a flow diagram of a process for using a solution dispensing device to dispense a quantity of solution, according to various examples.

DETAILED DESCRIPTION

Figure 1:
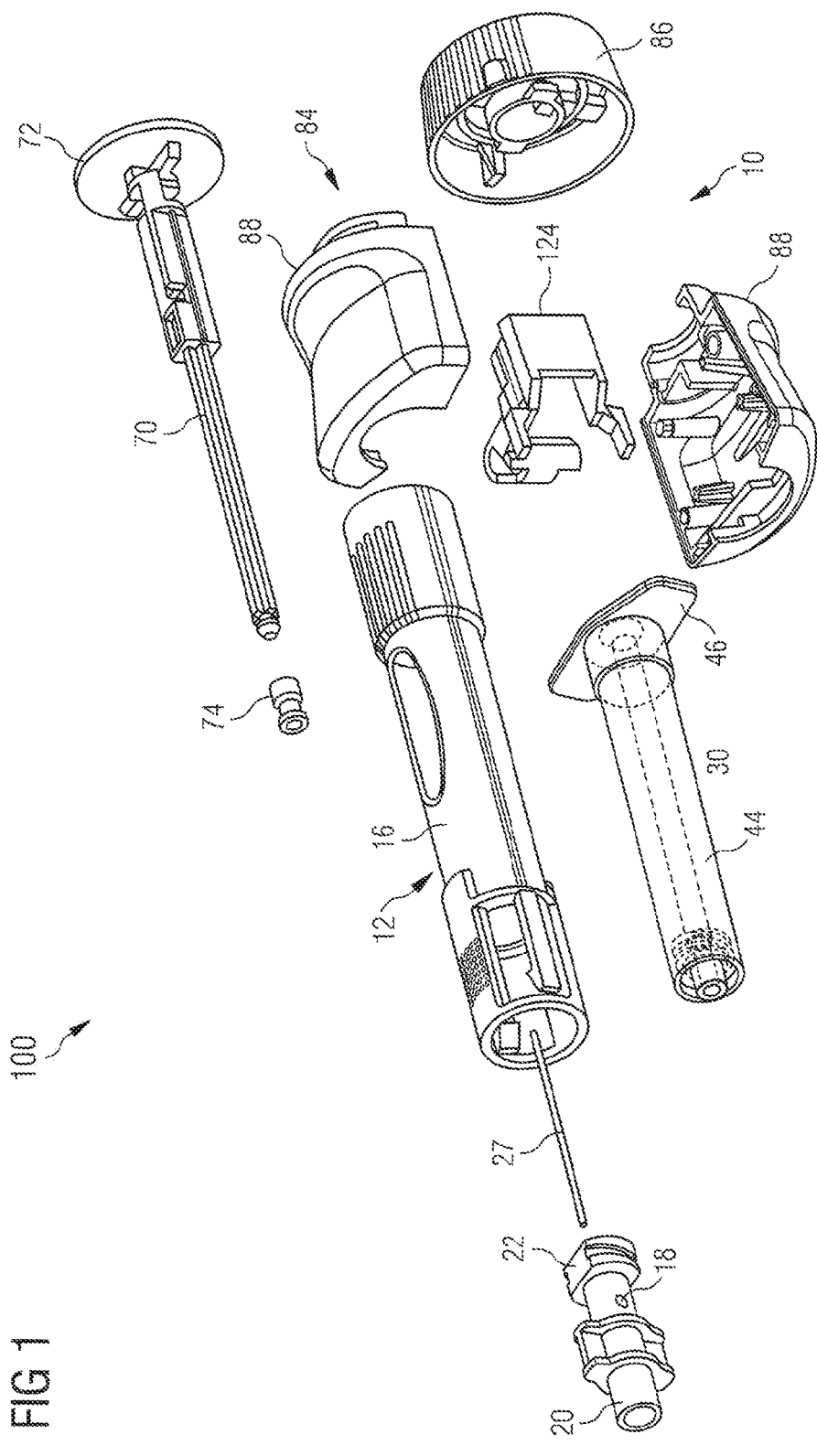
FIG. 1 shows an exploded view of an injection solution transferring system which comprises a filling adapter and injection device.
Figure 2:
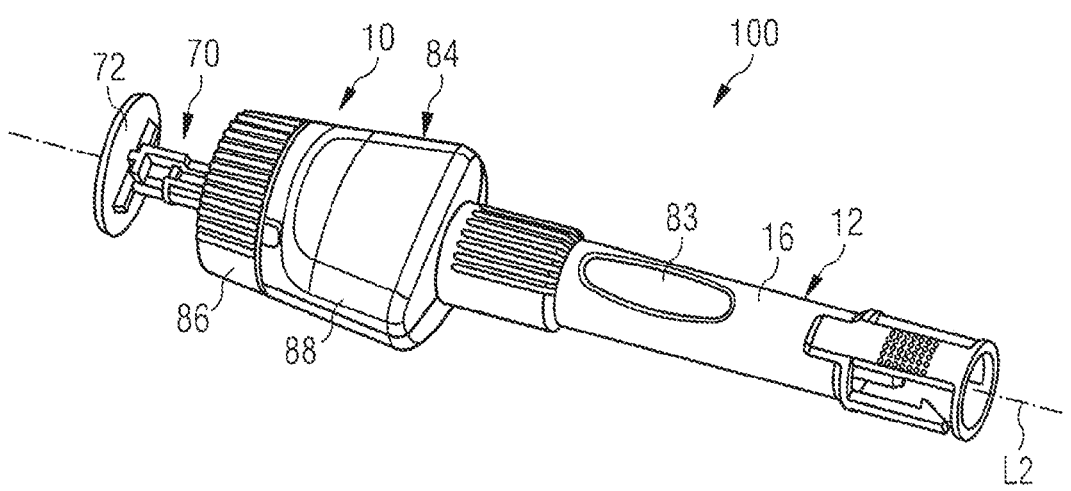
FIG. 2 shows a three-dimensional view of the filling adapter and the injection device in a connected state.

FIGS. 1 and 2 show an injection solution transferring system 100 which comprises an injection device 10 and a filling adapter 12. The filling adapter 12 serves to connect a syringe 14 containing an injection solution to the injection device 10 for filling the injection device 10 with the injection solution from the syringe 14 as shown in FIGS. 33a to 33d and as will be described further below. The syringe 14 is designed in the form of a pre-filled syringe 14 which contains an injection solution for intraocular use.

Figure 4:
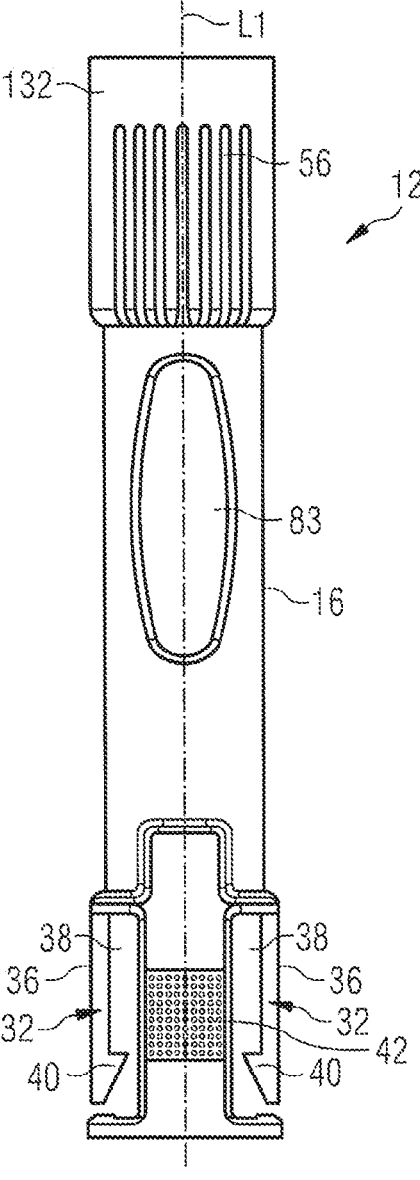
FIGS. 4 and 5 show detailed three-dimensional views of a hollow sleeve of the filling adapter.
Figure 5:
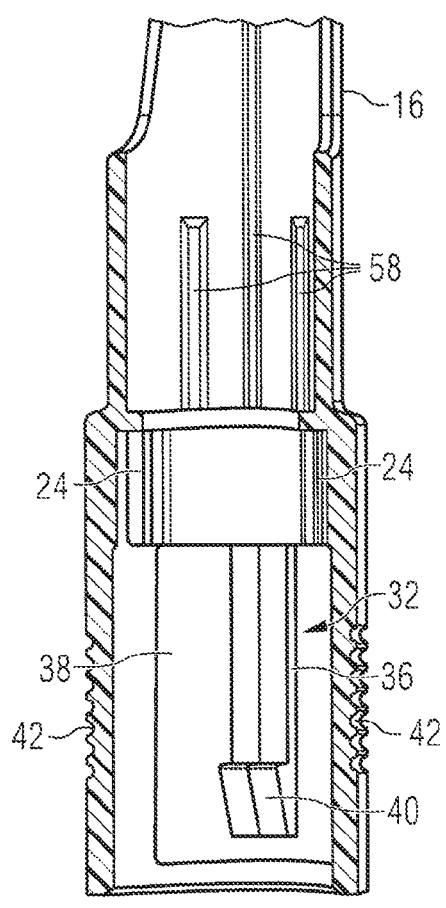
Figure 6:
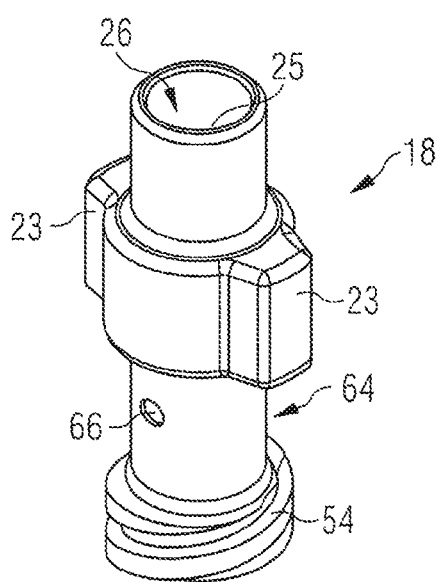
FIGS. 6 and 7 show detailed three-dimensional views of an adapter element of the filling adapter.
Figure 7:
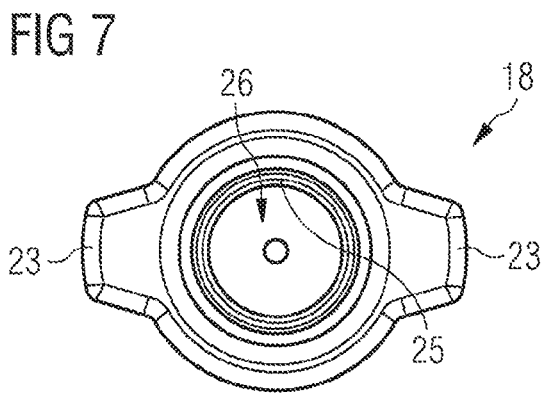

The filling adapter 12 comprises a hollow sleeve 16 which is shown in greater detail in FIGS. 4 and 5. The hollow sleeve 16 is made of a coloured plastic material, for example Polycarbonate/Acrylnitril Butadien Styrol (PC-ABS) and is provided with an inner lumen which is dimensioned so as to allow the insertion of at least a distal portion of the syringe 14 at one end and of at least a distal portion of the injection device 10 at an opposing end. In the exemplary embodiment of a filling adapter 12 shown in the drawings, the hollow sleeve 16 has a substantially circular hollow cylindrical shape and the lumen extending therethrough has a substantially circular cross-sectional shape.

The filling adapter 12 further comprises an adapter element 18 which is accommodated within the hollow sleeve 16 and which comprises a first connecting port 20 and a second connecting port 22. The adapter element 18 may, for example, be made of polycarbonate and is shown in greater detail in FIGS. 6 to 10. As shown in particular in FIG. 8, the adapter element 18 is provided with two retention shoulders 23 which protrude from an outer circumferential surface of the adapter element 18 in opposing directions. Each retention shoulder 23 interacts with a pair of complementary crush ribs 24 protruding from an inner circumferential surface of the hollow sleeve 16 in order to fix the adapter element 18 in its position within the hollow sleeve 16. The retention shoulders 23 and the complementary crush ribs 24 create an interference fit so as to reliably fix the adapter element 18 in its position within the hollow sleeve 16.

Figure 33:
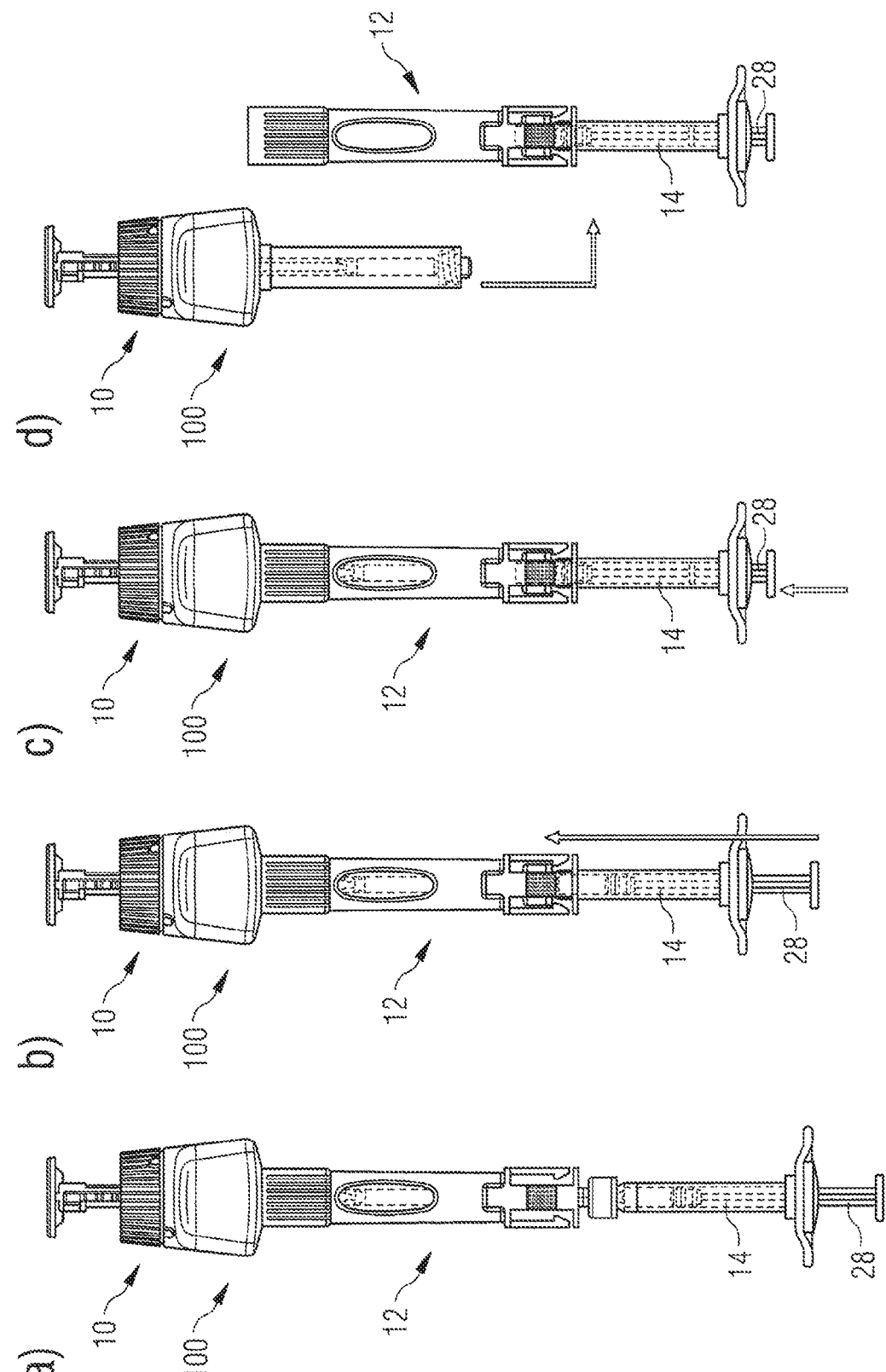
FIGS. 33a to 33d show the use of the injection solution transferring system upon filling the injection device with an injection solution from a syringe.

The first connecting port 20 of the adapter element 18 is adapted to be connected to the syringe 14, i.e. a distal end of the syringe 14, when the filling adapter 12 is connected to the syringe 14 as shown in FIGS. 33a to 33c. As becomes apparent in particular from FIG. 10, the first connecting port 20 of the adapter element 18 forms a female Luer taper 25 which is adapted to interact with a male Luer taper provided at the distal end of the syringe 14 in order to establish a fluid-tight connection between the syringe 14 and the adapter element 18. The second connecting port 22 of the adapter element 18 is adapted to be connected to the injection device 10.

Figure 9:
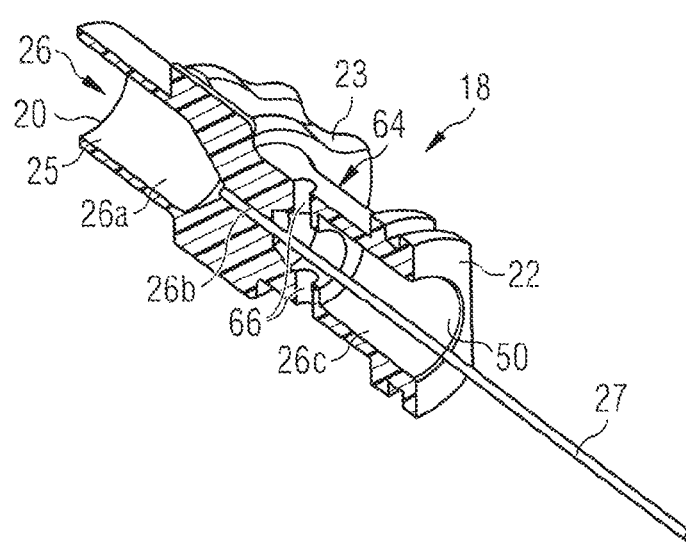
FIG. 9 shows a three-dimensional longitudinal cut view of the adapter element and a cannula of the filling adapter.
Figure 10:
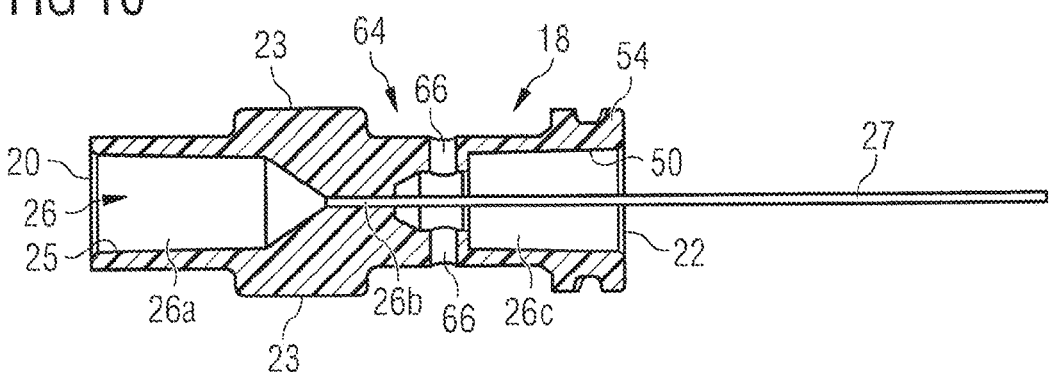
FIG. 10 shows a longitudinal section of the adapter element and the cannula of the filling adapter.

The adapter element 18 is provided with a through-opening 26 extending therethrough in a direction substantially parallel to a longitudinal axis L1 of the filling adapter 12, see in particular FIG. 10. A cannula 27 protrudes from the second connecting port 22 of the adapter element 18 and is arranged in fluid communication with the through-opening 26 extending through the adapter element 18, see in particular FIGS. 9 and 10. The cannula 27 is made of stainless steel. The hollow sleeve 16 of the filling adapter 12, however, extends beyond a distal tip of the cannula 27. As a result, a user is protected from the cannula 27 during handling of the filling adapter 12.

The adapter element 18 serves to establish a fluid connection between the syringe 14 and the injection device 10, i.e. when the syringe 14 is connected to the first connecting port 20 of the adapter element 18 and the injection device 10 is connected to the second connecting port 22 of the adapter element 18 as shown in FIG. 33*a*, injection solution contained in the syringe 14 may be transferred into the injection device 10 by manually pushing a plunger 28 of the syringe 14 as shown in FIGS. 33*b* and 33*c* so as to expel the injection solution from the distal end of the syringe 14 into the through-opening 26 provided in the adapter element 18 and further via the cannula 27 into an injection solution receptacle 30 of the injection device 10.

As becomes apparent in particular from FIGS. 4 and 5, the hollow sleeve 16 of the filling adapter 12, in the region of a first end which faces the syringe 14 when the syringe 14 is brought into engagement with the first connecting port 20 of the adapter element 18, the hollow sleeve 16 comprises at least one resilient clip 32 which is adapted to engage with a collar 34 of the syringe 14 when the syringe 14 is brought into engagement with the first connecting port 20 of the adapter element 18, see FIGS. 33*a* and 33*b*. In the embodiment of a hollow sleeve 16 shown in the drawings, the hollow sleeve 16 is provided with two resilient clips 32. Each resilient clip 32 comprises an arm 36 which extends in a recess 38 provided in the hollow sleeve 16 substantially parallel to the longitudinal axis L1 of the filling adapter 12 in the direction of the first end of the hollow sleeve 16. A latching nose 40 protrudes from an inner surface of the arm 36 in the region of a free end of the arm 36.

When the syringe 14 is brought into engagement with the first connecting port 20, due to the interaction with the collar 34 of the syringe 14, the resilient clip 32 is bent outwards. However, as soon as the syringe 14 has reached its final position with respect to the adapter element 18, i.e. when the distal tip of the syringe 14 is connected to the first connecting port 20 of the adapter element 18 and the syringe 14 assumes the position relative to the hollow sleeve 16 which is shown in FIG. 33*b*, the resilient clip 32 resumes its original position substantially parallel to the longitudinal axis L1 of the filling adapter 12 such that the latching nose 40 comes into engagement with an end face of the collar 34 of the syringe 14. As a result, the syringe 14 is firmly connected to the hollow sleeve 16.

In the region of its first end, the hollow sleeve 16 at its outer circumferential surface is provided with two first gripping structures 42 each of which is designed in the form of a nub array. The first gripping structure simplifies the handling of the filling adapter 12 during connecting the syringe 14 to the filling adapter 12. Further, the hollow sleeve 16, in the region of its first end and the region of a second end which faces the injection device 10 when the injection device 10 is brought into engagement with the second connecting port 22 of the adapter element 18, has an outer diameter which is larger than an outer diameter of the hollow sleeve 16 in an intermediate section arranged between the first and the second end. Such a design of the hollow sleeve 16 further simplifies the gripping and thus the handling of the filling adapter 12.

Figure 3:
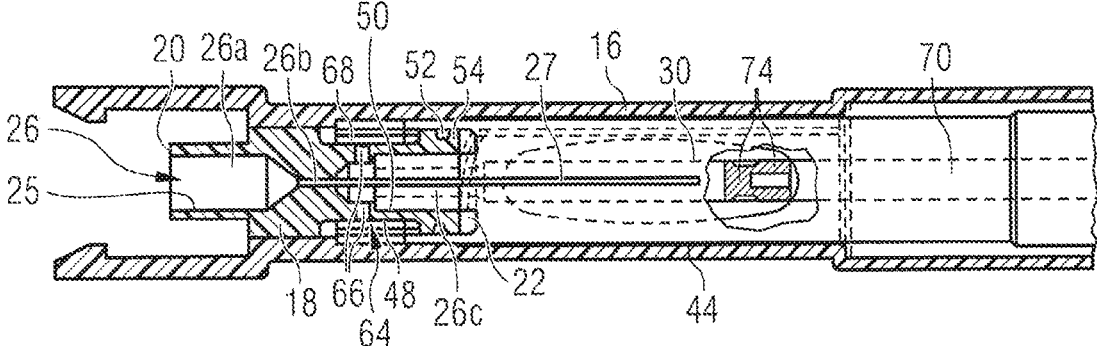
FIG. 3 shows a longitudinal section of the filling adapter being connected to the injection device.
Figure 11:
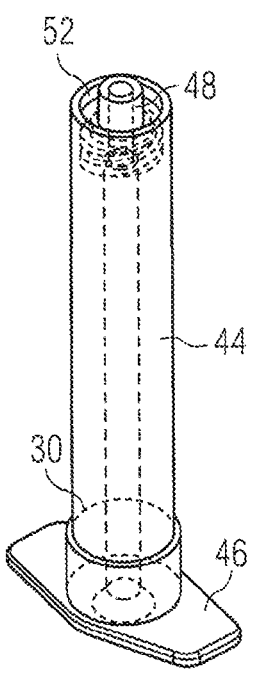
FIG. 11 shows a detailed view of an injection solution receptacle of the injection device.

As shown in in FIG. 11, the injection solution receptacle 30 of the injection device 10 is designed in the form of an inner injection solution receptacle 30 which is contained within a protective outer barrel 44. The inner injection solution receptacle 30 and the protective outer barrel 44 are formed integral with each other and are made of a sterile plastic material. In the region of its proximal end, the protective outer barrel 44 is provided with a flange element 46. A distal end of the injection solution receptacle 30 is provided with a male Luer taper 48 which interacts with a female Luer taper 50 provided on the second connecting port 22 of the adapter element 18 of the filling adapter 12 when the filling adapter 12 is connected to the injection device 10 as shown in FIGS. 2 and 3. By means of the Luer tapers 48, 50, a fluid-tight connection can be established between the distal end of the injection solution receptacle 30 and the adapter element 18 of the filling adapter 12.

As further becomes apparent from FIG. 11, the outer barrel 44 of the injection device 10, in the region of its distal end, is provided with a Luer thread 52. The Luer thread 52 interacts with a complementary Luer thread 54 provided at an outer circumference of the second connecting port 22 of the adapter element 18, see FIGS. 6 and 8 to 10, when the filling adapter 12 is connected to the injection device 10 as shown in FIGS. 2 and 3. As a result, also a reliable connection between the outer barrel 44 of the injection device 10 and the adapter element 18 of the filling adapter 12 can be effected.

In order to simplify the handling of the filling adapter 13 during bringing the injection device 10 into engagement with the second connecting port 22 of the adapter element 18, the hollow sleeve 16, in the region of a second end which faces the injection device 10 when the injection device 10 is brought into engagement with the second connecting port 22 of the adapter element 18, at its outer circumferential surface is provided with a second gripping structure 56. The second gripping structure 56 is designed in the form of two gripping rib arrays with individual gripping ribs extending substantially parallel to the longitudinal axis L1 of the filling adapter 12.

Figure 15:
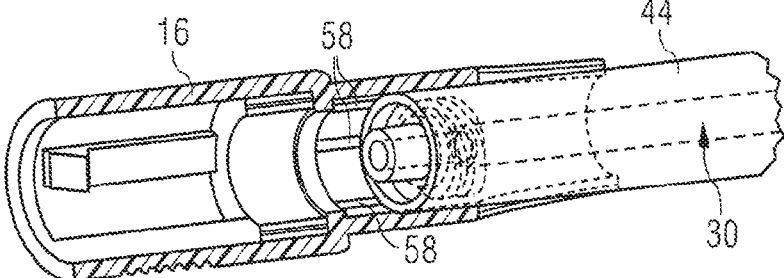
FIG. 15 shows the interaction between the guiding rib of the hollow sleeve with the injection solution receptacle of the injection device.

Further, as shown in FIG. 15, the hollow sleeve 16 is provided with longitudinal guiding ribs 58 which protrude from the inner circumferential surface of the hollow sleeve 16 and which extend substantially parallel to the longitudinal axis L1 of the filling adapter 12. The guiding ribs 58 serve to guide the injection device 10 into engagement with the second connecting port 22. The guiding function of the guiding ribs 58 prevents the cannula 27 from contacting the injection solution receptacle 30 of the injection device 10 upon connecting the filling adapter 12 to the injection device 10. The hollow sleeve 16 and the longitudinal guiding ribs 58 are designed, i.e. shaped and dimensioned, in such a manner that a close sliding fit is generated between the guiding ribs 58 and an outer surface of the outer barrel 44 of the injection device 10.

Turning back to FIGS. 9 and 10, the through-opening 26 extending through the adapter element 18 comprises an inlet section 26*a* which is arranged adjacent to the first connecting port 20. In use of the filling adapter 12, injection solution expelled from the syringe 14 thus enters the through-opening 26 via its inlet section 26*a* which has a flow cross-section which decreases in a direction of flow of the injection solution expelled from the syringe 14. Further, the through-opening 26 comprises an intermediate section 26*b* which, in the direction of flow of the injection solution expelled from the syringe 14 during use of the filling adapter 12, is arranged downstream of the inlet section 26*a*. The intermediate section 26*b* of the through-opening 26 has a substantially constant flow cross-section which substantially corresponds to the smallest flow cross-section of the inlet section 26a adjacent to the intermediate section 26b. Finally, the through-opening 26 comprises a receiving section 26c which, in the direction of flow of the injection solution expelled from the syringe 14 during use of the filling adapter 12, is arranged downstream of the intermediate section 26b, i.e. adjacent to the second connecting port 22. The receiving section 26c has a flow cross-section that is larger than the flow cross-section of the intermediate section 26b.

As further becomes apparent from FIGS. 9 and 10, the cannula 27 extends into at least a portion of the intermediate section 26b of the through-opening 26 so that the intermediate section 26b of the through-opening 26 or a portion thereof defines a cannula receiving bore of the adapter element 18 wherein a proximal end of the cannula 27 is fixed. The cannula 27 is received in the cannula receiving bore with a close slide fit. In addition, the cannula 27 is provided with bevelled ends. This design of the cannula 27 and the cannula receiving bore minimizes the generation of wear particles upon attaching the cannula 27 in the cannula receiving bore. The final bonding between the adapter element 18 and the cannula 27 is effected by means of a UV-cured glue. The cannula 27 extends from the intermediate section 26b of the through-opening 26, through the receiving section 26c of the through-opening 26 and the second connecting port 22 so as to protrude from the second connecting port 22. The receiving section 26c of the through-opening 26, the second connecting port 22 and the hollow sleeve 16 of the filling adapter 12 define a concentric arrangement around the cannula 27, see in particular FIG. 3.

Figure 8:
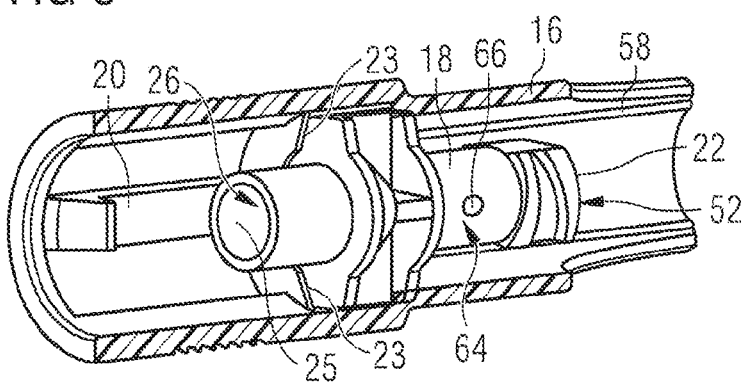
FIG. 8 shows the arrangement of the adapter element in the hollow sleeve of the filling adapter.

As shown in particular in FIG. 8, the adapter element 18 is provided with two retention shoulders 60 which protrude from an outer circumferential surface of the adapter element 18 in opposing directions in the region of the inlet section 26a and the intermediate section 26b of the through-opening 26 extending through the adapter element 18.

When the filling adapter 12 is connected to the injection device 10, the cannula 27 extends into the injection solution receptacle 30 of the injection device 10, i.e. a distal tip of the cannula 27 is arranged at a distance from the distal end of the injection solution receptacle 30 within the interior of the injection solution receptacle 30, see in particular FIG. 3. As a result, upon transferring injection solution from the syringe 14 to the injection device 10, injection solution exiting the syringe 14, via the cannula 27, is supplied to the injection solution receptacle 30 of the injection device 10 not in the region of the distal end of the injection solution receptacle 30, but at a position arranged at a distance from the distal end of the injection solution receptacle 30 within the interior of the injection solution receptacle 30.

By simply holding the filling adapter 12 and the injection device 10 in an upright position with the longitudinal axis L1 of the filling adapter 12 and a longitudinal axis L2 of the injection device 10 being oriented substantially vertically and with the distal end of the injection device 10 facing downwards as shown in FIGS. 33a to 33c, a gravity-driven flow of the injection solution from the distal tip of the cannula 27 downwards in a direction of the distal end of the injection solution receptacle 30 and further in the direction of the adapter element 18 can be induced. A part of the injection solution which is expelled from the distal tip of the cannula 27 and which in a gravity-driven manner flows back in the direction of the adapter element 18 is received in the receiving section 26c of the through-opening 26 provided in the adapter element 18. Gas bubbles which are entrapped within the injection solution and hence transferred from the syringe 14 to the injection solution receptacle 30 together with the liquid phase of the injection solution are entrained with this gravity-driven flow and, due to the higher specific density of the liquid phase of the injection solution, are forced in the direction of the distal end of the injection solution receptacle 30 and further in the direction of the adapter element 18.

Finally, the adapter element 18 is provided with a venting device 64 which is adapted to vent gas introduced from the syringe 14 into the injection device 10, i.e. the injection solution receptacle 30 of the injection device 10, via the through-opening 26 and the cannula 27 into the ambient. The venting device thus allows entrapped gas bubbles, in particular air bubbles, that are conveyed from the distal tip of the cannula 27 back to the adapter element 18 by the above described gravity-driven flow of the injection solution to be expelled into the ambient. The filling adapter 12 thus allows a gas free filling of the injection device 10 with the injection solution. As a result, manually expelling entrapped gas from the syringe 14 prior to connecting the syringe 14 to the filling adapter 12 can be dispensed with. Furthermore, an accurate and reliable preparation of a desired dose of the injection solution within the injection device 10 is made possible.

The venting device 64 comprises two radial bores 66 connecting the through-opening 26 extending through the adapter element 12 to the ambient. In particular, the radial bores 66 connect the receiving section 26c of the through-opening 26 to an outer circumferential surface of the adapter element 18 and hence to the ambient. In the embodiment of a filling adapter 18 shown in the drawings, the radial bores 66 of the venting device 64 extend coaxially from an outer circumferential surface of the adapter element 18 to the receiving section 26c of the through-opening 26 so as to connect the receiving section 26c of the through-opening 26 to the ambient. In order to ensure that gas bubbles entrapped in the injection solution can be vented to the ambient as desired without expelling a substantial amount of the liquid phase of the injection solution to the ambient, the flow cross-section, i.e. the diameter of the radial bores 66 is be selected in dependence on the physical properties, in particular the specific density, the viscosity and the surface tension of the injection solution to be transferred from the syringe 14 to the injection device 10.

In order to ensure proper functioning of the venting device 64, the retention shoulders 23 protrude from the outer circumferential surface of the adapter element 18 in the region of the inlet section 26a and the intermediate section 26b of the through-opening 26 extending through the adapter element 18. Such a configuration ensures that, in the region of the receiving section 26c of the through-opening 26, an air gap 68 is present between the outer circumferential surface of the adapter element 18 and the inner circumferential surface of the hollow sleeve 16 which allows an unhindered exit of gas from receiving section 26c via the radial bores 66 of the venting device 64.

Figure 12:
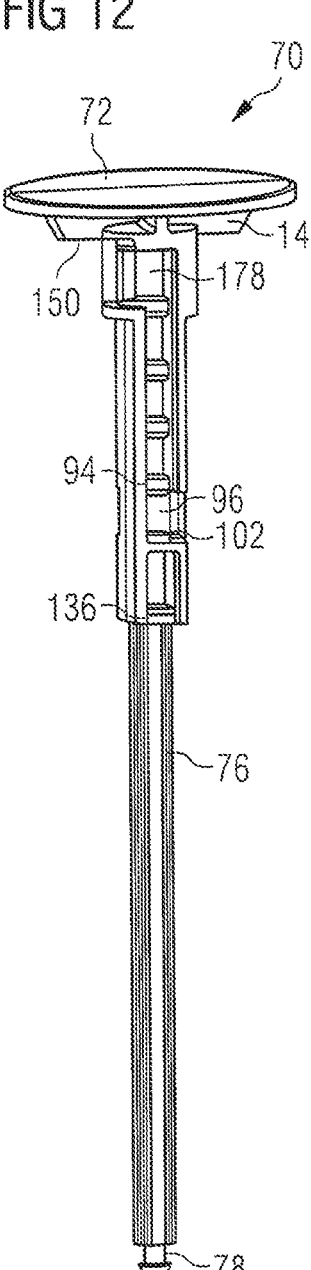
FIG. 12 shows a detailed view of the plunger of the injection device.

The injection device 10 of the injection solution transferring system 100 further comprises a plunger 70 which is depicted in greater detail in FIG. 12. In the embodiment of an injection device 10 shown in the drawings, the plunger 70 is made of polycarbonate. At least a portion of the plunger 70 is slidably received within the injection solution receptacle 30 of the injection device 10. The plunger 70 is displaceable relative to the injection solution receptacle 30 in a distal direction along a longitudinal axis of the plunger 70 in order to expel injection solution contained in the injection solution receptacle 30 of the injection device 10 from the injection solution receptacle 30. At its proximal end which protrudes from the injection solution receptacle 30 in a proximal direction, the plunger 70 carries an actuation button 72 which may be depressed by a user in order to displace the plunger 70 relative to the injection solution receptacle 30 in the distal direction along the longitudinal axis of the plunger 70.

Figure 13:
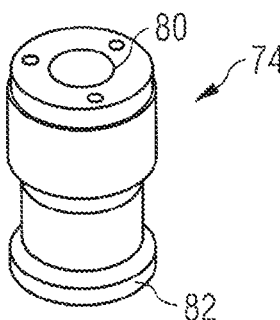
FIG. 13 shows a detailed view of a tip element of the plunger.

At its distal end, the plunger 70 is provided with a tip element 74 which is attached to a plunger rod 76, see FIG. 13. A coupling between the plunger rod 76 and the tip element 74 is effected by the interaction of a tip barb 78 provided at a distal end of the plunger rod 76 with a barb receptacle 80 of the tip element 74. Further, the tip element 74 is provided with a sealing element 82 which is provided in the region of an outer circumferential surface of the tip element 74 and which sealingly interacts with an inner circumferential surface of the injection solution receptacle 30.

Figure 14:
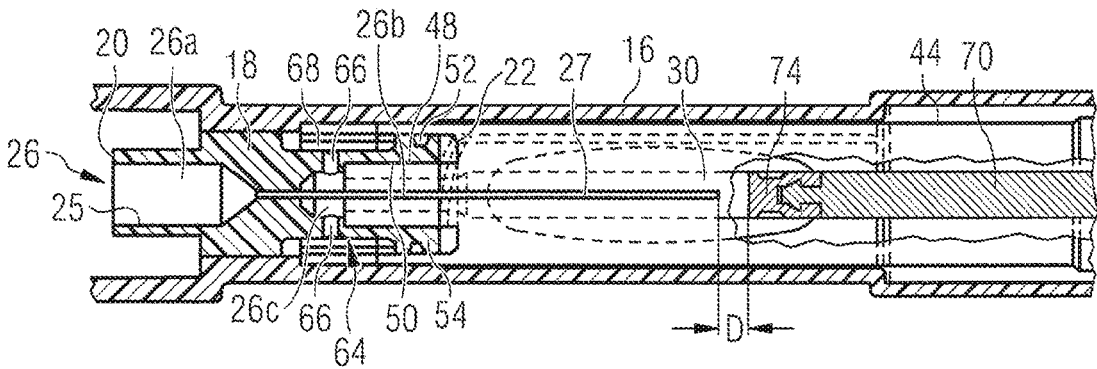
FIG. 14 shows the arrangement of the cannula of the filling adapter relative to the plunger of the injection device when the filling adapter is connected to the injection device.

The plunger 70 of the injection device 10 can be arranged in a filling position as shown in FIGS. 33a to 33d. When the plunger 70 is arranged in its filling position and the injection device 10 is engaged with the second connecting port 22 of the adapter element 18 of the filling adapter 12, a distal tip of the plunger 70, i.e. a distal end face of the tip element 74 provided at the distal tip of the plunger 70, is disposed at a desired close distance D from the distal tip of the cannula 27 of the filling adapter 12, see FIG. 14. For example, the injection device 10 and the filling adapter 12 may be designed so as to set the distance D between the distal tip of the plunger 70 and the distal tip of the cannula 27 to approximately 1.5 mm+/−0.5 mm. By arranging the distal tip of the plunger 70 and the distal tip of the cannula 27 at a close distance, the injection solution supplied to the injection solution receptacle 30 via the cannula 27 is reliably forced to flow in the direction of the venting device 64. As a result, air-free filling of the injection solution receptacle 30 with the injection solution can be ensured.

Finally, the hollow sleeve 16 is provided with two observing windows 83 for observing the filling of the injection device 10 with the injection solution from the syringe 14. The observing windows 83 allow an unhindered view of interior of the injection device 10 and the distal tip of the cannula 27.

The plunger 70 is displaceably received in a housing 84 of the injection device 10 which comprises a first housing element 86 depicted in greater detail in FIGS. 16 to 19 and a second housing element 88 depicted in greater detail in FIGS. 20 to 23. Both the first and the second housing element 86, 88 are made of polycarbonate/acrylnitril butadien styrol, but have a different colour. The first housing element 86 is provided with a plunger through-hole 90 which receives the plunger rod 76 so that the plunger 70 is displaceable in a direction along its longitudinal axis relative to the first housing element 86. Guiding elements 92 are provided on the first housing element 86 so as to protrude into the plunger through-hole 90. When the plunger 70, i.e. the plunger rod 76, is received in the plunger through-hole 90 of the first housing element 86, each guiding element 92 engages with a guiding channel 94 which provided in a circumferential surface of the plunger 70, i.e. the plunger rod 76, and which extends along the longitudinal axis of the plunger 70, see in particular FIGS. 19a and 19b.

For assembling the plunger 70 to the first housing element 86, assembly channels 96 are provided in the outer circumferential surface of the plunger rod 76 which branch of from the guiding channels 94 in a distal region thereof and extend substantially perpendicular to the guiding channels 94 in a circumferential direction of the plunger rod 76. Upon assembling the plunger 70 to the first housing element 86, the guiding elements 92 are brought into engagement with the assembly channels 96. Thereafter, the plunger 70 is rotated until the guiding elements 92 are received in the guiding channels 94 in a guiding manner, see FIGS. 19a and 19b.

In order to simplify the handling of the injection solution transferring system 100, the injection device 10 is delivered with the plunger 70 being arranged in its filling position which corresponds to a proximal end position of the plunger 70. A plunger positioning mechanism 98 prevents that the plunger 70 can be moved further in a proximal direction relative to the injection solution receptacle 30 than into its proximal end position, i.e. its filling position. The plunger positioning mechanism 98, however, allows a movement of the plunger 70 relative to the injection solution receptacle 30 from its filling position in a distal direction. Specifically, the plunger positioning mechanism 98 is defined by a distal end face 102 of the guiding channels 94 which are provided in the circumferential surface of the plunger rod 78 and the guiding elements 92 provided on the first housing element 86. When the plunger 70 is arranged in its proximal end position which corresponds to its filling position, the guiding elements 92 abut against the distal end faces 102 of the guiding channels 94. The interaction between the distal end faces 102 of the guiding channels 94 and the guiding elements 92 then prevents a further movement of the plunger 70 in the proximal direction and hence define the proximal end position, i.e. the filling position of the plunger 70.

Figure 20:
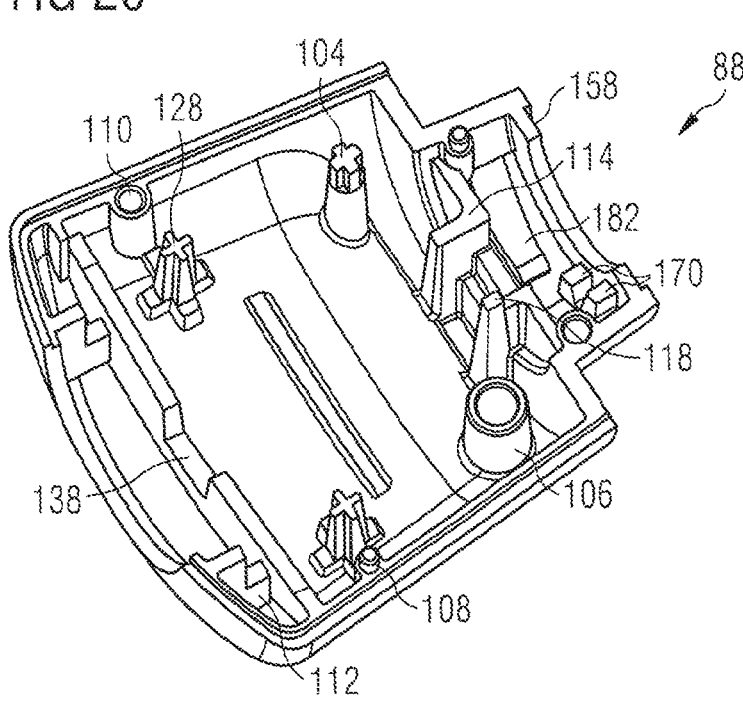
FIGS. 20 and 21 show detailed three-dimensional views of the second housing element of the injection device.
Figure 21:
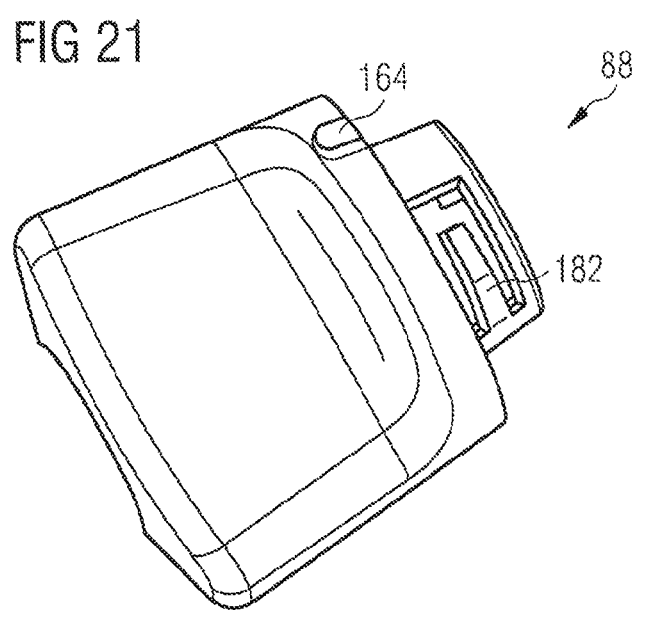
Figure 22:
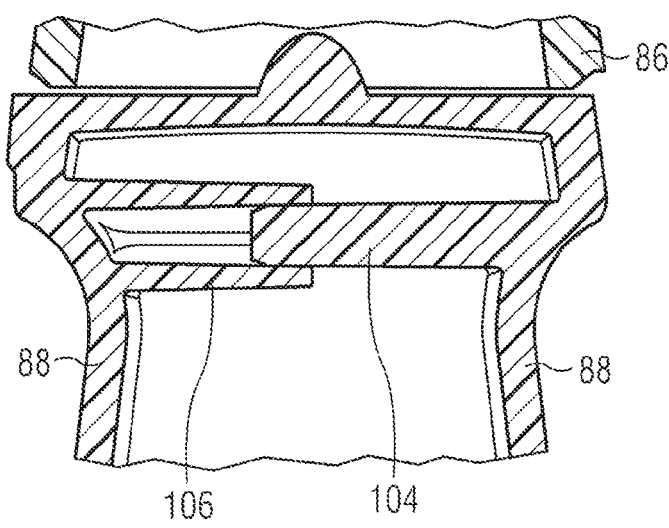
FIG. 22 shows the assembly of the second housing element.
Figure 23:
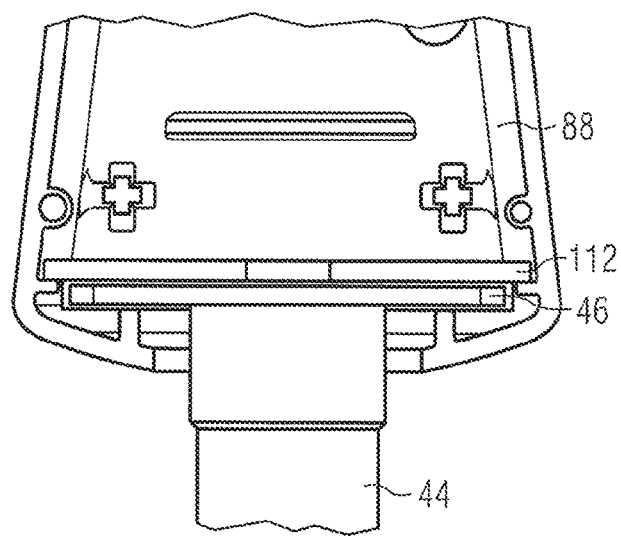
FIG. 23 shows the attachment of the injection solution receptacle to the second housing element.

The second housing element 88 comprises two identical parts, see FIGS. 20 and 21, each of which comprises an interference pin 104 and an interference receptacle 106. The two housing parts of the second housing element 88 are assembled by bringing the interference pins 104 into engagement with the respective interference receptacles 106 as shown in FIG. 22. For aligning the parts of the second housing element 88 relative to each other upon assembly, alignment pins 108 are provided which, upon connecting the parts of the second housing element 88, are received in respective alignment receptacles 110. The injection solution receptacle 30 and the protective outer barrel 44 are connected to the second housing element 88 via the flange element 46 which extends from the outer barrel 44 at a proximal end thereof. Specifically, the flange elements 46 is received in a suitably shaped and dimensioned receptacle 112 of the second housing element 88, see FIG. 23.

Figure 26:
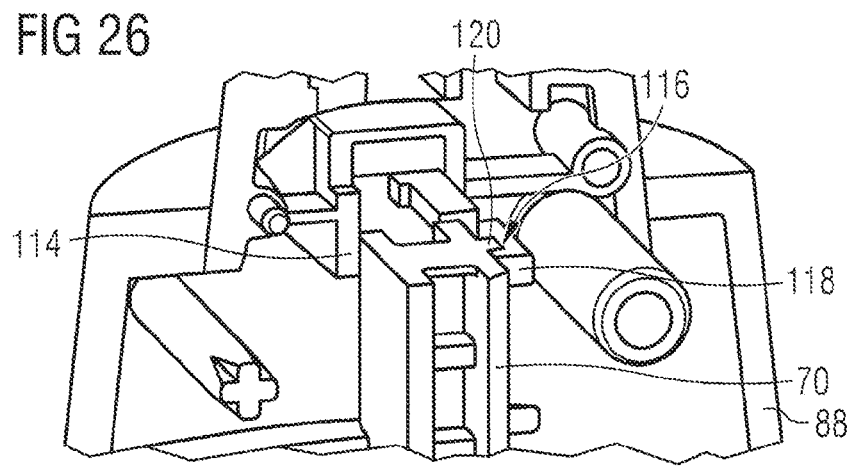
FIG. 26 shows the interaction between the plunger and the second housing element.

As shown in particular in FIG. 26, the second housing element 88 is provided with a plunger guide 114 which constrains the plunger rod 76 so that the plunger 70 is prevented from rotating relative to the second housing element 88. A first drag mechanism 116 is adapted to exert a retaining force which retains the plunger 70 in its current position relative to second housing element 88. The first drag mechanism 116 thus prevents an unintentional displacement of the plunger 70 relative to the injection solution receptacle 30 so that active manual actuation of the plunger 70, for example by the application of a pressing force to the actuation button 72, is necessary for displacing the plunger 70 relative to the injection solution receptacle 30. The first drag mechanism 116 comprises a resilient drag element 118 which is provided on the second housing element 88. The resilient drag element 118 exerts a resilient retaining force on the plunger 70, i.e. the resilient drag element 118 is resiliently urged out of a rest position into a biasing position by an interaction with the plunger 70 and, due to its resiliency, applies a resilient reaction force on the plunger 70 which retains the plunger 70 in its current position. Specifically, the resilient drag element 118 interacts with a drag rib 120 which is provided on the outer circumferential surface of the plunger rod 76 and which extends substantially parallel to the longitudinal axis of the plunger 70.

The injection device 10 further comprises a plunger locking mechanism 122 which interacts with the filling adapter 12, i.e. the hollow sleeve 16 of the filling adapter 12, so as to prevent the plunger 70 of the injection device 10 from being moved from its filling position relative to the injection solution receptacle 30 in a distal direction, i.e. in the direction of the distal tip of the cannula 27, when the injection device 10 is connected to the filling adapter 12. The plunger locking mechanism 122 serves to prevent an inadvertent contact between the plunger 70, i.e. the distal tip of the plunger 70, and the distal tip of the cannula 27. The functioning of the plunger locking mechanism 122 now will be described in greater detail with reference to FIGS. 27 to 32.

Figure 27:
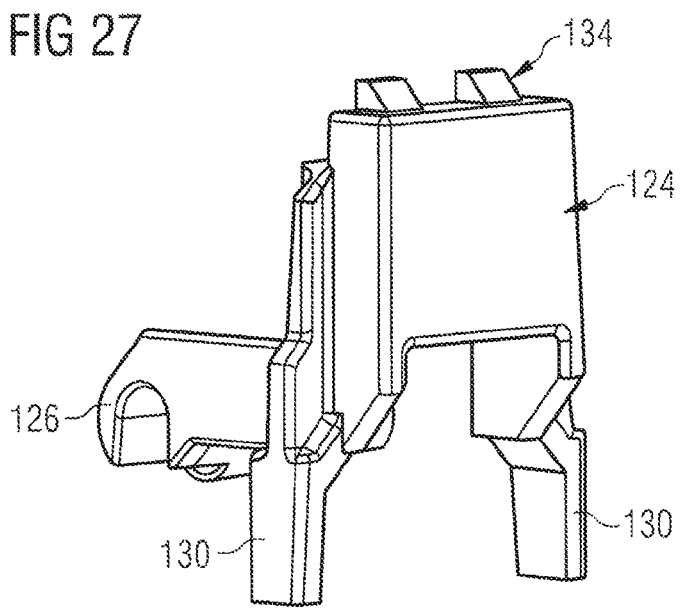
FIGS. 27 and 28 show detailed three-dimensional views of a lever element of a plunger locking mechanism which prevents the plunger of the injection device from being moved from a filling position in a distal direction when the injection device is connected to the filling adapter.
Figure 28:
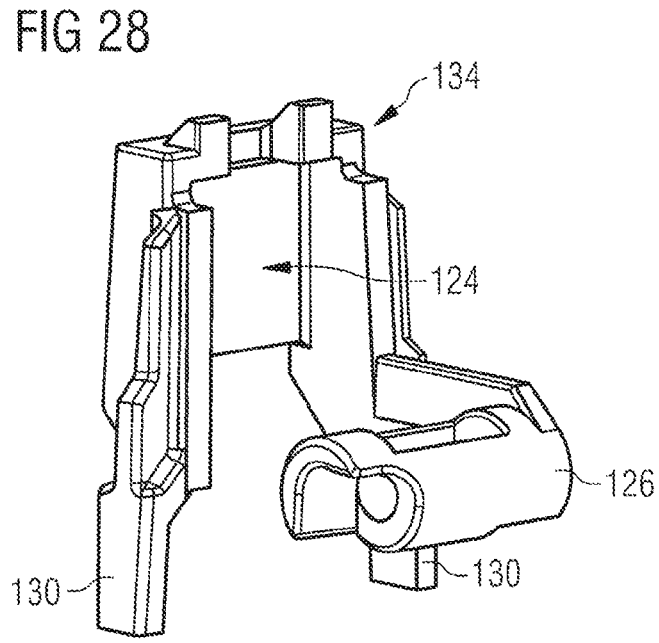
Figure 29:
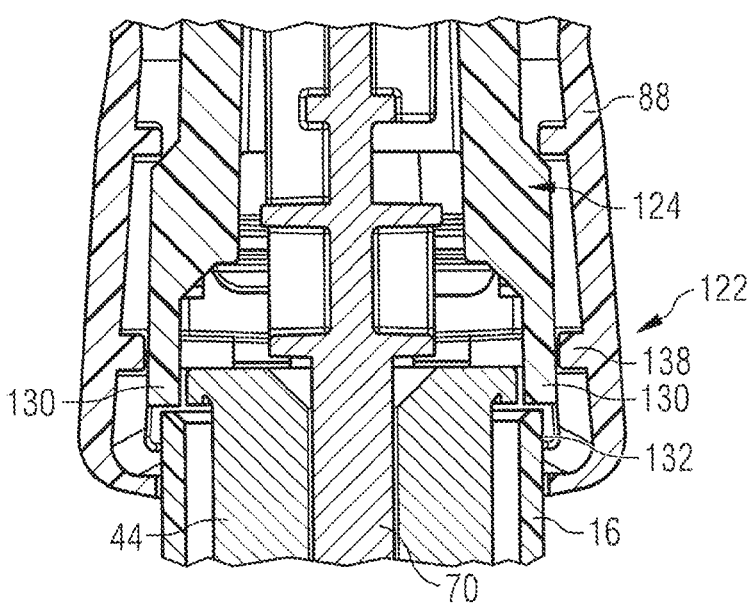
FIG. 29 shows the lever element of the plunger locking mechanism in an active position.
Figure 30:
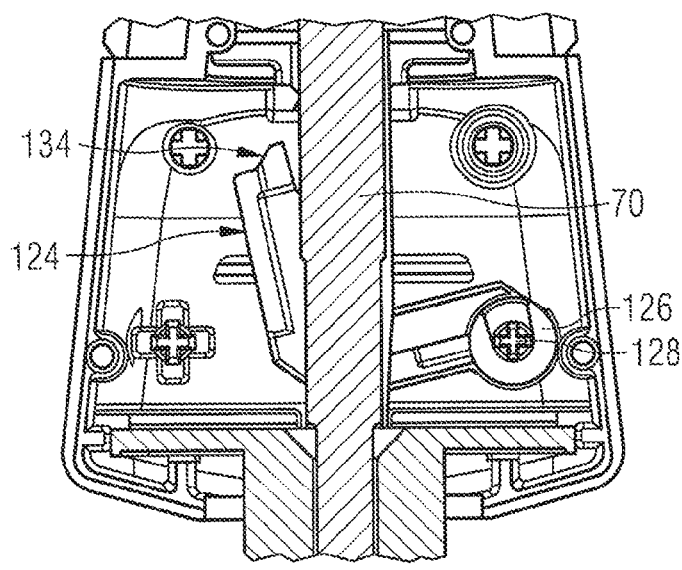
FIG. 30 shows the lever element of the plunger locking mechanism in an inactive position.
Figure 31:
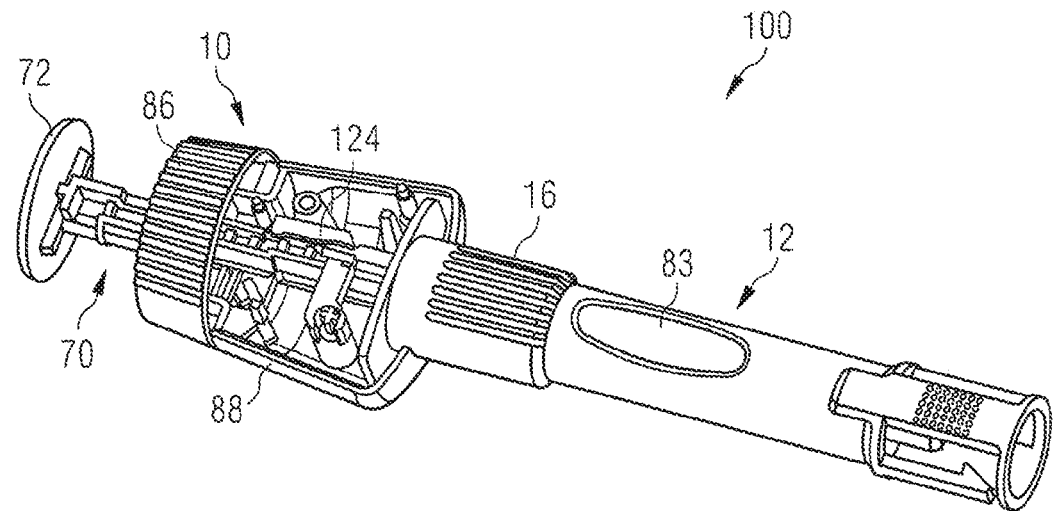
FIG. 31 shows the injection solution transferring system with the filling adapter being connected to the injection device, with one part of the second housing element removed and with the lever element of the plunger locking mechanism in its active position.

Specifically, the plunger locking mechanism 122 comprises a lever element 124, see FIGS. 27 and 28, which is displaceable within the second housing element 88 between an active position which is depicted in FIGS. 29 and 31 and an inactive position depicted in FIG. 30. When being arranged in its active position, the lever element 124 interacts with the plunger 70 and the hollow sleeve 16 of the filling adapter 12 so as to prevent the plunger 70 from being moved from its filling position in a distal direction when the injection device 10 is connected to the filling adapter 12. To the contrary, when being arranged in its inactive position, the lever element 124 allows a movement of the plunger 70 from its filling position in a distal direction when the injection device 10 is not connected to the filling adapter 12. The lever element 124 is mounted within the second housing element 88 so as to be rotatable between its active position and its inactive position. Specifically, the lever element 124 is provided with a hinge 126 which rotatably attaches the lever element 124 to a rotational axis 128 provided on the second housing element 88.

The lever element 124 further comprises a pair of foot elements 130 which extend substantially parallel to each other and which are contacted by the filling adapter 12 when the injection device 10 is connected to the filling adapter 12, in order to maintain the lever element 124 in its active position. In particular, as shown in FIG. 29, the foot elements 130 face the filling adapter 12 and are contacted by a locking rim 132 of the hollow sleeve 16 which faces the injection device 10 when the injection device 10 is connected to the filling adapter 12. Due to the interaction between the locking rim 132 of the hollow sleeve 16 and the foot elements 130, the lever element 124 is pushed in a proximal direction substantially parallel to the longitudinal axis of the plunger 70 into contact with the plunger 70 and thus held in its active position shown in FIGS. 29 and 31.

The lever element 124 comprises a stop device 134 which comprises two tabs extending from a proximal end face of the lever element 124. Further, a proximal portion of the plunger 70 extends further in a direction substantially perpendicular to the longitudinal axis of the plunger 70 than a distal portion of the plunger 70. As a result, a shoulder which defines an abutment surface 136 is formed in a transition region between the distal portion and the proximal portion of the plunger 70. Specifically, the abutment surface 136 is defined by an outer portion of a distal end face of the proximal plunger portion which protrudes from an outer circumferential surface of the distal plunger portion. When the lever element 124 is arranged in its active position as shown in FIG. 29, the two tabs of the stop device 134 abut against the abutment surface 136 of the plunger 70. As a result, the lever element 124 is held in its active position and, simultaneously, movement of the plunger 70 from its filling position in a distal direction is prevented.

Figure 32:
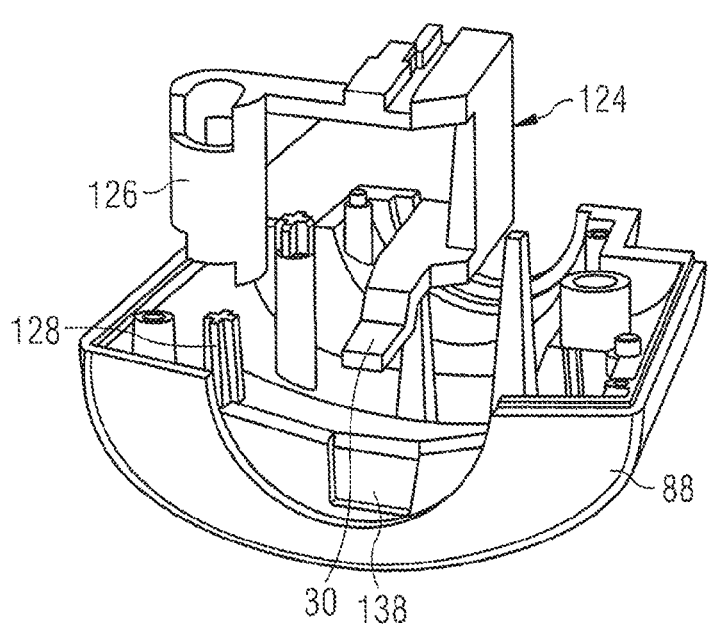
FIG. 32 shows the assembly of the lever element of the plunger locking mechanism in the second housing element.

The plunger locking mechanism 122 also comprises a retention device 138 which interacts with the foot elements 130 of the lever element 124, in order to prevent that the foot elements 130 disengage from locking rim 132 of the filling adapter 12 when the lever element 124, by the interaction between the locking rim 132 and the foot elements 130, is maintained in its active position, see FIGS. 20 and 32. In particular, the retention device 138 prevents that the foot elements 130 slip around the locking rim 132 of the hollow sleeve 16 and hence disengages from the filling adapter 12 when the lever element 124 is pushed into engagement with the plunger 70. The retention device is provided in the second housing element 88 and is designed in the form of a retention rib which prevents that the foot elements 130 of the lever element 124 deform away from the plunger 70 in a direction substantially perpendicular to the longitudinal axis of the plunger 70.

After completion of the transfer of the injection solution from the syringe 14 to the injection solution receptacle 30 of the injection device 10 with the plunger 70 being arranged in its filling position as described above and as shown in FIGS. 33a to 33c, the filling adapter 12 and the syringe 14 are detached from the injection device 10 by disengaging the male Luer taper 48 provided at the distal end of the injection solution receptacle 30 from the female Luer taper 50 provided on the second connecting port 22 of the adapter element 18 and by disengaging the Luer thread 52 provided at the distal end of the outer barrel 44 from the complementary Luer thread 54 provided at the second connecting port 22, see FIG. 33d.

As soon as the filling adapter 12 is detached from the injection device 10, the filling adapter 12, i.e. the locking rim 132 of the hollow sleeve 16, no longer contacts the foot elements 130 of the lever element 124. Hence, when a pressing force is applied to the plunger 70 so as to displace the plunger 70 in a distal direction within the injection solution receptacle 30 of the injection device 10, the lever element 124 is displaced into its inactive position shown in FIG. 30. In particular, the lever element 124 is rotated around its rotational axis 128 from its active position into its inactive position and hence out of the way of the plunger 70. As a result, the displacement of the plunger 70 is no longer hindered. Consequently, a needle (not shown in the drawings) can be attached to the injection device 10, for example with the aid of the Luer thread 52 provided at the distal end of the outer barrel 44 and injection device 10 can be operated as will be described further below.

For administering an accurate dose, in particular an accurate micro dose of, for example, 10 μL of the injection solution received within the injection solution receptacle 30 to a patient, in a first step, excess injection solution has to be expelled from the injection solution receptacle 30 by displacing the plunger 70 relative to the injection solution receptacle 30 in the distal direction as shown in FIG. 34a. Thereafter, the desired to dose of the injection solution has to be injected into the patient.

Figure 34:
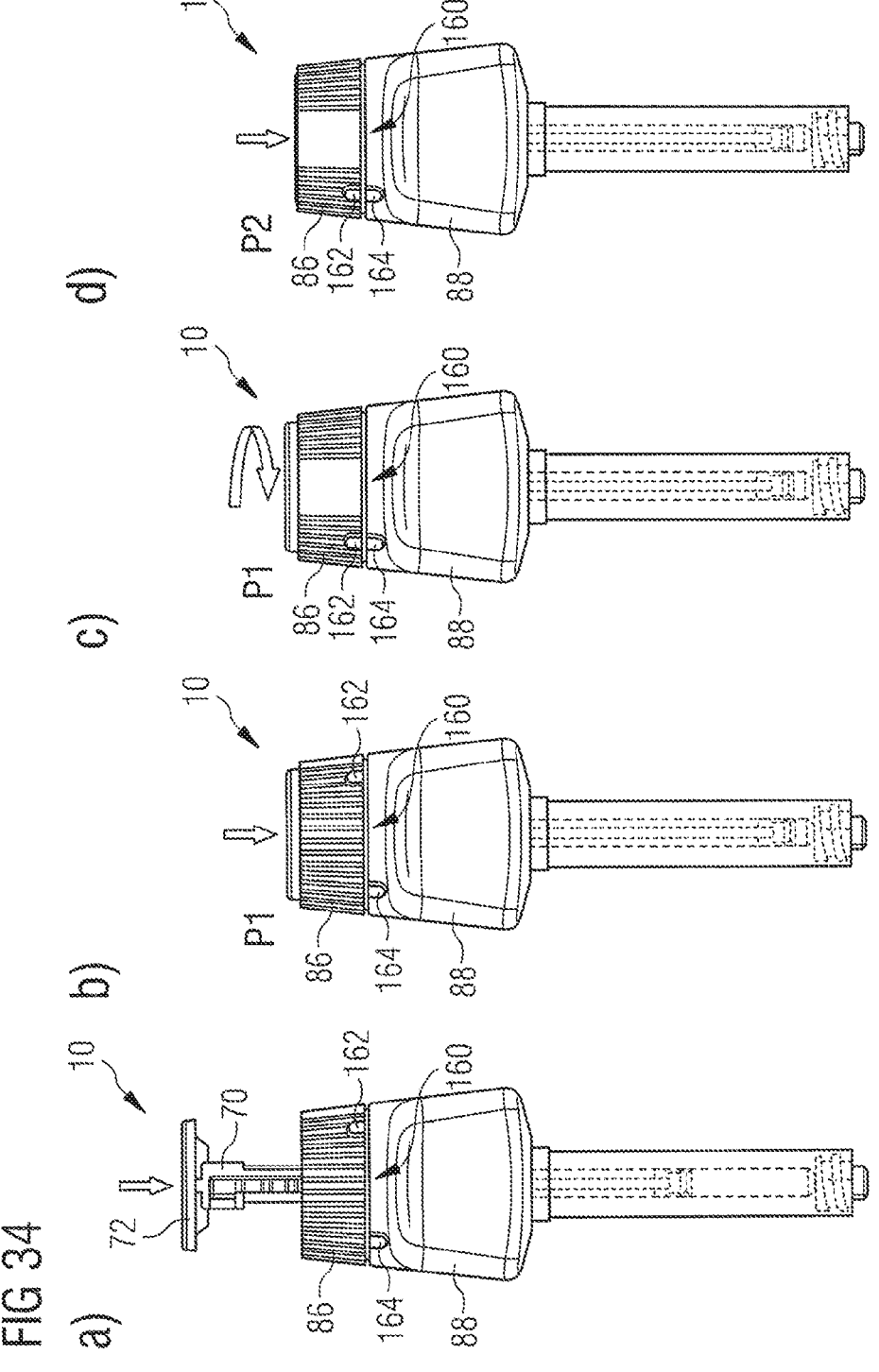
FIGS. 34a to 34d show the use of the injection device upon administering an injection solution to a patient.

The injection device 10 therefore comprises a first plunger stop mechanism 140 which is adapted to stop a displacement of the plunger 70 relative to the injection solution receptacle 30 in the distal direction at a first dosing position P1, see FIG. 34. Further, the injection device 10 comprises a second plunger stop mechanism 142 which is adapted to stop a displacement of the plunger 70 relative to the injection solution receptacle 30 from the first dosing position P1 in the distal direction at a second dosing position P2, see FIG. 34*d*. The first and the second dosing position P1, P2 of the plunger 70 are selected in such a manner that the plunger 70, upon being displaced relative to the injection solution receptacle 30 between the first and the second dosing position P1, P2 is adapted to expel a desired dose of the injection solution contained in the injection solution receptacle 30 from the injection solution receptacle 30.

Thus, during use of the injection device 10, a user can expel excess injection solution from the injection solution receptacle 30 by displacing the plunger 70 relative to the injection solution receptacle 30 in the distal direction until the plunger 70 reaches the first dosing position P1. Upon reaching the first dosing position P1, the first plunger stop mechanism 140 stops further displacement of the plunger 70 in the distal direction. Consequently, the user is prevented from expelling too much injection solution from the injection solution receptacle. The residual injection solution contained in the injection solution receptacle can then be administered to a patient by further displacing the plunger 70 in the distal direction until the plunger 70 reaches the second dosing position P2. Upon reaching the second dosing position P2, the second plunger stop mechanism 142 stops further displacement of the plunger 70 in the distal direction and hence prevents that too much injection solution is administered to the patient.

Figure 16:
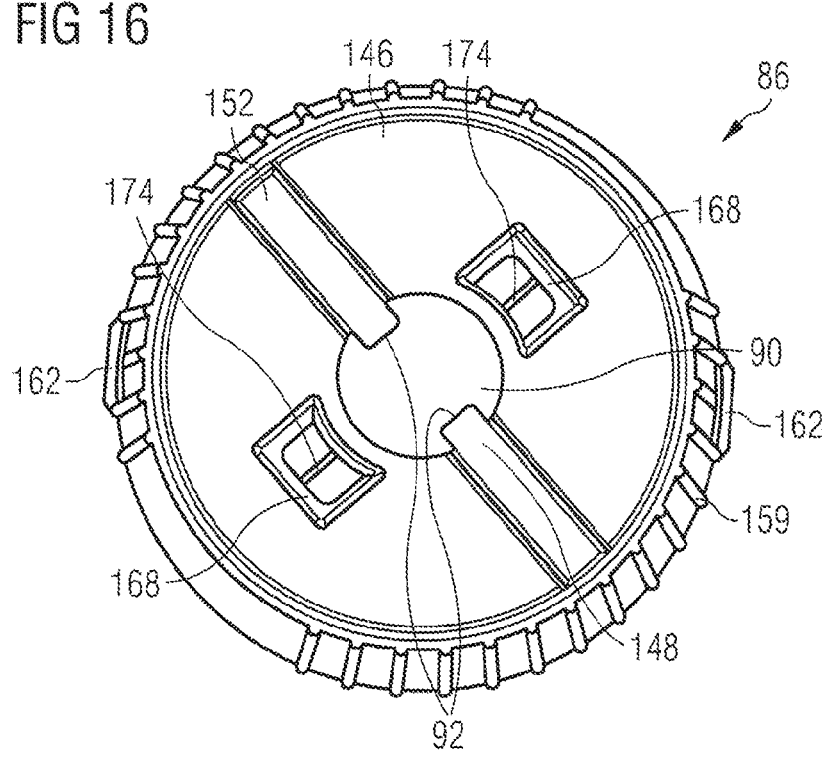
FIGS. 16 to 18 show detailed three-dimensional views of a first housing element of the injection device.
Figure 18:
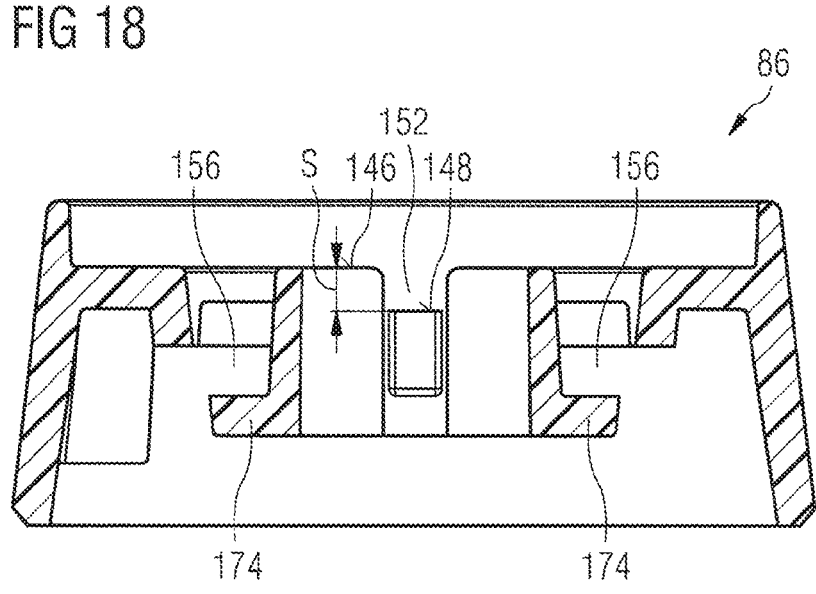

As shown in particular in FIGS. 12, 16 and 18, the first plunger stop mechanism 140 comprises a dosing element 144 which is attached to the plunger 70 and which is adapted to abut against a first dosing surface 146 provided on the first housing element 86. The dosing element 144 also forms a part of the second plunger stop mechanism 142 and, as a part of the second plunger stop mechanism 142, is adapted to abut against a second dosing surface 148 which is also provided on the first housing element 86. The dosing element 144 is formed integral with the plunger 70 and is designed in the form of a rib protrudes from a lower surface of the actuation button 72 in the direction of the inner injection solution receptacle 30.

The first and the second dosing surface 146, 148 extend substantially parallel to each other and parallel to an abutting surface 150 of the dosing element 144 substantially perpendicular to the longitudinal axis of the plunger 70, wherein the second dosing surface 148 is arranged parallel offset relative to the first dosing surface 146 in the distal direction. A distance S between the first and the second dosing surface 146, 148 in the distal direction corresponds to a desired travel distance of the plunger 70 in the distal direction between the first and the second dosing position P1, P2, see in particular FIG. 18. Hence, the distance S between the first and the second dosing surface 146, 148 in the distal direction sets the desired injection solution dose to be expelled from the injection solution receptacle 30 upon displacing the plunger 70 from the first to the second dosing position P1, P2.

Further, the first and the second dosing surface 146, 148 are arranged offset relative to each other in a circumferential direction of the plunger 70. Specifically, the second dosing surface 148 is defined by a bottom surface of a recess 152 formed in the first dosing surface 146 provided on the first housing element 86.

When the plunger 70, during use of the injection device 10, is moved from its filling position shown in FIG. 34*a* in the distal direction, the abutting surface 150 of the dosing element 144 abuts against the first dosing surface 146 when the plunger 70 reaches the first dosing position P1 as depicted in FIG. 34*b*. The interaction of the dosing element 144 with the first dosing surface 146 prevents the plunger from being displaced further in the distal direction. Hence, the first plunger stop mechanism 140 provides a hard stop for the plunger 70 at the first dosing position P1. The injection device 10 therefore further comprises a plunger releasing mechanism 154 which is adapted to deactivate the first plunger stop mechanism 140 in order to release the plunger 70 and to thus allow a displacement of the plunger 70 relative to the injection solution receptacle 30 from the first dosing position P1 in the distal direction, i.e. in the direction of the second dosing position P2.

The plunger releasing mechanism 154 is adapted to allow a movement of the first dosing surface 146 relative to the dosing element 144, i.e. relative to the plunger 70, in order to disengage the dosing element 144 from the first dosing surface 146. Specifically, the plunger releasing mechanism 154 is adapted to allow a rotational movement of the first dosing surface 146 relative to the dosing element 144, i.e. relative to the plunger 70, in order to disengage the dosing element 144 from the first dosing surface 146. In order to effect the rotational movement of the first dosing surface 146 relative to the dosing element 144, the first housing element 86 which carries the first and the second dosing surface 146, 148 is designed so as to be manually rotatable relative to the second housing element 88, see FIG. 34*c*. Since the plunger 70 is prevented from rotating relative to the second housing element 88 by means of the plunger guide 114, a rotation of the first housing element 86 relative to the second housing element 88 inevitably results in a rotation of the first housing element 86 relative to the plunger 70.

Figure 17:
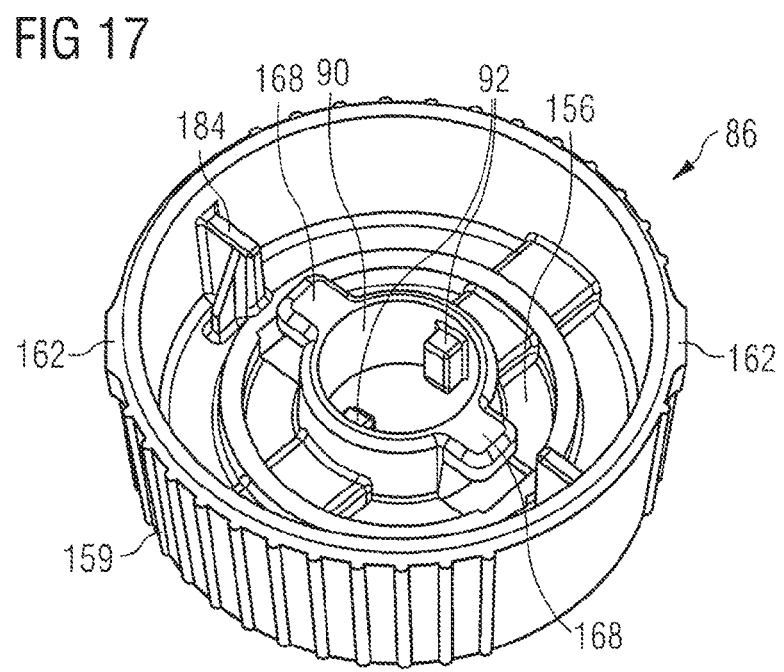
Figure 24:
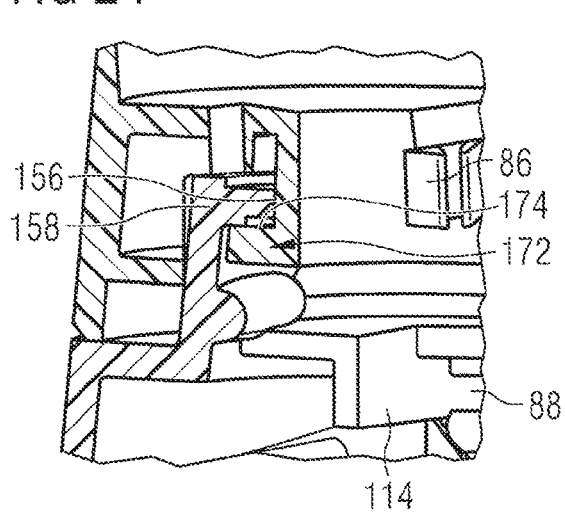
FIGS. 24 and 25 show the interaction between the first and the second housing element.

In order to be rotatable relative to the second housing element 88 in a guided manner, the first housing element 86 is provided with a retaining recess 156, see FIGS. 17, 18 and 24, which receives a retaining element 158 formed on the second housing element 88, see FIG. 20. Further, in order to simplify the handling of the plunger releasing mechanism 154, the first housing element 86, in the region of its outer surface, is provided with a gripping structure 159. The gripping structure 159 is designed in the form of a gripping rib array with individual gripping ribs extending substantially in a direction along the longitudinal axis of the plunger 70.

The rotation amount of the first housing element 86 relative to the second housing element 88 and hence relative to the plunger 70 is set such that the recess 152 formed in the first dosing surface 146 is brought into alignment with the dosing element 144 protruding from the actuation button 72 of the plunger 70. The plunger releasing mechanism 154 thus is adapted to displace the first and the second dosing surface 146, 148 in the circumferential direction of the plunger 70, in order to disengage the dosing element 144 from the first dosing surface 146 and to simultaneously align the second dosing surface 148 with the dosing element 144.

In order to ensure that a user, upon activating the plunger releasing mechanism 154, rotates the first housing element 86 relative to the second housing element 88 and the correct direction and by the correct rotation amount that is necessary to disengage the dosing element 144 from the first dosing surface 146 and to simultaneously align the second dosing surface 148 with the dosing element 144, the plunger releasing mechanism 154 comprises a marker system 160 which is adapted to indicate an activation of the plunger releasing mechanism 154. The marker system 160 comprises a first marker element 162 which is provided on an outer surface of the first housing element 86. The marker system 160 further comprises a second marker element 164 which is provided on an outer surface of the second housing element 88. The first and the second marker element 162, 164 are arranged on the first and the second housing element 86, 88 in such a position that they are positioned offset relative to each other a circumferential direction of the plunger 70, when the plunger release mechanism 154 is not activated, but positioned in alignment with each other, when the plunger release mechanism 154 is activated, compare FIGS. 34*b* and 34*c*.

The injection device 10 further comprises a limiting mechanism 166 which is adapted to limit the movement of the first and the second dosing surface 146, 148 for disengaging the dosing element 144 from the first dosing surface 146 and for aligning the dosing element 144 with the second dosing surface 146, see FIGS. 16 and 20. The limiting mechanism 166 comprises a first limiting element 168 which is provided on the first housing element 86 carrying the first and the second dosing surface 146, 148. Further, the limiting mechanism 166 comprises a second limiting element 170 which is provided on the second housing element 88 which remains stationary when the first housing element 86 is rotated in order to deactivate the first plunger stop mechanism 140. The first limiting element 168 abuts against the second limiting element 170 when the dosing element 144, due to the rotation of the first housing element 86 relative to plunger 70, is disengaged from the first dosing surface 146 and aligned with the second dosing surface 148. The limiting mechanism 166 prevents a user of the injection device 10 from excessively rotating the first housing element 86 relative to the second housing element 88. Further, the limiting mechanism 166 provides an haptic feedback to the user that the first plunger stop mechanism 140 has been deactivated.

A second drag mechanism 172 serves to exert a retaining force which retains the first housing element 86 in its current position relative to the second housing element 88. Due to the presence of the second drag mechanism 172, active manual actuation is necessary for rotating the first housing element 86 relative to the second housing element 88. The second drag mechanism 172 thus prevents an unintentional displacement of the first housing element 86 relative to the second housing element 88 and hence an unintentional activation of the plunger releasing mechanism 154. The second drag mechanism 172 comprises a friction element 174 which is provided on the first limiting element 168 of the limiting mechanism 166 and which is adapted to frictionally interact with the retaining element 158 of the second housing element 88.

Figure 19A:
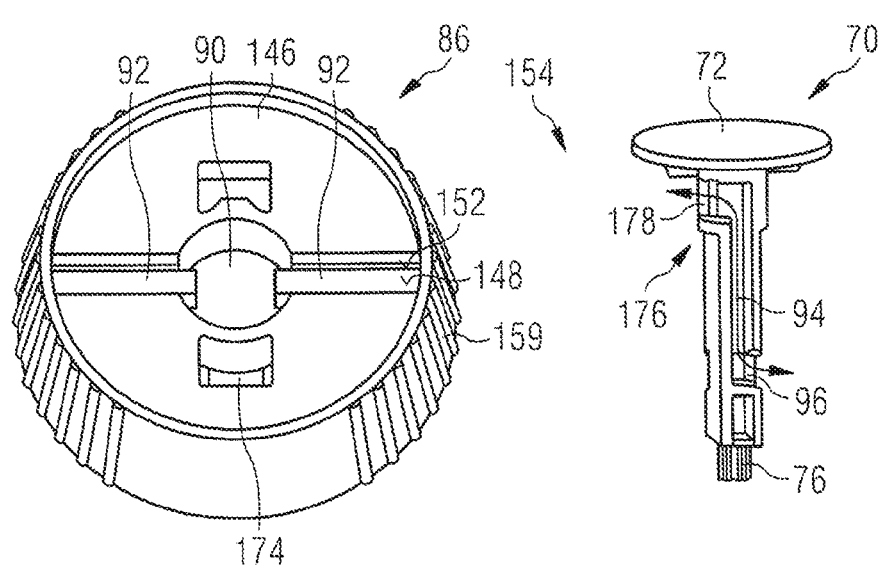
FIGS. 19a and 19b show the interaction between the plunger and the first housing element.
Figure 19B:
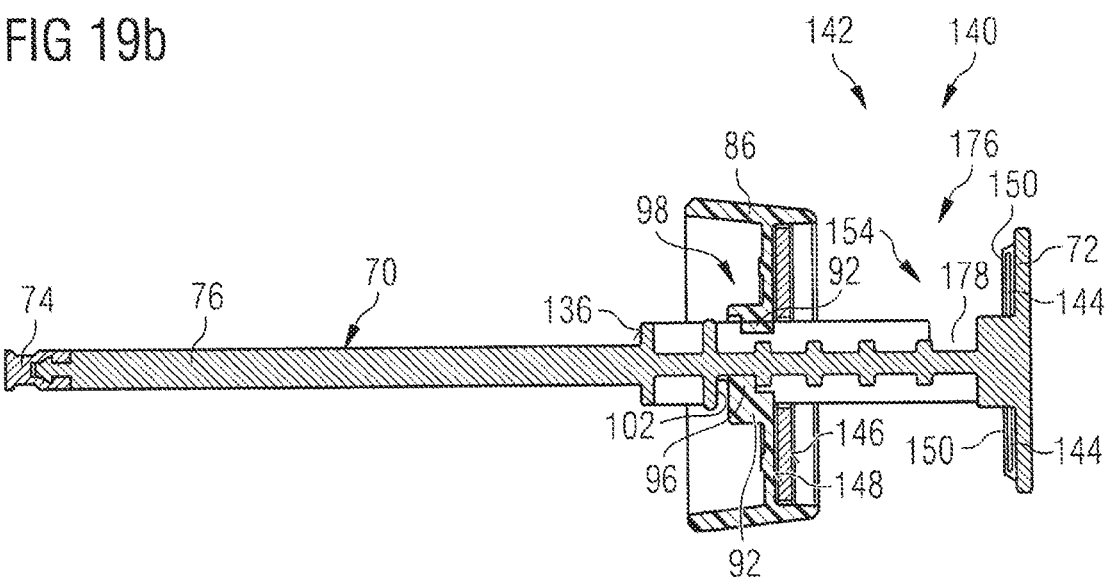

The injection device 10 further comprises an activation mechanism 176 which is adapted to prevent an activation of the plunger releasing mechanism 154 unless the plunger 70 is arranged at the first dosing position P1 and which is adapted to allow an activation of the plunger releasing mechanism 154 when the plunger 70 is arranged at the first dosing position P1 see FIGS. 12, 16 and 19*a*. Specifically, the activation mechanism 176 prevents a rotation of the first housing element 86 relative to the plunger 70 and hence prevents a movement of the dosing element 144 and the first dosing surface 146 relative to each other unless the plunger 70 is arranged at the first dosing position P1.

The activation mechanism 176 comprises the guiding channel 94 which is provided on the circumferential surface of the plunger 70, which extends along the longitudinal axis of the plunger 70 and which receives the guiding element 92 provided on the first housing element 86 in such a manner that the guiding channel 94, upon displacement of the plunger 70 relative to the injection solution receptacle 30, is displaced relative to the guiding element 92. An interaction between the guiding element 92 and opposing side surfaces of the guiding channel 94 prevents a rotation of the plunger 70 and the first housing element 86 relative to each other. The activation mechanism 176 thus fulfills the double function to provide for a guided displacement of the plunger 70 in the direction of its longitudinal axis on the one hand and to simultaneously prevent an unintentional deactivation of the first plunger stop mechanism 154 when the plunger 70 is not arranged at the first dosing position.

The activation mechanism 176 further comprises an activation channel 178 which branches off from the guiding channel 94 and extends in a circumferential direction of the plunger 70 substantially perpendicular to the guiding channel 94. The activation channel 178 receives the guiding element 92 when the plunger 70 is arranged at the first dosing position P1 and the first housing element 86 is rotated relative to the plunger 70. Hence, the first dosing position P1 of the plunger 70 is defined by the position of the activation channel 178 along the longitudinal axis of the plunger 70.

Figure 25:
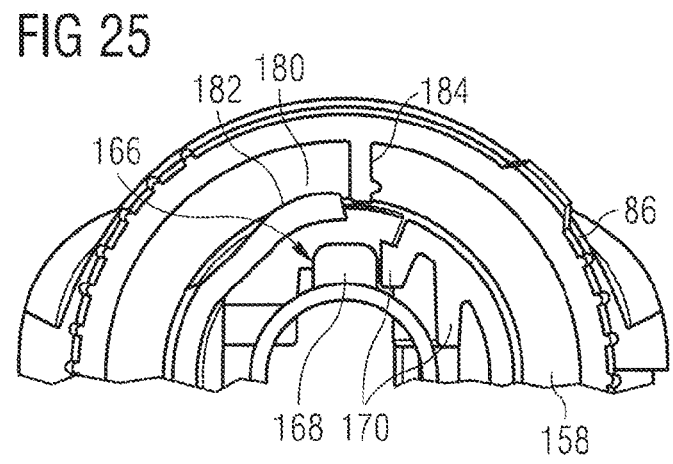

Finally, the plunger release mechanism 154 further comprises a locking arrangement 180 which locks the first dosing surface 146 in its position relative to the dosing element 144 after the first dosing surface 146 has been moved relative to the dosing element 144 in order to become disengaged from the dosing element 144, see FIGS. 17, 21 and 25. Specifically, the locking arrangement 180 comprises a resilient locking clip 182 which is provided on the second housing element 88 and which is resiliently urged out of a rest position by the interaction with a locking element 184 provided on the first housing element 86 when the first dosing surface 146 is moved relative to the dosing element 144 so as to become disengaged from the dosing element 144, i.e. when the first housing element 86 is rotated relative to the second housing element 88.

The locking clip 182 deforms back into its rest position after completion of the movement of the first dosing surface 146, i.e. after completion of the rotation of the first housing element 86, and interacts with the locking element 184 so as to lock the first housing element 86 relative to the second housing element 88 and the plunger 70. In particular, the locking clip 182 interacts with the locking element 184 so as to prevent a counter rotation of the first housing element 86 relative to the second housing element 88 and the plunger 70, after the first housing element 86 has been rotated once in order to disengage the first dosing surface 146 from the dosing element 144 and to align the second dosing surface 148 with the dosing element 144. Consequently, the first dosing surface 146 is locked in its position relative to the dosing element 144. The locking arrangement 180 allows the plunger release mechanism 154 to be used only once for deactivating the first plunger stop mechanism 140. As a result, reuse of the injection device 10 is prevented.

After completion of the rotational movement of the first housing element 86 relative to the second housing element 88 with the plunger 70 being arranged in its first dosing position P1, the dosing element 144 is aligned with the recess 152 formed in the first dosing surface 146. Consequently, the abutting surface 150 of the dosing element 144 is arranged parallel to the second dosing surface 148 at the distance S. As a result, the plunger 70 can further be displaced from the first dosing position P1 in the distal direction by the distance S into the second dosing position P2, until the dosing element 144, i.e. its abutting surface 150 abuts against the second dosing surface 148, compare FIGS. 34*c* and 34*d*. Like the first plunger stop mechanism 140, also the second plunger stop mechanism 142 provides a hard stop for the plunger 70, i.e. prevents the plunger 70 from being displaced relative to the injection solution receptacle 30 from the second dosing position P2 in the distal direction. The dose of the injection solution to be administered to a patient can thus be set in a particularly accurate manner.

Figure 35A:
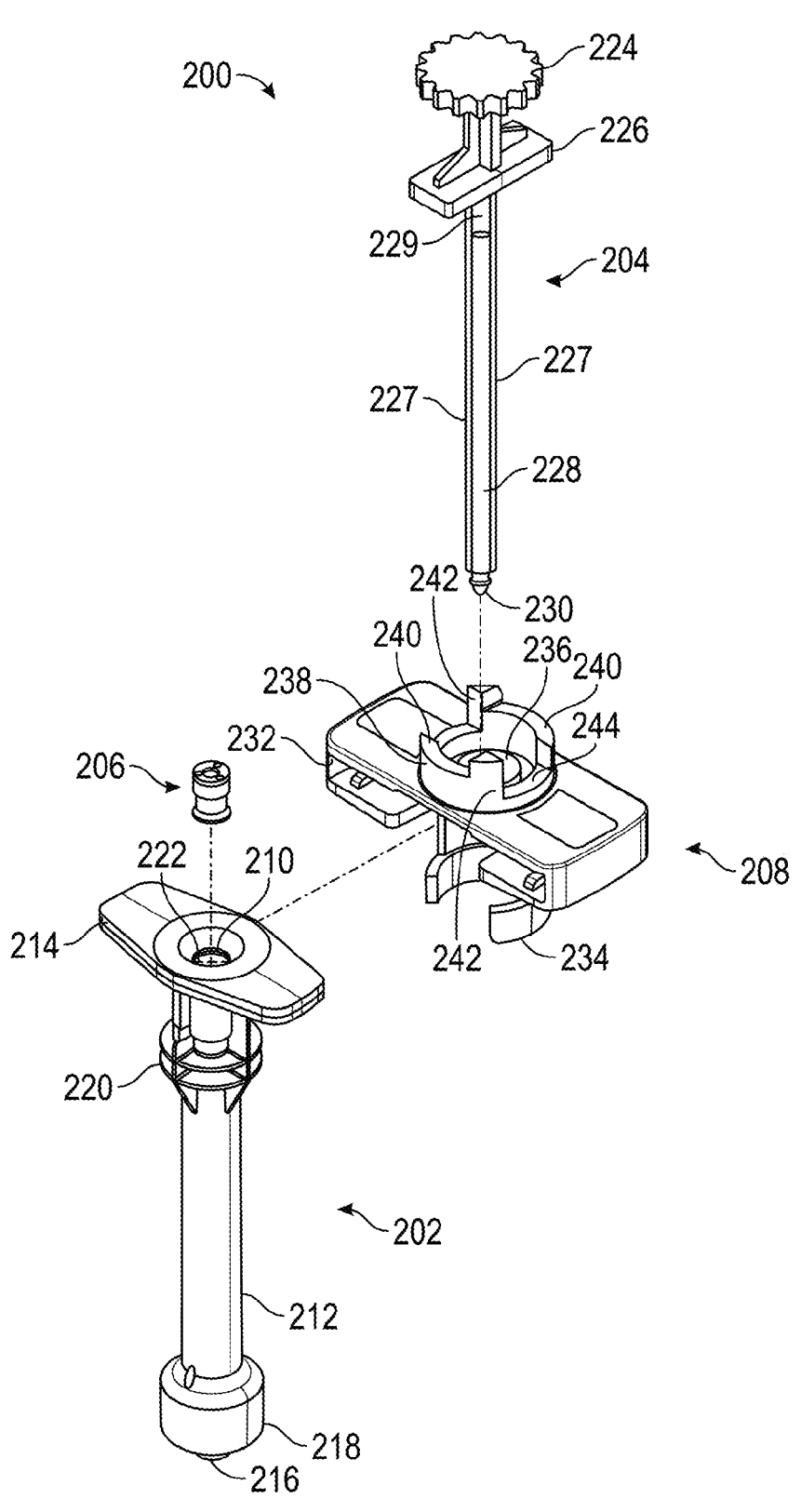
FIGS. 35a to 35c show an exploded view of an injection device, according to various examples.
Figure 35B:
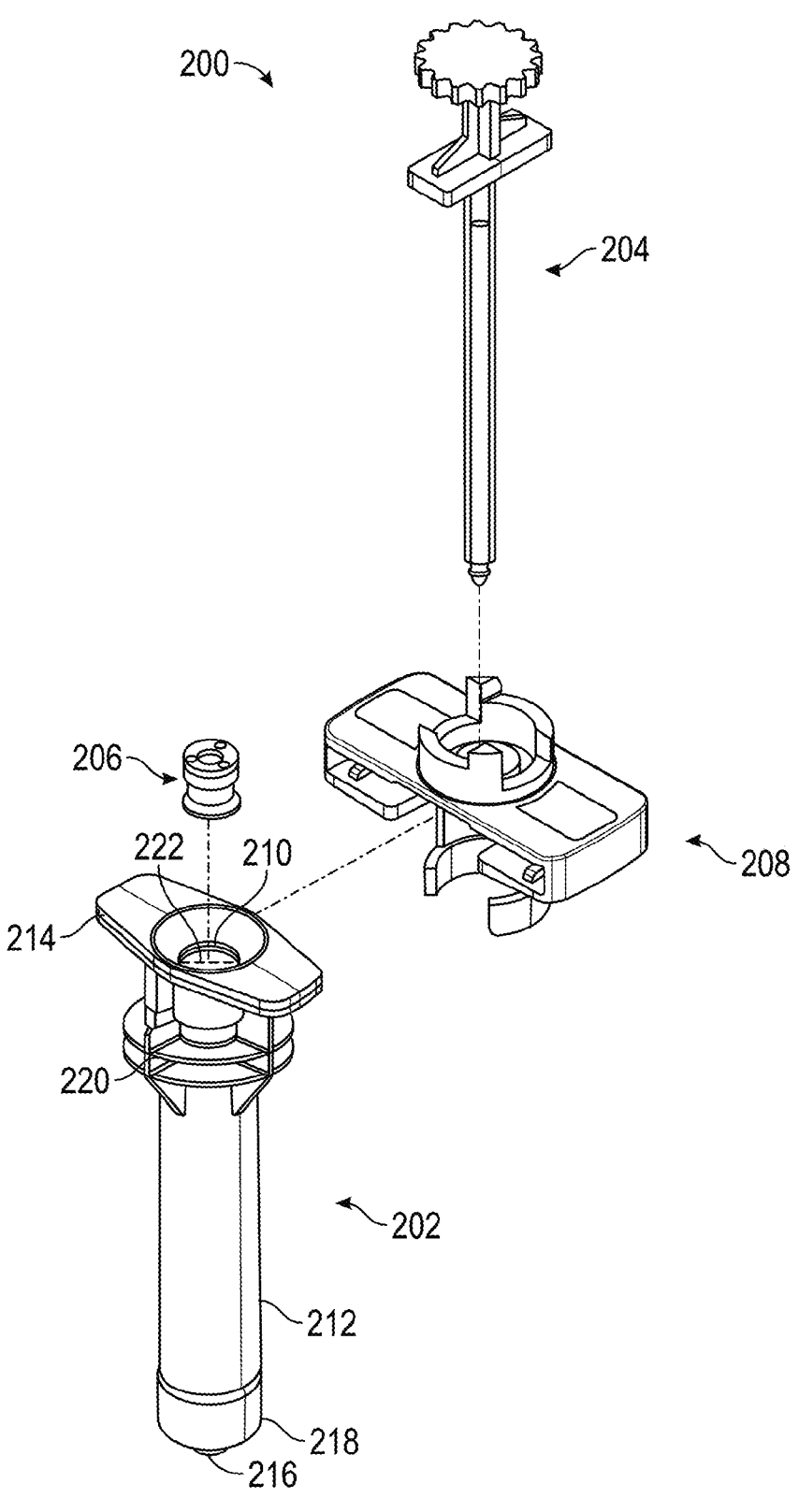
Figure 35C:
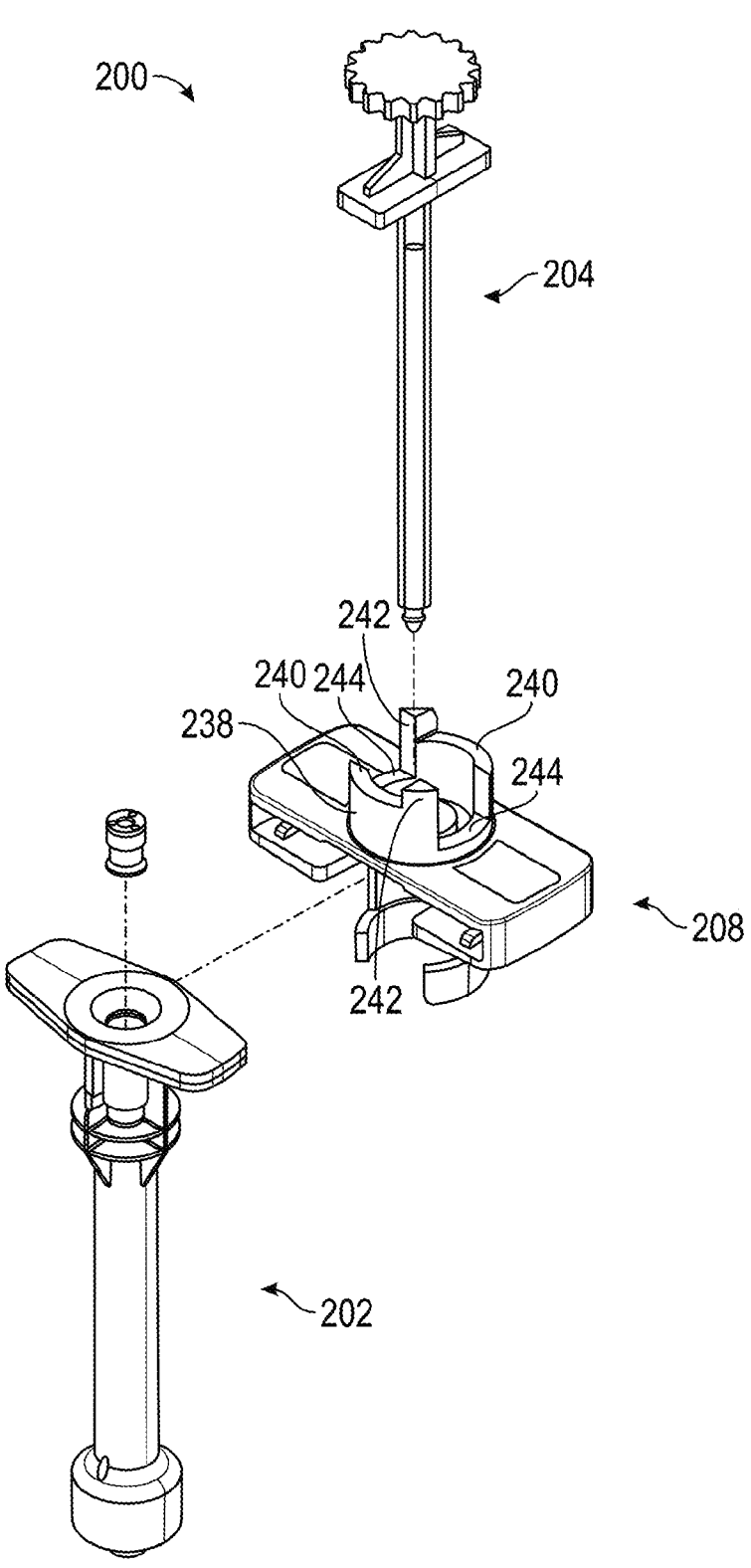

FIGS. 35a to 35c show an exploded view of an injection device, according to various examples. FIGS. 35a to 35c are described below with simultaneous reference to FIGS. 36a to 36c, which show the use of an injection device, according to various examples.

As shown in FIG. 35a, injection device 200 includes injection solution receptacle 202, plunger 204, tip element 206, and housing 208. In some examples, injection solution transferring system 100 includes injection device 200 instead of injection device 10. Injection device 200 provides the similar functionality as injection device 10 (e.g., the accurate and reliable administration of a micro dose of an injection solution to a patient) and interacts with other components of injection solution transferring system 100 (e.g., filling adapter 12) in a same manner as injection device 10. However, unlike injection device 10, injection device 200 is configured to be reusable (e.g., to be used to dispense and/or inject injection solution more than once). Further, injection device 200 has a more intuitive design that has been shown to reduce user error (e.g., when dispensing and/or injecting an injection solution).

Similar to injection solution receptacle 30 of injection device 10, injection solution receptacle 202 of injection device 200 is designed in the form of an inner injection solution receptacle 210 which is contained within a protective outer barrel 212. Inner injection solution receptacle 210 and protective outer barrel 212 are formed integral with each other and are made of a sterile plastic material. In the region of its proximal end, protective outer barrel 212 includes flange element 214.

In some examples, a surface (e.g., an inner circumferential surface) of inner injection solution receptacle 210 is coated with plasma-enhanced chemical vapor deposition (PECVD) coatings or treatments useful to impart a lubricity layer. In some examples, a surface (e.g., an inner circumferential surface) of inner injection solution receptacle 210 is coated with lubricant coating created from the PECVD process using octamethylcyclotetrasiloxane (OMCTS) as the precursor. In some examples, injection solution receptacle 202/inner injection solution receptacle 210 is manufactured via a PECVD process using radiofrequency power comprised of silicon, carbon, and oxygen under at least ISO class 8 conditions in operation and ISO class 7 conditions at rest according to ISO 14644. PECVD coating and treatment is known in the art and is described in at least the following U.S. Patents, each of which is incorporated by reference in its entirety: U.S. Pat. Nos. 10,390,744; 10,363,370; 10,327,986; 10,258,718; 10,201,660; 10,189,603; 10,059,047; 10,016,338; 9,981,794; 9,952,147; 9,937,099; 9,903,782; 9,878,101; 9,863,042; 9,855,577; 9,764,093; 9,664,626; 9,662,450; 9,572,526; 9,554,968; 9,545,360; 9,475,225; 9,458,536; 9,381,687; 9,345,846; 9,272,095; and 8,834,954.

A distal end of injection solution receptacle 202 is provided with male Luer taper 216 and Luer thread 218, which interact with a female Luer taper and a complimentary Luer thread, respectively, (e.g., female Luer taper 50 and complementary Luer thread 54 provided at the second connecting port 22 of adapter element 18 of filling adapter 12 when filling adapter 12 is connected to injection device 200). By means of Luer taper 216 and Luer thread 218, a fluid-tight connection can be established between the distal end of injection solution receptacle 202 and a component that has a female Luer taper and complimentary Luer thread (e.g., adapter element 18 of filling adapter 12).

Outer barrel 212 further includes clip receiver 220. Clip receiver 220 is configured to releasably connect to housing clip 234 of housing 208 (as will be described in greater detail below). In some examples, outer barrel 212 does not include clip receiver 220. In these examples, housing clip 234 releasably connects directly to an outer circumferential surface of outer barrel 212.

In some examples, diameter 222 of inner injection solution receptacle 210 is increased or decreased based on a quantity (e.g., volume) of injection solution that is to be dispensed and/or injected. In other words, in some examples, diameter 222 of inner injection solution receptacle 210 is increased or decreased in order to increase or decrease a quantity of injection solution that is dispensed by injection device 200. For example, as shown in FIG. 35b, diameter 222 is increased (e.g., doubled) to increase a quantity of solution that inner injection solution receptacle 210 can hold and subsequently dispense. Increasing or decreasing diameter 222 requires increasing or decreasing a diameter of outer barrel 212 and a diameter of tip element 206. For example, as shown in FIG. 35b, a diameter of outer barrel 212 and a diameter of tip element 206 are increased such that outer barrel 212 contains inner injection solution receptacle 210 and tip element 206 sealingly interacts with an inner circumferential surface of inner injection solution receptacle 210 (as will be described in greater detail below) in conjunction with the increase of diameter 222. In some examples, a length of injection solution receptacle 202 (and thus a length of inner injection solution receptacle 210) is increased or decreased based on a quantity (e.g., volume) of injection solution that is to be dispensed and/or injected.

Increasing or decreasing a diameter and/or length of inner injection solution receptacle 210 as described above increases or decreases a total amount of injection solution that can be contained within inner injection solution receptacle 210. For example, depending on a diameter and length of inner injection solution receptacle 210, inner injection solution receptacle 210 can contain anywhere between 100 μL to 1000 μL.

In one embodiment, an inner injection solution receptacle 210 can contain at least 100 μL of an injection solution. In one embodiment, an inner injection solution receptacle 210 can contain at least 200 μL of an injection solution. In one embodiment, an inner injection solution receptacle 210 can contain at least 300 μL of an injection solution. In one embodiment, an inner injection solution receptacle 210 can contain at least 400 μL of an injection solution. In one embodiment, an inner injection solution receptacle 210 can contain at least 500 μL of an injection solution. In one embodiment, an inner injection solution receptacle 210 can contain at least 600 μL of an injection solution. In one embodiment, an inner injection solution receptacle 210 can contain at least 700 μL of an injection solution. In one embodiment, an inner injection solution receptacle 210 can contain at least 800 μL of an injection solution. In one embodiment, an inner injection solution receptacle 210 can contain at least 900 μL of an injection solution. In one embodiment, an inner injection solution receptacle 210 can contain at least 1000 μL of an injection solution.

In one embodiment, an inner injection solution receptacle 210 can contain 100 to 900 μL of an injection solution. In one embodiment, an inner injection solution receptacle 210 can contain 100 to 800 μL of an injection solution. In one embodiment, an inner injection solution receptacle 210 can contain 100 to 700 μL of an injection solution. In one embodiment, an inner injection solution receptacle 210 can contain 100 to 600 μL of an injection solution. In one embodiment, an inner injection solution receptacle 210 can contain 100 to 500 μL of an injection solution. In one embodiment, an inner injection solution receptacle 210 can contain 100 to 400 μL of an injection solution. In one embodiment, an inner injection solution receptacle 210 can contain 100 to 300 μL of an injection solution. In one embodiment, an inner injection solution receptacle 210 can contain 100 to 200 μL of an injection solution.

In one embodiment, an inner injection solution receptacle 210 can contain 200 to 1000 μL of an injection solution. In one embodiment, an inner injection solution receptacle 210 can contain 300 to 1000 μL of an injection solution. In one embodiment, an inner injection solution receptacle 210 can contain 400 to 1000 μL of an injection solution. In one embodiment, an inner injection solution receptacle 210 can contain 500 to 1000 μL of an injection solution. In one embodiment, an inner injection solution receptacle 210 can contain 600 to 1000 μL of an injection solution. In one embodiment, an inner injection solution receptacle 210 can contain 700 to 1000 μL of an injection solution. In one embodiment, an inner injection solution receptacle 210 can contain 800 to 1000 μL of an injection solution. In one embodiment, an inner injection solution receptacle 210 can contain 900 to 1000 μL of an injection solution.

In one embodiment, an inner injection solution receptacle 210 can contain 200 to 900 μL of an injection solution. In one embodiment, an inner injection solution receptacle 210 can contain 300 to 800 μL of an injection solution. In one embodiment, an inner injection solution receptacle 210 can contain 400 to 700 μL of an injection solution. In one embodiment, an inner injection solution receptacle 210 can contain 500 to 600 μL of an injection solution.

In one embodiment, an inner injection solution receptacle 210 can contain 100 to 200 μL of an injection solution. In one embodiment, an inner injection solution receptacle 210 can contain 200 to 300 μL of an injection solution. In one embodiment, an inner injection solution receptacle 210 can contain 300 to 400 μL of an injection solution. In one embodiment, an inner injection solution receptacle 210 can contain 400 to 500 μL of an injection solution. In one embodiment, an inner injection solution receptacle 210 can contain 500 to 600 μL of an injection solution. In one embodiment, an inner injection solution receptacle 210 can contain 600 to 700 μL of an injection solution. In one embodiment, an inner injection solution receptacle 210 can contain 700 to 800 μL of an injection solution. In one embodiment, an inner injection solution receptacle 210 can contain 800 to 900 μL of an injection solution. In one embodiment, an inner injection solution receptacle 210 can contain 900 to 1000 μL of an injection solution.

In one embodiment, an inner injection solution receptacle 210 can contain 100 μL of an injection solution. In one embodiment, an inner injection solution receptacle 210 can contain 200 μL of an injection solution. In one embodiment, an inner injection solution receptacle 210 can contain 300 μL of an injection solution. In one embodiment, an inner injection solution receptacle 210 can contain 400 μL of an injection solution. In one embodiment, an inner injection solution receptacle 210 can contain 500 μL of an injection solution. In one embodiment, an inner injection solution receptacle 210 can contain 600 μL of an injection solution. In one embodiment, an inner injection solution receptacle 210 can contain 700 μL of an injection solution. In one embodiment, an inner injection solution receptacle 210 can contain 800 μL of an injection solution. In one embodiment, an inner injection solution receptacle 210 can contain 900

μL of an injection solution. In one embodiment, an inner injection solution receptacle 210 can contain 1000 μL of an injection solution.

Because injection device 200 can be configured to dispense a specific percentage of the total volume of injection solution contained in inner injection solution receptacle 210 (e.g., a specific percentage between 2.5% and 12.5%)—as will be discussed in greater detail below with reference to FIG. 36c—a user of injection device 200 can quickly and easily modify a quantity (e.g., volume) of injection solution that is to be dispensed and/or injected by exchanging the injection solution receptacle 202 of injection device 200 for another injection solution receptacle 202 that can contain a greater or lesser total volume of injection solution. For example, if injection device 200 is configured to deliver 12.5% of a total injection solution volume contained in inner injection solution receptacle 210, injection device 200 would dispense and/or inject 50 μL of injection solution if inner injection solution receptacle 210 contained 400 μL of injection solution and 25 μL of injection solution if inner injection solution receptacle 210 contained 200 μL of injection solution.

Returning to FIG. 35a, injection device 200 further includes plunger 204. Plunger 204 includes actuation button 224, plunger flange 226, one or more guiding channels 227, plunger rod 228, one or more activation channels 229, and tip barb 230. Similar to plunger 70 of injection device 10, plunger 204 is configured such that at least a portion of the plunger 204 (e.g., at least a portion of plunger rod 228) is slidably received within inner injection solution receptacle 210 of injection solution receptacle 202. Further, plunger 204 is displaceable relative to injection solution receptacle 202 in a distal direction along a longitudinal axis of plunger 204 in order to expel injection solution contained in injection solution receptacle 202. Unlike plunger 70, however, plunger 204 is configured to be rotated (e.g., clockwise and counterclockwise) about the longitudinal axis of plunger 204 after inner injection solution receptacle 210 slidably receives at least a portion of plunger 204 (as will be described in greater detail below).

Actuation button 224 is positioned at a proximal end of plunger 204, which protrudes from injection solution receptacle 202 in a proximal direction. Actuation button 224 is depressed by a user in order to displace plunger 204 relative to injection solution receptacle 202 in the distal direction along the longitudinal axis of plunger 204. As shown in FIG. 35a, actuation button 224 includes a plurality of ridges to assist a user with rotating plunger 204. In some examples, actuation button 224 does not include a plurality of ridges (e.g., similar to actuation button 72).

Plunger flange 226 is positioned at the proximal end of plunger 204 beneath actuation button 224. As will be described in greater detail below (e.g., with reference to FIGS. 36a and 36b), plunger flange 226 is configured to interact with plunger stop mechanism 238 such that, based on a longitudinal position and/or rotational orientation of plunger flange 226, plunger stop mechanism 238 prevents the displacement of plunger 204 in the distal direction along the longitudinal axis of plunger 204 and/or prevents the clockwise and/or counterclockwise rotation of plunger 204 about the longitudinal axis of plunger 204. Although plunger flange 226 is rectangular in shape in FIG. 35a, in some examples, plunger flange 226 has a different shape (e.g., triangular, rhombic, oval, or the like). Further, although plunger flange 226 is positioned directly beneath actuation button 224, in some examples, plunger flange 226 is positioned on plunger rod 228 further down the longitudinal axis of plunger 204 (in the distal direction). For example, plunger flange 226 may be positioned at a midpoint of plunger rod 228.

At its distal end, plunger rod 228 of plunger 204 connects to tip element 206 of injection device 200. Tip element 206 is identical to tip element 74 (described in greater detail above with reference to FIG. 13). Further, tip element 206 connects to plunger 204 in the same manner tip element 74 connects to plunger 70. Specifically, a coupling between plunger rod 228 and tip element 206 is effected by an interaction between tip barb 230 positioned at a distal end of plunger rod 228 with a barb receptacle of tip element 206 (e.g., barb receptacle 80). A sealing element of tip element 206 (e.g., sealing element 82) sealingly interacts with an inner circumferential surface of inner injection solution receptacle 210.

Housing 208 of injection device 200 includes flange receptacle 232, housing clip 234, plunger through-hole 236, and plunger stop mechanism 238. Housing 208 is configured to releasably connect to injection solution receptacle 202 and to slidably receive plunger 204.

Figures 36A, 36B, 36C:
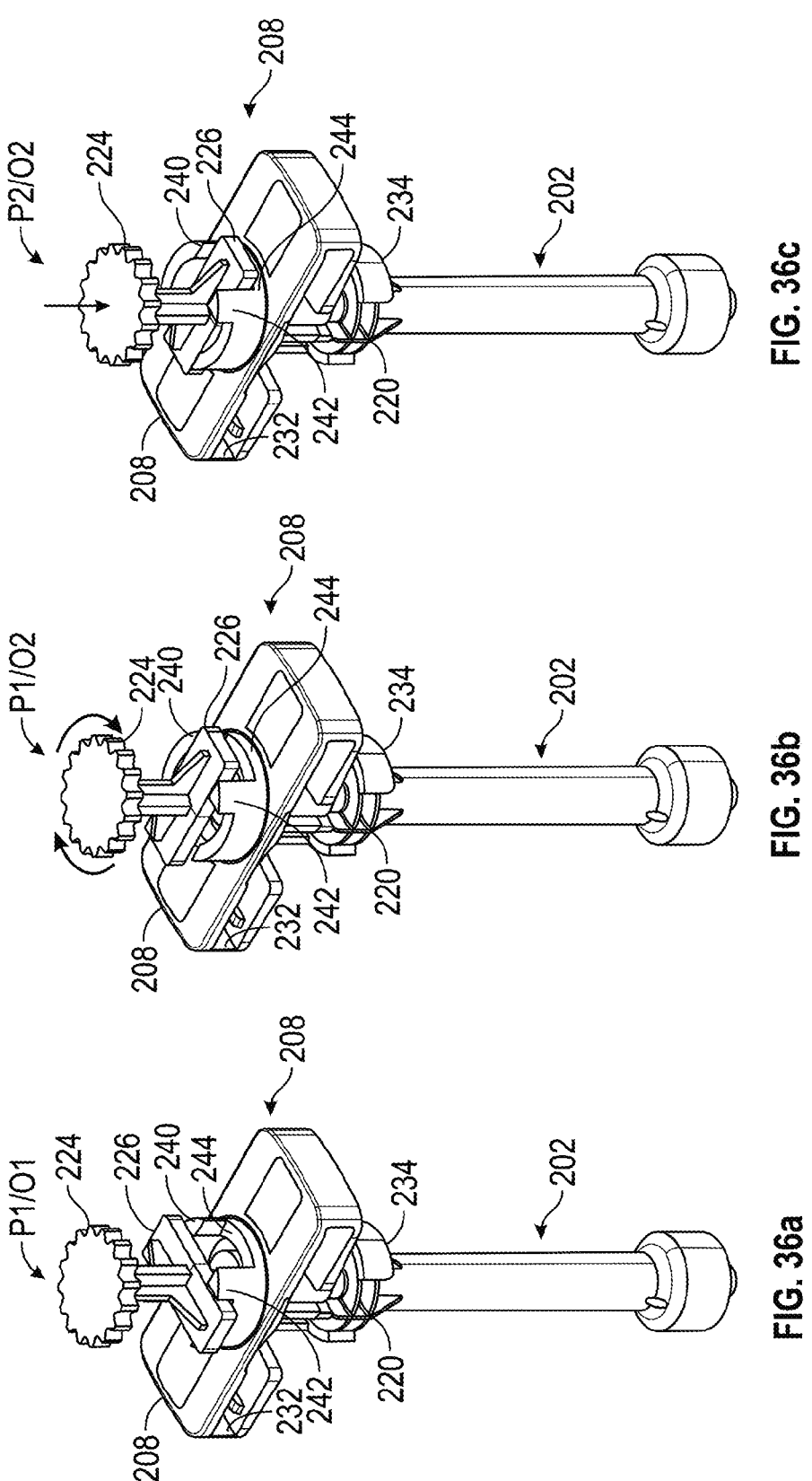
FIGS. 36a to 36c show the use of an injection device, according to various examples.

Housing 208 releasably connects to injection solution receptacle 202 (e.g., as shown in FIGS. 36a and 36b) via the interaction of (1) flange element 214 with flange receptacle 232 and (2) clip receiver 220 with housing clip 234. Specifically, flange receptacle 232 is suitably shaped and dimensioned to receive flange element 214 and, in some examples, to hold flange element 214 in place. Further, housing clip 234 is configured to releasably connect to clip receiver 220 of injection solution receptacle 202 (e.g., as shown in FIGS. 36a and 36b). In the examples described above where outer barrel 212 does not include clip receiver 220, housing clip 234 releasably connects directly to an outer circumferential surface of outer barrel 212. Connecting injection solution receptacle 202 and housing 208 as described above allows housing 208 to be easily and quickly disconnected from injection solution receptacle 202 and, in some examples, to be replaced with another housing (e.g., when plunger 204 is not inserted through injection solution receptacle 202 and housing 208).

Plunger through-hole 236 slidably receives plunger rod 228 (e.g., with tip element 206 attached to plunger rod 228) such that inner injection solution receptacle 210 slidably receives plunger 204 as it slides through plunger through-hole 236. In this manner, plunger 204 is displaceable in a direction along its longitudinal axis relative to housing 208 and injection solution receptacle 202.

In some examples, housing 208 includes one or more guiding elements (not shown) that protrude into plunger through-hole 236. In some examples, the one or more guiding elements of housing 208 are identical to guiding elements 92 of first housing element 86 (e.g., described above with reference to FIG. 16). When plunger 204 is received in plunger through-hole 236 of housing 208, each guiding element engages with a guiding channel 227 positioned on the surface of plunger rod 228, and which extends along the longitudinal axis of plunger rod 228. An interaction between the one or more guiding elements and opposing side surfaces of their corresponding guiding channels 227 prevents a rotation of plunger 204 and housing 208 relative to each other until each guiding element is aligned with a corresponding activation channel 229 on the surface of plunger rod 228.

Each activation channel 229 on the surface of plunger rod 228 branches off from a guiding channel 227 and extends in a circumferential direction of plunger rod 228 substantially perpendicular to its corresponding guiding channel 227. In some examples, the one or more activation channels 229 on the surface of plunger rod 228 are identical to activation channel 178 of plunger 70. Each activation channel 229 receives a guiding element when plunger 204 (1) is arranged at a first dosing position P1 along the longitudinal axis of plunger 204 and (2) is in a first orientation O1 about the longitudinal axis of plunger 204 (e.g., rotational orientation, angular position, or rotational attitude relative to the longitudinal axis). For example, FIG. 36a shows plunger 204 in the first dosing position P1 and in the first orientation O1.

Hence, in examples where housing 208 includes one or more guiding elements and plunger rod 228 includes one or more guiding channels 227/activation channels 229, the first dosing position P1 of plunger 204 is defined at least in part by the position of the one or more activation channels 229 along the longitudinal axis of plunger rod 228. In some examples, the one or more activation channels 229 are positioned on plunger rod 228 such that the one or more guiding elements are aligned with the one or more activation channels 229 when plunger flange 226 contacts plunger stop mechanism 238 (e.g., as shown in FIG. 36a). The interaction between the one or more guiding elements and guiding channels 227 thus fulfills the double function of providing a guided displacement of plunger 204 in a direction along its longitudinal axis and simultaneously preventing an unintentional rotation of plunger 204 when plunger 204 is not arranged at first dosing position P1 in the first orientation O1. This in turn makes injection device 200 easier to use and thus reduces user error (e.g., when dispensing and/or injecting an injection solution).

Plunger stop mechanism 238 is positioned on a proximal surface of housing 208 adjacent to (e.g., at least partially encircling) plunger through-hole 236. Plunger stop mechanism 238 includes longitudinal stop members 240, rotational stop members 242, and dosing surface 244. As shown in FIG. 35a, longitudinal stop members 240, rotational stop members 242, and dosing surface 244 project from the proximal surface of housing 208 in a proximal direction, with rotational stop members 242 projecting further in the proximal direction than longitudinal stop members 240 and dosing surface 244. Specifically, a height of rotational stop members 242 is greater than a height of longitudinal stop members 240, and the height of longitudinal stop members 240 is greater than a height of dosing surface 244. In some examples, dosing surface 244 does not project from the proximal surface of housing 208. In these examples, the proximal surface of housing 208 in between longitudinal stop members 240 and rotational stop members 242 serves as dosing surface 244. In some examples, plunger stop mechanism 238 only includes a single longitudinal stop member 240 and a single rotational stop member 242 (instead of two longitudinal stop members 240 and two rotational stop members 242 as shown in FIG. 35a). In some examples, the plunger stop mechanism includes more than two longitudinal stop members and more than two rotational stop members.

In some examples, injection device 200 is used to dispense and/or inject a precise does of a solution (e.g., a dose within a range of 5 μL to 250 μL of injection solution) contained within inner injection solution receptacle 210. In a first step, excess injection solution is expelled from inner injection solution receptacle 210 by displacing plunger 204 relative to inner injection solution receptacle 210 in the distal direction (e.g., while plunger 204 is in the first orientation O1 about the longitudinal axis of plunger 204) until plunger 204 reaches the first dosing position P1 along the longitudinal axis of plunger 204. As shown in FIG. 36a, plunger 204 is in the first dosing position P1 and in the first orientation O1 when plunger flange 226 contacts longitudinal stop members 240 and rotational stop members 242. Thereafter, the desired dose/quantity of the injection solution can be dispensed and/or injected (e.g., into patient tissue).

As shown in FIG. 36a, longitudinal stop members 240 are configured to prevent a displacement of plunger 204 relative to injection solution receptacle 202/inner injection solution receptacle 210 in the distal direction at the first dosing position P1. Specifically, longitudinal stop members 240 prevent a displacement of plunger 204 in the distal direction when longitudinal stop members 240 come into contact with/abut plunger flange 226. Further, rotational stop members 242 are configured to prevent plunger 204 from rotating in a counterclockwise direction about the longitudinal axis of plunger 204 when plunger 204 is at the first dosing position P1 and in the first orientation O1. Specifically, rotational stop members 242 prevent plunger 204 from rotating in a counterclockwise direction when rotational stop members 242 come into contact with/abut plunger flange 226. In some examples, both rotational stop members 242 are positioned on the other side of their neighboring longitudinal stop member 240 (e.g., opposite from their position shown in FIG. 35a). In these examples, rotational stop members 242 prevent plunger 204 from rotating in a clockwise direction when rotational stop members 242 come into contact with/abut plunger flange 226.

Thus, during use of injection device 200, a user can expel excess injection solution from inner injection solution receptacle 210 by displacing plunger 204 relative to inner injection solution receptacle 210 in the distal direction until plunger 204 reaches the first dosing position P1 (e.g., until plunger flange 226 contacts longitudinal stop members 240). Upon reaching the first dosing position P1, longitudinal stop members 240 prevent further displacement of plunger 204 in the distal direction. Consequently, a user of injection device 200 is prevented from expelling too much injection solution from inner injection solution receptacle 210. The residual injection solution contained in inner injection solution receptacle 210 can then be dispensed and/or injected by further displacing plunger 204 in the distal direction until plunger 204 reaches a second dosing position P2. Specifically, as shown in FIG. 36c, plunger 204 reaches the second dosing position P2 when plunger flange 226 (e.g., a bottom/distal surface of plunger flange 226) comes into contact with/abuts dosing surface 244. Upon reaching the second dosing position P2, dosing surface 244 prevents further displacement of plunger 204 in the distal direction and thus prevents too much injection solution from being dispensed and/or injected.

However, before a user of injection device 200 can displace plunger 204 to the second dosing position P2, the user must manually rotate plunger 204 (e.g., using actuation button 224) in a clockwise direction about the longitudinal axis of plunger 204 from the first orientation O1 to a second orientation O2, as shown in FIG. 36b. Specifically, plunger 204 is in the second orientation O2 when plunger flange 226 once again comes into contact with/abuts rotational stop members 242 after being rotated in the clockwise direction. Note, although FIG. 36b shows plunger 204 rotating 90 degrees in the clockwise direction to get from the first orientation O1 to the second orientation O2, in some examples, a user must rotate plunger 204 more or less than 90 degrees (e.g., 110 degrees or 45 degrees) to get to the second orientation O2 from the first orientation O1. In these examples, longitudinal stop members 240, rotational stop members 242, and dosing surface 244 are shaped and positioned on the proximal surface of housing 208 to accommodate the greater or lesser rotational movement of plunger 204. In this manner, plunger flange 226 will, for example, still come into contact with/abut rotational stop members 242 when in the first orientation O1 and when in the second orientation O2.

Rotating plunger 204 from the first orientation O1 to the second orientation O2 (while plunger 204 is at the first dosing position P1) aligns plunger flange 226 directly above dosing surface 244 (and the recess formed between longitudinal members 240/rotational stop members 242 and dosing surface 244 due to the difference in height between longitudinal members 240/rotational stop members 242 and dosing surface 244). In other words, as shown in FIG. 36b, when plunger 204 is in the second orientation O2, a distal/bottom surface of plunger flange 226 is arranged parallel to dosing surface 244. As a result, a user of injection device 200 can further displace plunger 204 in the distal direction from the first dosing position P1 to the second dosing position P2, until plunger flange 226 comes into contact with/abuts dosing surface 244. Dosing surface 244 provides a hard stop for plunger 204 and prevents plunger 204 from being further displaced in the distal direction (relative to injection solution receptacle 202/inner injection solution receptacle 210) from the second dosing position P2. The dose of the injection solution to be administered to a patient can thus be set in a particularly accurate manner.

Specifically, the distance between the first dosing position P1 and the second dosing position P2 of plunger 204 is selected in such a manner that plunger 204 expels a specific percentage of a total volume of injection solution contained in inner injection solution receptacle 210 (e.g., a specific percentage between 2.5% and 12.5%) upon being displaced from the first dosing position P1 to the second dosing position P2. In other words, the distance between a top/proximal surface of longitudinal stop members 240 (e.g., that contacts a bottom/distal surface of plunger flange 226) and dosing surface 244 in the distal direction sets the desired injection solution dose to be expelled from inner injection solution receptacle 210 upon displacing plunger 204 from the first dosing position P1 to the second dosing position P2.

Accordingly, varying the height of longitudinal stop members 240 (e.g., the distal distance from a top/proximal surface of longitudinal stop members 240 to dosing surface 244) will vary a quantity of dose to be dispensed and/or injected (e.g., when a total volume of injection solution contained in inner injection solution receptacle 210 is unchanged). For example, as shown in FIG. 35c, a height (e.g., proximal distance from a proximal/top surface of housing 208) of longitudinal stop members 240 (and thus a height of rotational stop members) can be increased without altering dosing surface 244. Thus, in this example, the increased distal distance between the proximal/top surface of longitudinal members 240 and dosing surface 244 will result in a larger percentage of a total volume of injection solution contained in inner injection solution receptacle 210 to be dispensed and/or injected, as plunger 204 will travel a greater distance along its longitudinal axis and thus dispense more injection solution contained in inner injection solution receptacle 210. For example, if inner injection solution receptacle 210 contains 200 μL of injection solution, increasing the distal distance between the proximal/top surface of longitudinal stop members 240 and dosing surface 244 such that plunger 204 dispenses 12.5% of the total volume of injection solution instead of 2.5% will result in a 20 μL increase in the quantity of injection solution that plunger 204 will expel from inner injection solution receptacle 210 when plunger 204 is displaced from the first dosing position P1 to the second dosing position P2 (e.g., because 2.5% of 200 µL is 5 µL whereas 12.5% of 200 µL is 25 µL).

The ability of longitudinal stop members 240 and rotational stop members 242 to prevent the displacement of plunger 204 in the distal direction (when plunger 204 is at the first dosing position P1 and in the first orientation O1) and to prevent certain rotation of plunger 204 (when plunger 204 is at the first dosing position P1 and in the first orientation O1 or second orientation O2), respectively, provides various benefits with respect to dispensing and/or injecting an accurate micro dose of injection solution. For example, because of longitudinal stop members 240 and rotational stop members 242, a user of injection device 200 can easily and comfortably deliver an accurate micro dose of an injection solution. Specifically, longitudinal stop members 240 allow a user to quickly and easily prime injection device 200 without accidentally dispensing and/or injecting the injection solution for the desired micro dose, as longitudinal stop members 240 prevent plunger 204 from being slidably displaced in a distal direction beyond what is necessary to prime injection device 200. Moreover, when plunger 204 is at the first dosing position P1 and in the first orientation O1, rotational stop members 242 prevent a user from accidentally rotating plunger 204 in a counterclockwise direction (or, in some examples, a clockwise direction) and subsequently displacing plunger 204 to the second dosing position P2 (and dispensing and/or injecting injection solution). In this manner, rotational stop members 242 force a user of injection device 200 to purposefully rotate plunger 204 in a single direction (e.g., clockwise or counterclockwise) towards the second orientation O2 in order to subsequently dispense and/or inject injection solution by displacing plunger 204 to the second dosing position P2.

Thus, for at least the above reasons, longitudinal stop members 240 and rotational stop members 242 guide a user's displacement of plunger 204 and prevent the user from accidentally dispensing and/or injecting injection solution (e.g., accidentally dispensing/injecting too much injection solution and/or dispensing/injecting injection solution at an inopportune time and/or in an incorrect location (e.g., incorrect patient tissue)). This in turn makes injection device 200 particularly easy to use and thus reduces user error. For example, Table (1) below includes results of a simulated use study of injection device 200. As shown, the simulated use study evaluated various tasks for the use of injection device 200. Before the evaluation, representative training was provided to the ophthalmologists/retinal surgeons (i.e., the participants) and the evaluation session was conducted after a decay period of 1 to 7 weeks. Overall, based on the evaluation n=25/30 (83%) participants successfully performed the first injection without having any use error and n=24/30 (80%) participants successfully performed the second injection without having any use errors. A total of 22 steps out of 26 steps (84.6%) were successfully performed without any use errors. Thus, for at least the above reasons, injection device 200 is particularly suitable, for example, for injecting injection solution into pediatric patients (e.g., pediatric ophthalmic injections) because pediatric patients typically do not stay still when receiving injections (e.g., due to fear of injections and/or pain caused by injections), making accidental and inaccurate injections more likely with standard injection devices that do not guide a user's displacement of the injection device's plunger.

TABLE (1)

Summary of Study Results

| Tasks | Id. | Steps/sub-steps | Category | N | Pass | Pass with difficulty | Close call | Use error |
|---|---|---|---|---|---|---|---|---|
| Store | 1.1 | Store the Application Kit according to labelling requirements | N | 58* | 58 | 0 | 0 | 0 |
| Material Handling | 2.1 | Handle the appropriate materials aseptically throughout procedure | C | 60 | 57 | 3 | 0 | 0 |
| Perform safety checks | 3.1 | Perform safety checks throughout Tasks 4 & 5 & 6 on drug product appearance for e.g. particles, cloudiness | D | 60 | 48 | 12 | 0 | 0 |
| | 3.2 | Perform safety checks throughout Tasks 4, 5 and 6 on syringe and injection needle for e.g. damage, expiration date. | D | 60 | 50 | 10 | 0 | 0 |
| Collect and unpack | 4.1 | Allow drug to reach room temperature. | D | 60 | 54 | 6 | 0 | 0 |
| | 4.2 | Open the folding box and remove syringe and injection needle. | N | 32* | 22 | 9 | 0 | 1 |
| Prepare medication | 4.3 | Remove syringe and injection needle from packaging. | N | 31* | 31 | 0 | 0 | 0 |
| | 5.1 | Remove cap from top of vial. | N | 27* | 27 | 0 | 0 | 0 |
| | 5.2 | Clean the vial septum. | D | 60 | 54 | 6 | 0 | 0 |
| | 5.3 | Push the plunger rod towards the needle end until a stop is felt. | N | 33* | 33 | 0 | 0 | 0 |
| | 5.4 | Assemble filter needle onto the syringe. | N | 34* | 31 | 3 | 0 | 0 |
| | 5.5 | Remove the cap from the filter needle. | N | 33* | 33 | 0 | 0 | 0 |
| | 5.6 | Insert filter needle into vial. | N | 31* | 30 | 1 | 0 | 0 |
| | 5.7 | Slightly incline vial. | N | 33* | 28 | 2 | 0 | 3 |
| | 5.8 | Withdraw the drug product. | N | 32* | 29 | 3 | 0 | 0 |
| | 5.9 | Disconnect the syringe from the | N | 30* | 27 | 3 | 0 | 0 |

TABLE (1)-continued

Summary of Study Results

| Tasks | Id. | Steps/sub-steps | Category | N | Pass | Pass with difficulty | Close call | Use error |
|---|---|---|---|---|---|---|---|---|
| | | filter needle. | | | | | | |
| Prepare syringe | 6.1 | Assemble the injection needle onto the syringe. | N | 30* | 28 | 2 | 0 | 0 |
| | 6.2 | Separate liquid from air ensuring air is at the needle end of the syringe. | N | 30* | 17 | 6 | 0 | 7 |
| | 6.3 | Remove the cap from the injection needle. | N | 30* | 30 | 0 | 0 | 0 |
| | 6.4 | Expel the air from the syringe and the injection needle. | N | 30* | 30 | 0 | 0 | 0 |
| | 6.5 | Set the dose-Expel liquid from syringe that is not needed for dose. | C | 30* | 30 | 0 | 0 | 0 |
| Perform injection | 6.6 | Unlock the syringe-so it is enabled for injection of the specific dose. (Twist the plunger) | C | 30* | 29 | 0 | 0 | 1 |
| | 7.1 | Insert injection needle into the injection site (eye). | C | 30* | 30 | 0 | 0 | 0 |
| | 7.2 | Deliver the contents of the syringe. | C | 30* | 28 | 2 | 0 | 0 |
| | 7.3 | Remove the injection needle from the injection site (eye). | N | 30* | 30 | 0 | 0 | 0 |
| Dispose Materials | 8.1 | Dispose of all materials according to local regulations (e.g. sharps bin). | D | 60 | 60 | 0 | 0 | 0 |

Returning to FIG. 35a, as mentioned above, housing 208 may be easily and quickly disconnected from injection solution receptacle 202 and, in some examples, replaced with another housing. This in turn allows for housing 208 to be quickly replaced with another housing based on, for example, a quantity of injection solution that is to be dispensed and/or injected. For example, housing 208 of FIG. 35a may be replaced with a housing having a longitudinal stop member that has a greater height (e.g., such as housing 208 of FIG. 35c). In this manner, injection device 200 can be reused multiple times to accurately dispense and/or inject a micro dose of an injection solution even if a different quantity of injection solution is desired for each individual use of injection device 200 (since housing 208 is a modular component that can be exchanged based on the desired micro dose). Further, the modularity of housing 208 allows a user to, for example, quickly exchange housing 208 based on a desired quantity of injection solution to be dispensed and/or injected during a patient procedure (e.g., if a patient procedure requires multiple injections of different injection solution quantities).

In some examples, plunger stop mechanism 238 (specifically, longitudinal stop members 240, rotational stop members 242, and/or dosing surface 244) is positioned/fixed on plunger 204 instead of on the proximal/top surface of housing 208. In these examples, plunger stop mechanism 238 faces in a distal direction (e.g., towards housing 208) instead of in a proximal direction. In other words, longitudinal stop members 240 and rotational stop members 242 project in a distal direction.

In some examples, plunger stop mechanism 238 is positioned/fixed on a distal/bottom surface of actuation button 224 of plunger 204 such that longitudinal stop members 240, rotational stop members 242, and dosing surface 244 project in a distal direction from the distal/bottom surface of actuation button 224 towards housing 208 (and thus are adjacent to and/or encircle plunger rod 228). In some examples, only longitudinal stop members 240 and rotational stop members 242 project in the distal direction from the distal/bottom surface of actuation button 224. In these examples, dosing surface 244 is the distal/bottom surface of actuation button 224.

In some examples, plunger stop mechanism 238 is positioned/fixed on plunger rod 228. In these examples, plunger stop mechanism 238 has a proximal/top surface that attaches plunger stop mechanism 238 to plunger rod 228 (and from which longitudinal stop members 240, rotational stop members 242, and/or dosing surface 244 project in a distal direction). Specifically, plunger rod 228 intersects through the proximal/top surface, and plunger stop mechanism is permanently (e.g., not slidably) attached to plunger rod 228 at this point of intersection. In some examples, plunger stop mechanism 238 replaces plunger flange 226 of plunger 204 (and thus plunger stop mechanism 238 is positioned where plunger flange 226 is positioned in FIGS. 35a to 36b). In some examples, plunger stop mechanism 238 is positioned on plunger rod 228 further down the longitudinal axis of plunger 204 (in the distal direction). For example, plunger stop mechanism 238 may be positioned at a midpoint of plunger rod 228.

Note, the various embodiments of plunger stop mechanism 238 described above (e.g., with taller/shorter longitudinal stop members 240, different degrees of plunger 204 rotation to arrive at the second orientation O2, and different number of longitudinal stop members 240 and/or rotational stop members 242) are still applicable in the examples above where plunger stop mechanism 238 is positioned on plunger 204.

When plunger stop mechanism 238 is positioned on plunger 204 (e.g., on a distal/bottom surface of actuation button 224 or on plunger rod 228), housing 208 is configured to interact with the components of plunger stop mechanism 238 in a same manner that plunger flange 226 interacts with the components of plunger stop mechanism 238 when plunger stop mechanism 238 is positioned on housing 208. For example, housing 208 is configured to interact with longitudinal stop members 240 to prevent plunger 204 from being further displaced in the distal direction when plunger 204 is at the first dosing position P1 and in the first orientation O1. As another example, housing 208 is configured to interact with rotational stop members 242 to prevent plunger 204 from rotating in a counterclockwise direction (or, in some examples, a clockwise direction) about the longitudinal axis of plunger 204 when plunger 204 is at the first dosing position P1 and in the first orientation O1.

Specifically, in some examples, at least a portion of the proximal/top surface of housing 208 surrounding plunger through-hole 236 projects in a proximal direction along the longitudinal axis of plunger 204 toward plunger stop mechanism 238 (such that plunger through-hole 236 may still slidably receive plunger rod 228). In these examples, the projecting proximal/top surface of housing 208 has a height that is at least equal to the distal distance between dosing surface 244 and distal surfaces of rotational stop members 242 (i.e., the surfaces of rotational stop members 242 that face in the distal direction toward housing 208). In this manner, when dosing surface 244 comes into contact with/abuts the projecting proximal/top surface of housing 208 (at the second dosing position P2), the distal surfaces of rotational stop members 242 are either (1) flush with the portion of the proximal/top surface of housing 208 that is not projecting in the proximal direction (e.g., when a height of the projecting proximal/top surface of housing 208 is equal to the distal distance between dosing surface 244 and the distal surfaces of rotational stop members 242) or (2) do not come into contact with the portion of the proximal/top surface of housing 208 that is not projecting in the proximal direction (e.g., when a height of the projecting proximal/top surface of housing 208 is greater than the distal distance between dosing surface 244 and the distal surfaces of rotational stop members 242). Further, the projecting proximal/top surface of housing 208 is shaped to fit in the recess formed between longitudinal members 240/rotational stop members 242 and dosing surface 244. In some examples, the projecting proximal/top surface of housing 208 has the same rectangular shape as plunger flange 226 in FIGS. 35a to 35c. In some examples, the projecting proximal/top surface of housing 208 has a different shape (e.g., triangular, rhombic, oval, or the like) depending on the shape of the recess formed between longitudinal members 240/rotational stop members 242 and dosing surface 244.

In the examples described above where plunger stop mechanism is on plunger 204, plunger 204 may be replaced with another plunger 204 based on, for example, a quantity of injection solution that is to be dispensed and/or injected (similar to how housing 208 may be replaced when plunger stop mechanism 238 is on the proximal/top surface of housing 208). In other words, plunger 204 may be replaced with another plunger 204 that has different (e.g., taller or shorter) longitudinal stop members 240, rotational stop members 242, and/or dosing surface 244. In this manner, injection device 200 can be reused multiple times to accurately dispense and/or inject a micro dose of an injection solution even if a different quantity of injection solution is desired for each individual use of injection device 200 (since plunger 204 is a modular component that can be exchanged based on the desired micro dose). Further, the modularity of plunger 204 (that includes plunger stop mechanism 238) allows a user to, for example, quickly exchange plunger 204 based on a desired quantity of injection solution to be dispensed and/or injected during a patient procedure (e.g., if a patient procedure requires multiple injections of different injection solution quantities).

Figure 37B:
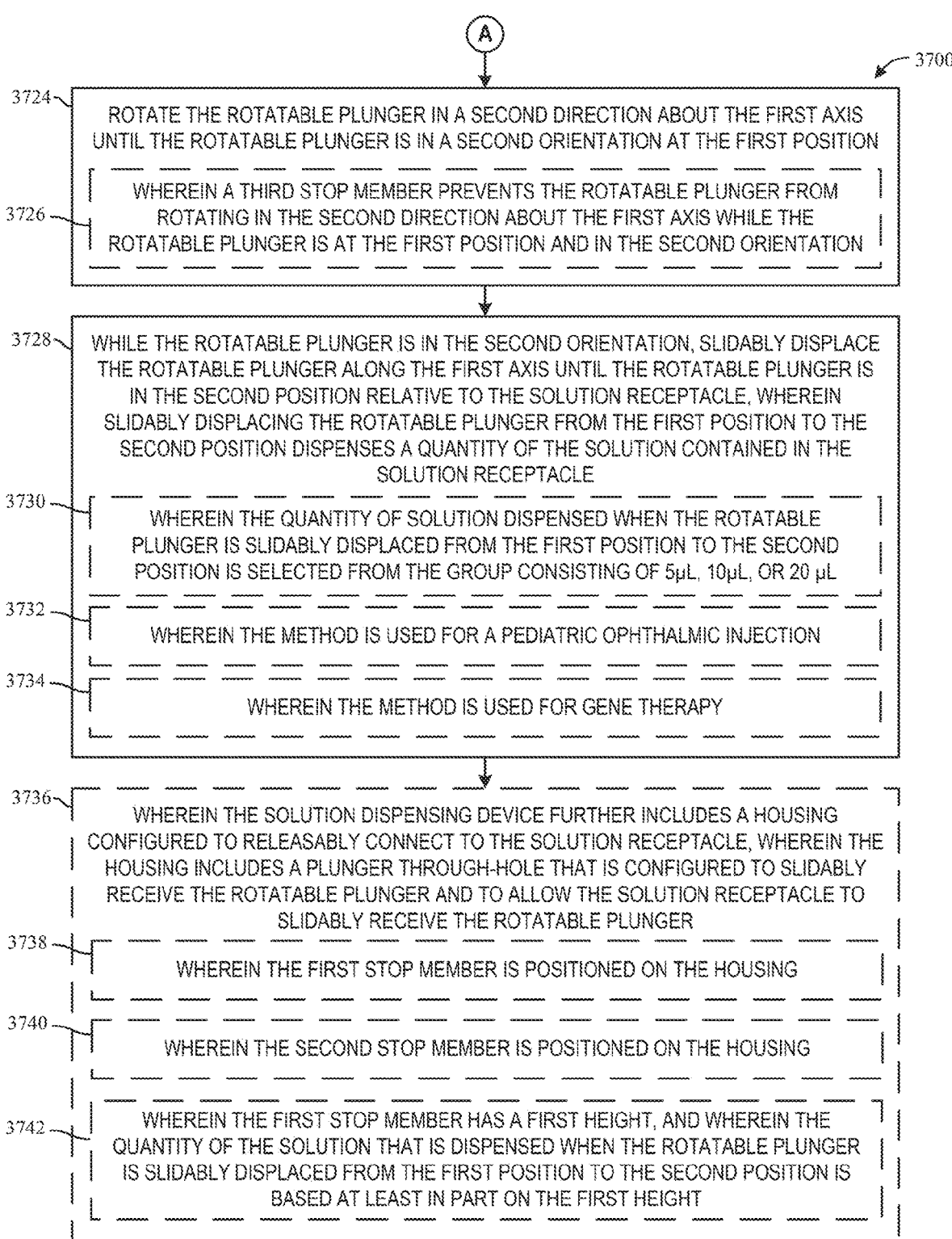

FIGS. 37a to 37b show a flow diagram of a process for using a solution dispensing device to dispense a quantity of solution, according to various examples. Process 3700 is performed, for example, using injection device 10 or injection device 200. In process 3700, some blocks are, optionally, combined, the order of some blocks is, optionally, changed, and some blocks are, optionally, omitted. In some examples, additional steps may be performed in combination with process 3700.

At block 3702, a rotatable plunger (e.g., plunger 204) is slidably inserted into a first end of the solution receptacle (e.g., inner injection solution receptacle 30 or inner injection solution 210), wherein a second end of the solution receptacle (e.g., male Luer taper 48 or Luer taper 216) is configured to dispense a solution contained in the solution receptacle. In some examples, the solution contains a vascular endothelial growth factor (VEGF) antagonist (e.g., ranibizumab (i.e., Lucentis™)), as shown at block 3704. In some examples, the solution contains nucleic acids, as shown at block 3706. In some examples, the solution contains Beovu® (brolucizumab). In some examples, the solution contains Eylea® (aflibercept). In some examples, the solution contains Luxturna® (Voretigene neparvovec).

At block 3708, while the rotatable plunger is in a first orientation (e.g., rotational orientation, angular position, rotational attitude relative to the first axis) (e.g., first orientation O1), the rotatable plunger is slidably displaced along a first axis until the rotatable plunger is in a first position (e.g., first dosing position P1) relative to the solution receptacle.

At block 3710, a first stop member (e.g., longitudinal stop member 240) prevents the rotatable plunger from being slidably displaced to a second position (e.g., second dosing position P2) relative to the solution receptacle that is closer to the second end of the solution receptacle than the first position (e.g., the rotatable plunger is slidably displaced further into the solution receptacle when in the second position than when in the first position) while the rotatable plunger is at the first position and in the first orientation.

In some examples, the first stop member is positioned on the rotatable plunger, as shown at block 3712. In some examples, the first stop member is positioned on a bottom surface of an actuation button (e.g., actuation button 72 or actuation button 224) positioned on an end of the rotatable plunger that is not slidably received by the solution receptacle (e.g., the bottom surface being closer to the first end of the solution receptacle (along the first axis) than a top surface of the actuation button). In some examples, the first stop member is positioned at a point along a shaft of the rotatable plunger (e.g., at a midpoint of the rotatable plunger).

In some examples, the rotatable plunger includes a flange (e.g., a flange having a first shape (e.g., rectangular, oval, diamond, or the like) that is fixed on the rotatable plunger and that rotates about the first axis with the rotatable plunger) (e.g., flange 226) that contacts the first stop member and prevents the rotatable plunger from being slidably displaced to the second position while the rotatable plunger is at the first position and in the first orientation, as shown at block 3714. In some examples, the flange is positioned on an end of the rotatable plunger that is not slidably received by the solution receptacle (e.g., directly beneath a bottom surface of an actuation button of the rotatable plunger). In some examples, the flange is positioned at a point along a shaft of the rotatable plunger (e.g., at a midpoint of the rotatable plunger shaft).

At block 3716, a second stop member (e.g., rotational stop member 242) prevents the rotatable plunger from rotating in a first direction about the first axis (e.g., rotating in the first direction (e.g., counterclockwise) so as to arrive at the second orientation) while the rotatable plunger is at the first position and in the first orientation.

In some examples, the second stop member is positioned on the rotatable plunger, as shown at block 3718. In some examples, the second stop member is positioned on a bottom surface of an actuation button positioned on an end of the rotatable plunger that is not slidably received by the solution receptacle (e.g., the bottom surface being closer to the first end of the solution receptacle (along the first axis) than a top surface of the actuation button). In some examples, the second stop member is positioned at a point along a shaft of the rotatable plunger (e.g., at a midpoint of the rotatable plunger).

In some examples, the rotatable plunger includes a flange (e.g., a flange having a first shape (e.g., rectangular, oval, diamond, or the like) that is fixed on the rotatable plunger and that rotates about the first axis with the rotatable plunger) that contacts the second stop member and prevents the rotatable plunger from rotating about the first axis in the first direction while the rotatable plunger is at the first position and in the first orientation, as shown at block 3720.

In some examples, the solution dispensing device is configured to prevent the rotatable plunger from rotating about the first axis (e.g., prevent the rotatable plunger from rotating in any direction (e.g., first or second direction)) until the rotatable plunger is positioned at the first position, as shown at block 3722. In some examples, the solution dispensing device further includes one or more guiding elements (e.g., guiding elements 92) that are configured to engage with one or more guiding channels (e.g., guiding channels 227) of the rotatable plunger and to prevent the rotatable plunger from rotating about the first axis until the rotatable plunger is positioned at the first position. In some examples, the solution receptacle includes the guiding elements (e.g., at the first end). In some examples, the housing includes the guiding elements (e.g., at the plunger through-hole).

At block 3724, the rotatable plunger is rotated in a second direction about the first axis until the rotatable plunger is in a second orientation (e.g., second orientation O2) at the first position. In some examples, a third stop member (e.g., rotational stop member 242) prevents the rotatable plunger from rotating in the second direction (e.g., rotating in the second direction (e.g., clockwise) so as to arrive at the first orientation) about the first axis while the rotatable plunger is at the first position and in the second orientation, as shown at block 3726.

At block 3728, while the rotatable plunger is in the second orientation, the rotatable plunger is slidably displaced along the first axis until the rotatable plunger is in the second position relative to the solution receptacle, wherein slidably displacing the rotatable plunger from the first position to the second position dispenses a quantity (e.g., fixed volume, metered volume) of the solution contained in the solution receptacle. In some examples, the quantity of solution dispensed when the rotatable plunger is slidably displaced from the first position to the second position is selected from the group consisting of 5 μL, 10 μL, and 20 μL, as shown at block 3730.

In some examples, the solution receptacle contains between 100 μL to 1000 μL of the solution. In some examples, the quantity of solution dispensed when the rotatable plunger is slidably displaced from the first position to the second position is between 2.5% and 12.5% of the solution contained in the solution receptacle.

In some examples, the method (e.g., process 3700) is used for a pediatric ophthalmic injection, as shown at block 3732. In some examples, the method (e.g., process 3700) is used for gene therapy, as shown at block 3734.

In some examples, the solution dispensing device further includes a housing (e.g., a fixed housing that does not rotate about the first axis) (e.g., housing 208) configured to releasably connect to the solution receptacle (e.g., connect to the solution receptacle using a releasable clip included in the housing), wherein the housing includes a plunger through-hole (e.g., plunger through-hole or plunger through-hole 236) that is configured to slidably receive the rotatable plunger and to allow the solution receptacle to slidably receive the rotatable plunger, as shown at block 3736.

In some examples, the first stop member is positioned on the housing (e.g., positioned adjacent to the plunger through-hole on a top surface of the housing, with the top surface being further from the first end of the solution receptacle than a bottom surface of the housing), as shown at block 3738.

In some examples, the second stop member is positioned on the housing (e.g., positioned adjacent to the plunger through-hole on a top surface of the housing, with the top surface being further from the first end of the solution receptacle than a bottom surface of the housing), as shown at block 3740.

In some examples, the first stop member has a first height, wherein the quantity of the solution that is dispensed when the rotatable plunger is slidably displaced from the first position to the second position is based at least in part on the first height, as shown at block 3742.

Figure 38K:
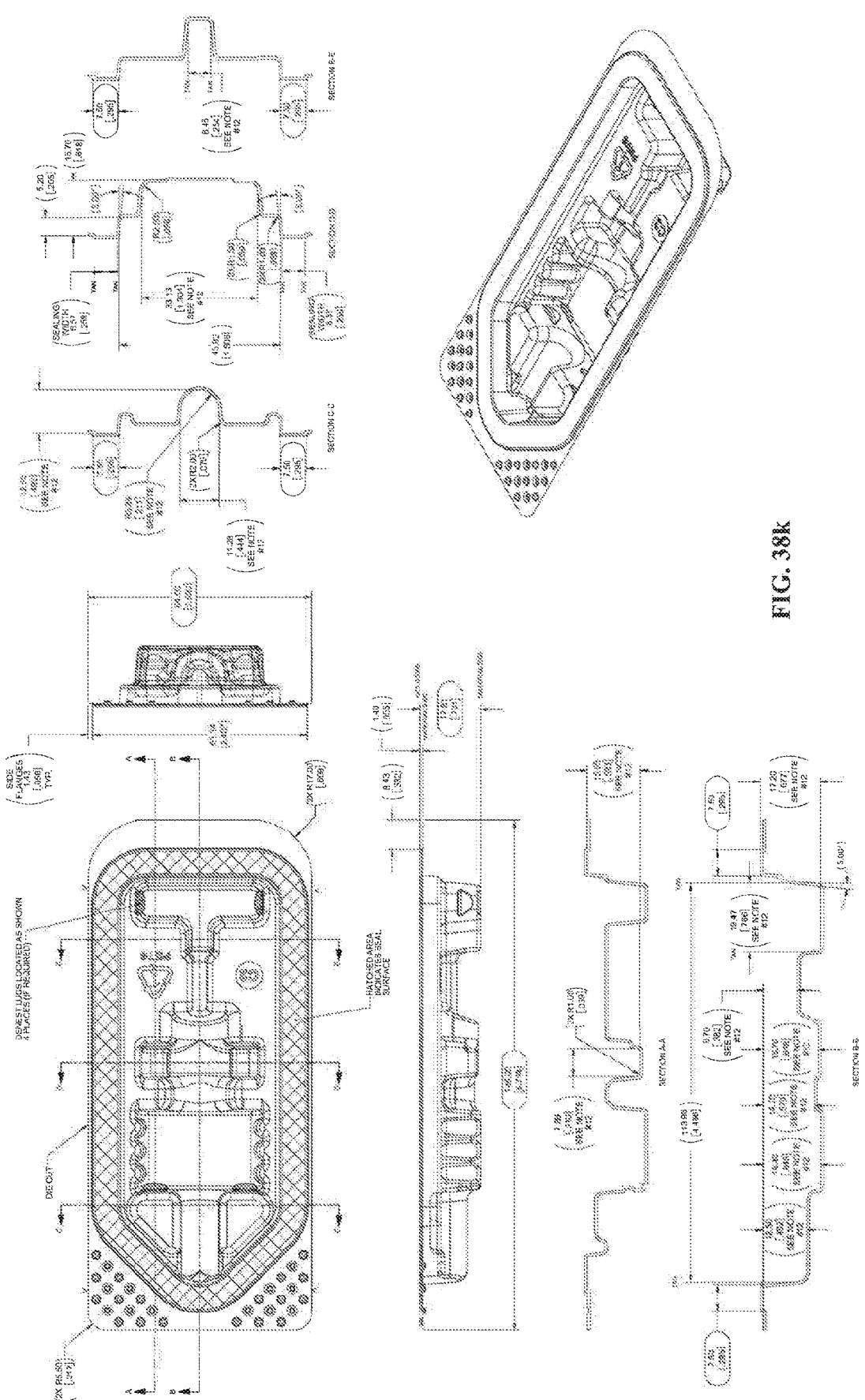
FIGS. 38a to 38s show additional views of an injection device and its components, according to various examples.
Figure 38M:
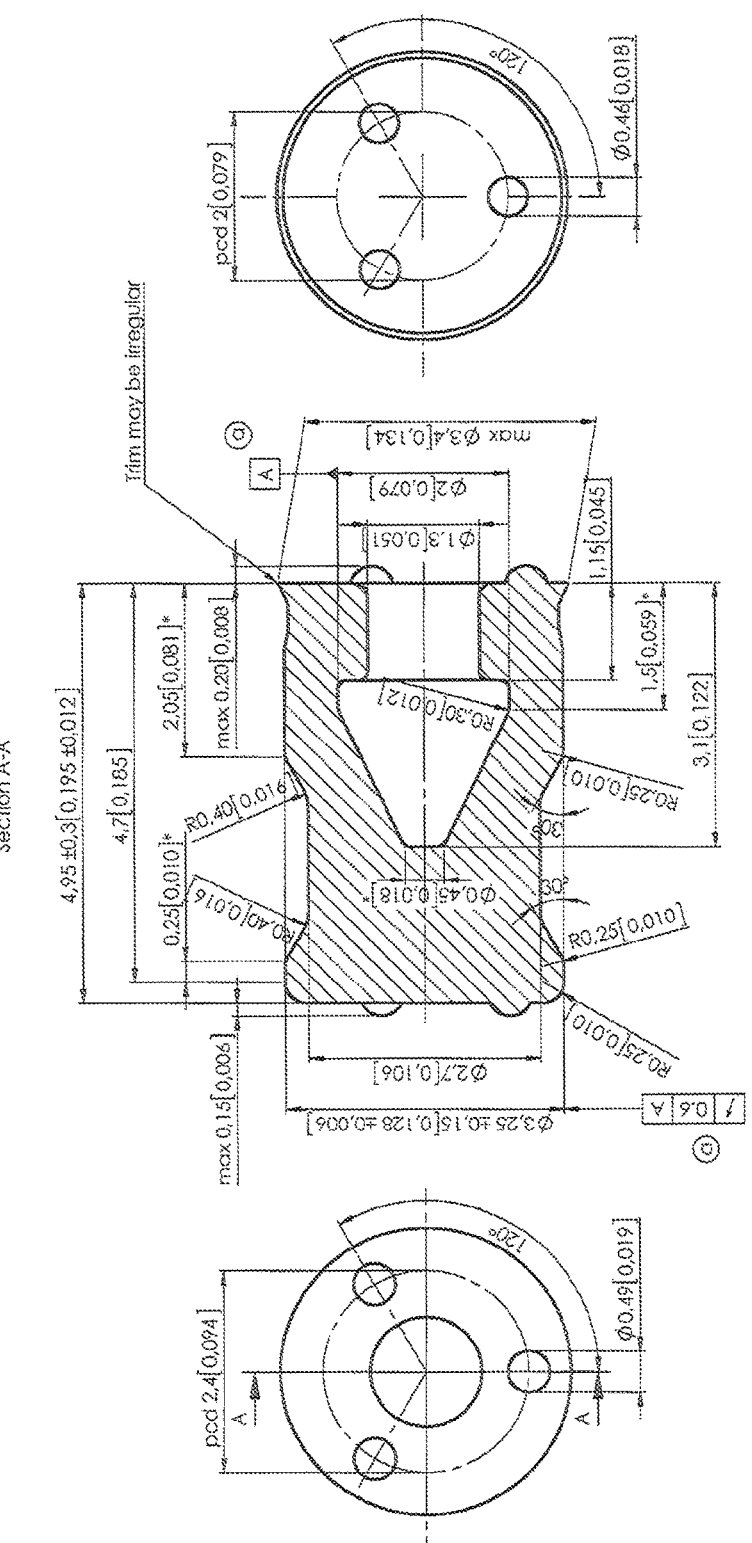
Figure 38N:
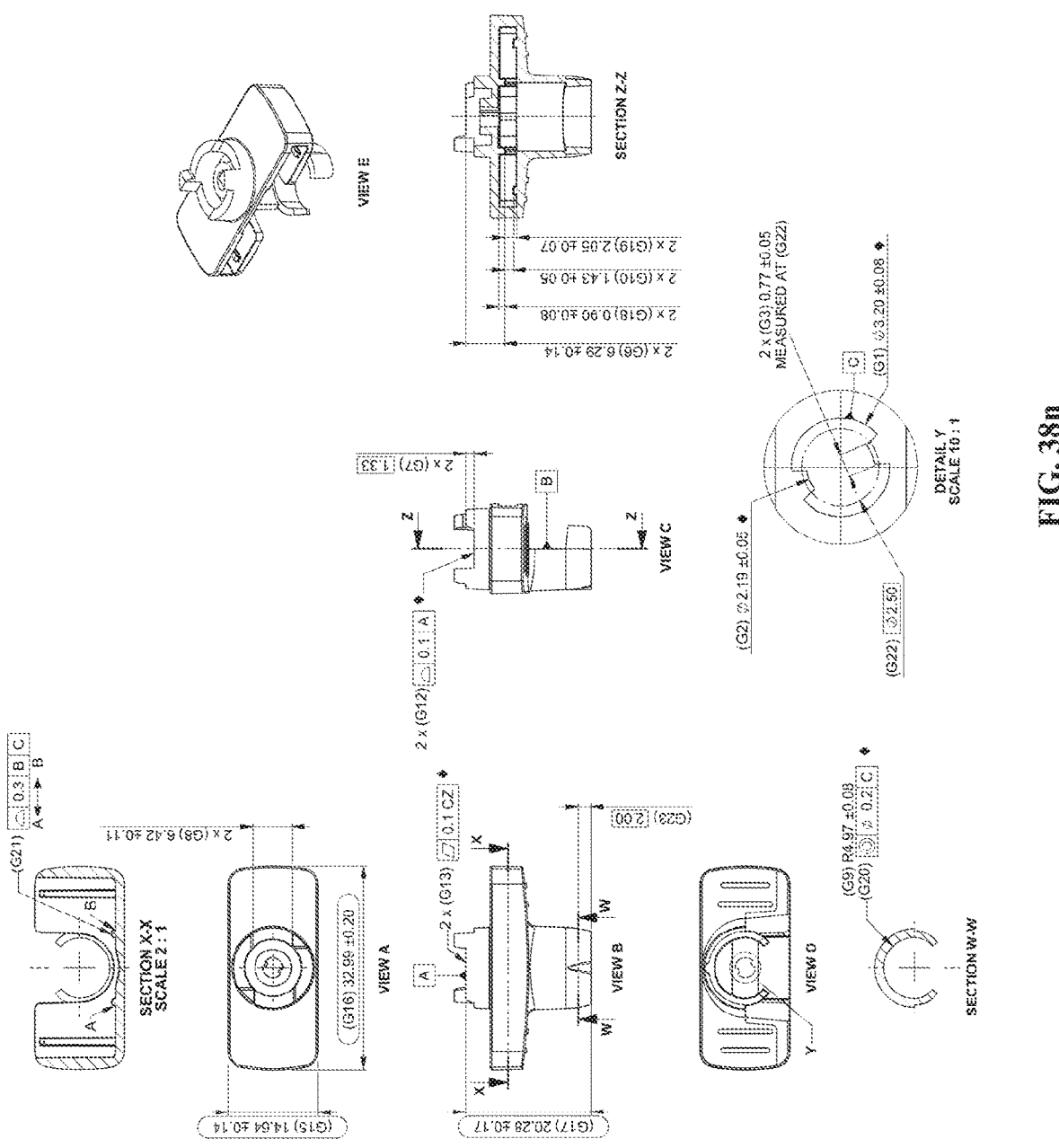
Figure 380:
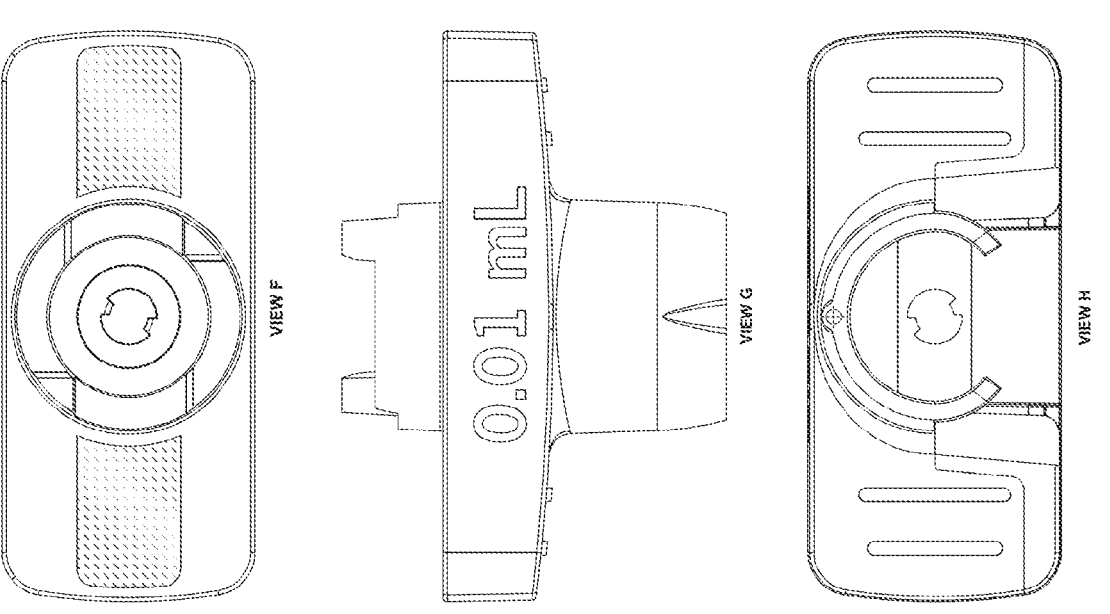
Figure 38P:
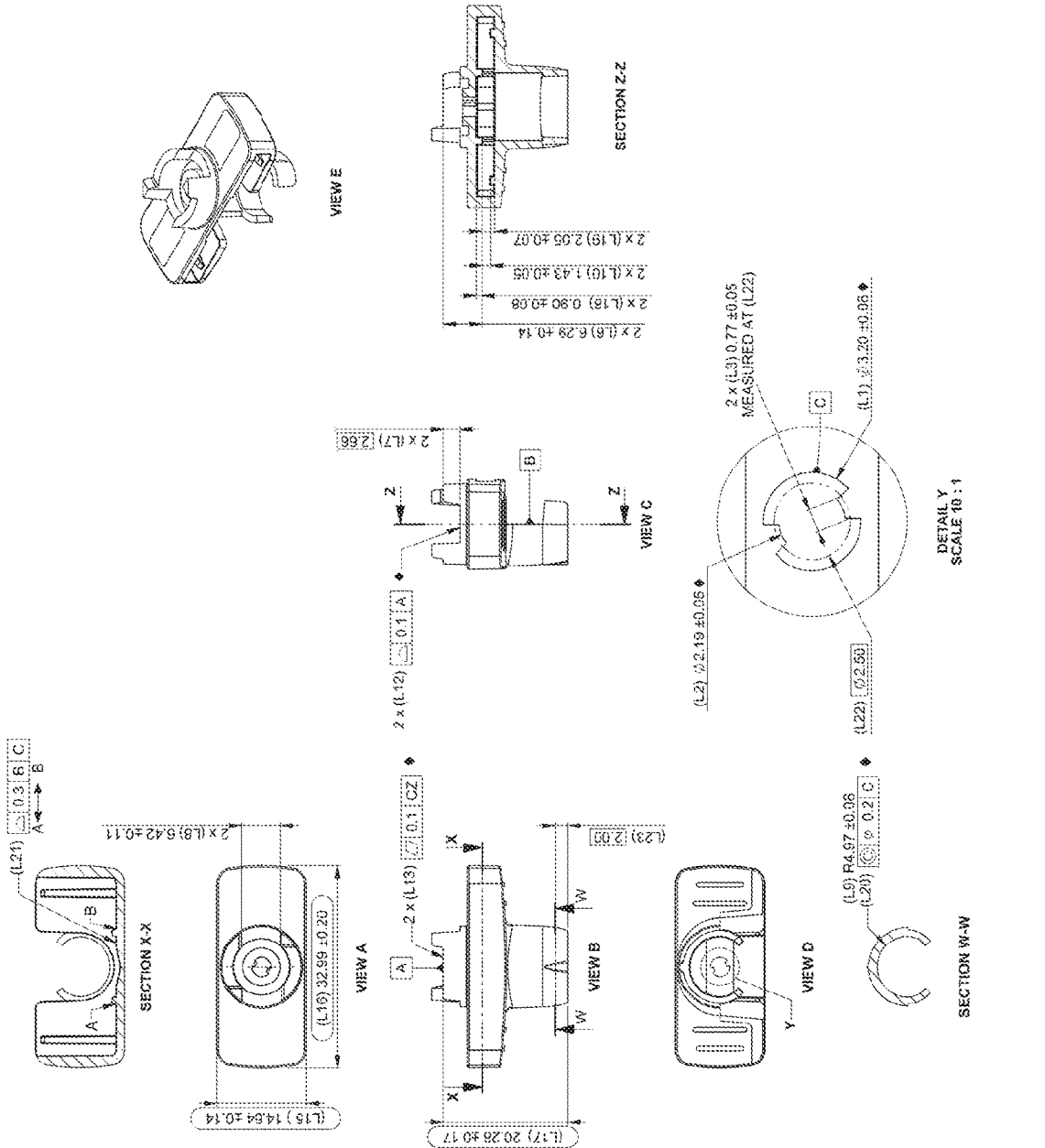
Figure 39Q:
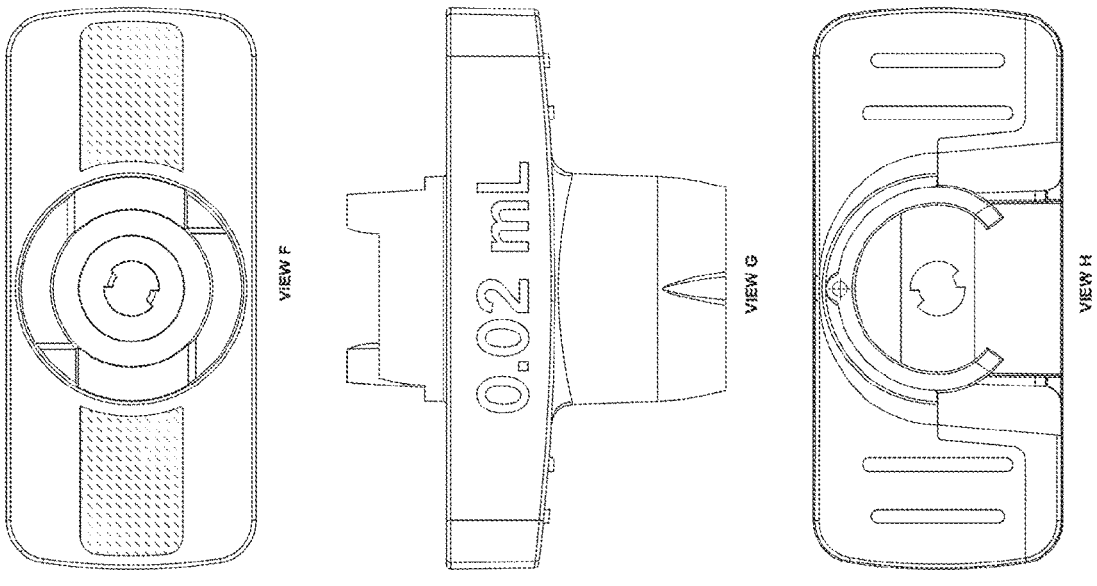

FIGS. 38*a* to 38*s* show additional views of an injection device (e.g., injection device 200) and its components, according to various examples.

Exemplary solution dispensing devices and methods are set out in the following items:

1. A solution dispensing device (200), comprising:
   a rotatable plunger (204);
   a solution receptacle (202) having a first end configured to slidably receive the rotatable plunger and a second end configured to dispense solution contained in the solution receptacle, wherein the solution dispensing device is configured to:
   allow the rotatable plunger, while it is in a first orientation (O1), to be slidably displaced along a first axis to be positioned at a first position (P1) relative to the solution receptacle, and
   allow the rotatable plunger, while it is in a second orientation (O2), to be slidably displaced along the first axis from the first position to a second position (P2) relative to the solution receptacle, wherein:
   the second position is closer to the second end of the solution receptacle than the first position, and
   slidably displacing the rotatable plunger from the first position to the second position dispenses a quantity of the solution contained in the solution receptacle;
   a first stop member (240) configured to prevent the rotatable plunger from being slidably displaced to the second position while the rotatable plunger is at the first position and in the first orientation; and
   a second stop member (242) configured to prevent the rotatable plunger from rotating in a first direction about the first axis while the rotatable plunger is at the first position and in the first orientation.

2. The solution dispensing device of item 1, further comprising:

a third stop member (242) configured to prevent the rotatable plunger from rotating in a second direction about the first axis while the rotatable plunger is at the first position and in the second orientation.

3. The solution dispensing device of any one of items 1-2, wherein the first stop member is positioned on the rotatable plunger.

4. The solution dispensing device of any one of items 1-3, wherein the second stop member is positioned on the rotatable plunger.

5. The solution dispensing device of any one of items 1-4, further comprising:

a housing (208) configured to releasably connect to the solution receptacle, wherein the housing includes a plunger through-hole (236) that is configured to slidably receive the rotatable plunger and to allow the solution receptacle to slidably receive the rotatable plunger.

6. The solution dispensing device of item 5, wherein the first stop member is positioned on a top surface of the housing, and wherein the first stop member projects from the top surface of the housing in a proximal direction along the first axis.

7. The solution dispensing device of any one of items 5-6, wherein the second stop member is positioned on the top surface of the housing, and wherein the second stop member projects from the top surface of the housing in the proximal direction along the first axis.

8. The solution dispensing device of any one of items 5-7, wherein the first stop member has a first height relative to the top surface of the housing, and wherein the quantity of the solution that is dispensed when the rotatable plunger is slidably displaced from the first position to the second position is based at least in part on the first height.

9. The solution dispensing device of item 8, wherein the second stop member has a second height relative to the top surface of the housing that is greater than the first height.

10. The solution dispensing device of any one of items 5-9, wherein an outer surface of the solution receptacle includes a clip receiver element (220), wherein the housing includes a housing clip (234), and wherein the housing clip releasably connects to the clip receiver element.

11. The solution dispensing device of item 10, wherein the first end of the solution receptacle includes a flange element (214), and wherein the housing is configured to slidably receive the flange element when the housing clip releasably connects to the clip receiver element.

12. The solution dispensing device of any one of items 1-11, wherein the rotatable plunger includes a flange (226), wherein the flange contacts the first stop member and prevents the rotatable plunger from being slidably displaced to the second position while the rotatable plunger is at the first position and in the first orientation, and wherein the flange contacts the second stop member and prevents the rotatable plunger from rotating about the first axis in the first direction while the rotatable plunger is at the first position and in the first orientation.

13. The solution dispensing device of any one of items 1-12, wherein the solution dispensing device is configured to prevent the rotatable plunger from rotating about the first axis until the rotatable plunger is positioned at the first position.

14. The solution dispensing device of any one of items 1-13, wherein the quantity of solution dispensed when the rotatable plunger is slidably displaced from the first position to the second position is selected from the group consisting of 5 µL, 10 µL, and 20 µL.

15. The solution dispensing device of any one of items 1-14, wherein an inner surface of the solution receptacle (210) is coated with a plasma-enhanced chemical vapor deposition (PECVD) coating, and wherein the PECVD coating imparts a lubricity layer on the inner surface.

16. The solution dispensing device of any of items 1-15, wherein the inner surface of the solution receptacle is coated with a lubricant coating created from a PECVD process that uses octamethylcyclotetrasiloxane (OMCTS) as a precursor.

17. The solution dispensing device of any of items 1-16, wherein the solution receptacle is manufactured via a PECVD process that uses radiofrequency power comprised of silicon, carbon, and oxygen under at least ISO class 8 conditions while in operation and ISO class 7 conditions at rest according to ISO 14644.

18. A method for dispensing solution from a solution dispensing device (200), the solution dispensing device having a rotatable plunger (204), a solution receptacle (202), a first stop member (240), and a second stop member (242), the method comprising:

slidably inserting the rotatable plunger into a first end of the solution receptacle, wherein a second end of the solution receptacle is configured to dispense a solution contained in the solution receptacle;

while the rotatable plunger is in a first orientation (O1), slidably displacing the rotatable plunger along a first axis until the rotatable plunger is in a first position (P1) relative to the solution receptacle, wherein:

the first stop member prevents the rotatable plunger from being slidably displaced to a second position (P2) relative to the solution receptacle that is closer to the second end of the solution receptacle than the first position while the rotatable plunger is at the first position and in the first orientation, and the second stop member prevents the rotatable plunger from rotating in a first direction about the first axis while the rotatable plunger is at the first position and in the first orientation;

rotating the rotatable plunger in a second direction about the first axis until the rotatable plunger is in a second orientation (O2) at the first position; and while the rotatable plunger is in the second orientation, slidably displacing the rotatable plunger along the first axis until the rotatable plunger is in the second position relative to the solution receptacle, wherein slidably displacing the rotatable plunger from the first position to the second position dispenses a quantity of the solution contained in the solution receptacle.

19. The method of item 18, wherein a third stop member (242) prevents the rotatable plunger from rotating in the second direction about the first axis while the rotatable plunger is at the first position and in the second orientation.

20 The method of any one of items 18-19, wherein the first stop member is positioned on the rotatable plunger.

21. The method of any one of items 18-20, wherein the second stop member is positioned on the rotatable plunger.

22. The method of any one of items 18-21, wherein the solution dispensing device further includes a housing (208) configured to releasably connect to the solution receptacle, wherein the housing includes a plunger through-hole (236) that is configured to slidably receive the rotatable plunger and to allow the solution receptacle to slidably receive the rotatable plunger.

23. The method of item 22, wherein the first stop member is positioned on the housing.

24 The method of any one of items 22-23, wherein the second stop member is positioned on the housing.

25. The method of any one of items 22-24, wherein the first stop member has a first height, and wherein the quantity of the solution that is dispensed when the rotatable plunger is slidably displaced from the first position to the second position is based at least in part on the first height.

26. The method of any one of items 18-25, wherein the rotatable plunger includes a flange (226), wherein the flange contacts the first stop member and prevents the rotatable plunger from being slidably displaced to the second position while the rotatable plunger is at the first position and in the first orientation, and wherein the flange contacts the second stop member and prevents the rotatable plunger from rotating about the first axis in the first direction while the rotatable plunger is at the first position and in the first orientation.

27. The method of any one of items 18-26, wherein the solution dispensing device is configured to prevent the rotatable plunger from rotating about the first axis until the rotatable plunger is positioned at the first position.

28 The method of any one of items 18-27, wherein the quantity of solution dispensed when the rotatable plunger is slidably displaced from the first position to the second position is selected from the group consisting of 5 μL, 10 μL, and 20 μL.

29 The method of any one of items 18-28, wherein the solution receptacle contains between 100 μL to 1000 μL of the solution.

30. The method of any one of items 18-29, wherein the quantity of solution dispensed when the rotatable plunger is slidably displaced from the first position to the second position is between 2.5% and 12.5% of the solution contained in the solution receptacle.

31. The method of any one of items 18-30, wherein the solution contains a vascular endothelial growth factor (VEGF) antagonist.

32. The method of any one of items 18-31, wherein the solution contains Beovu® (brolucizumab).

33. The method of any one of items 18-32, wherein the solution contains Eylea® (aflibercept).

34. The method of any one of items 18-33, wherein the solution contains Luxturna® (Voretigene neparvovec).

35. The method of any one of items 18-34, wherein the solution contains nucleic acids.

36. The method of any one of items 18-35, wherein the method is used for a pediatric ophthalmic injection.

37. The method of any one of items 18-36, wherein the method is used for gene therapy.

What is claimed is:

1. A solution dispensing device, comprising:
a rotatable plunger;
a solution receptacle having a first end configured to slidably receive the rotatable plunger and a second end configured to dispense solution contained in the solution receptacle, wherein the solution dispensing device is configured to:
allow the rotatable plunger, while the rotatable plunger is in a first orientation, to be slidably displaced along a first axis to be positioned at a first position relative to the solution receptacle, and
allow the rotatable plunger, while the rotatable plunger is in a second orientation, to be slidably displaced along the first axis from the first position to a second position relative to the solution receptacle, wherein:
the second position is closer to the second end of the solution receptacle than the first position, and
slidably displacing the rotatable plunger from the first position to the second position in a distal direction dispenses a quantity of the solution contained in the solution receptacle;
a housing configured to releasably connect to the solution receptacle, wherein the housing includes a plunger through-hole that is configured to slidably receive the rotatable plunger and to allow the solution receptacle to slidably receive the rotatable plunger;
a first stop member configured to prevent the rotatable plunger from being slidably displaced to the second position while the rotatable plunger is at the first position and in the first orientation, wherein:
the first stop member projects from a top surface of the housing in a proximal direction away from the second end and along the first axis, wherein the top surface of the housing faces away from the second end of the solution receptacle, and
the first stop member has a first height relative to the top surface of the housing; and
a second stop member configured to prevent the rotatable plunger from rotating in a first direction about the first axis while the rotatable plunger is at the first position and in the first orientation, wherein:
the second stop member projects from the top surface of the housing in the proximal direction away from the second end and along the first axis, and
the second stop member has a second height relative to the top surface of the housing that is greater than the first height.

2. The solution dispensing device of claim 1, further comprising:
a third stop member configured to prevent the rotatable plunger from rotating in a second direction about the first axis while the rotatable plunger is at the first position and in the second orientation.

3. The solution dispensing device of claim 1, and wherein the quantity of the solution that is dispensed when the rotatable plunger is slidably displaced from the first position to the second position is based at least in part on the first height.

4. The solution dispensing device of claim 1, wherein an outer surface of the solution receptacle includes a clip receiver element,
wherein the housing includes a housing clip, and
wherein the housing clip releasably connects to the clip receiver element.

5. The solution dispensing device of claim 4, wherein the first end of the solution receptacle includes a flange element, and wherein the housing is configured to slidably receive the flange element when the housing clip releasably connects to the clip receiver element.

6. The solution dispensing device of claim 1, wherein the rotatable plunger includes a flange,
wherein the flange contacts the first stop member and prevents the rotatable plunger from being slidably displaced to the second position while the rotatable plunger is at the first position and in the first orientation, and wherein the flange contacts the second stop member and prevents the rotatable plunger from rotating about the first axis in the first direction while the rotatable plunger is at the first position and in the first orientation.

7. The solution dispensing device of claim 1, wherein the solution dispensing device is configured to prevent the rotatable plunger from rotating about the first axis until the rotatable plunger is positioned at the first position.

8. The solution dispensing device of claim 1, wherein the quantity of the solution dispensed when the rotatable plunger is slidably displaced from the first position to the second position is selected from a group consisting of 5 μL, 10 μL, and 20 μL.

9. The solution dispensing device of claim 1, wherein an inner surface of the solution receptacle is coated with a plasma-enhanced chemical vapor deposition (PECVD) coating, and wherein the PECVD coating imparts a lubricity layer on the inner surface.

10. The solution dispensing device of claim 1, wherein an inner surface of the solution receptacle is coated with a lubricant coating created from a PECVD process that uses octamethylcyclotetrasiloxane (OMCTS) as a precursor.

11. The solution dispensing device of claim 1, wherein the solution receptacle is manufactured via a PECVD process that uses radiofrequency power comprised of silicon, carbon, and oxygen under at least ISO class 8 conditions while in operation and ISO class 7 conditions at resting according to ISO 14644.

12. A method for dispensing solution from a solution dispensing device, the solution dispensing device having a rotatable plunger, a solution receptacle, a housing, a first stop member, and a second stop member, the method comprising:

slidably inserting the rotatable plunger into a first end of the solution receptacle, wherein a second end of the solution receptacle is configured to dispense the solution contained in the solution receptacle;

while the rotatable plunger is in a first orientation, slidably displacing the rotatable plunger along a first axis until the rotatable plunger is in a first position relative to the solution receptacle, wherein:

the housing is configured to releasably connect to the solution receptacle, wherein the housing includes a plunger through-hole that is configured to slidably receive the rotatable plunger and to allow the solution receptacle to slidably receive the rotatable plunger;

the first stop member prevents the rotatable plunger from being slidably displaced to a second position relative to the solution receptacle that is closer to the second end of the solution receptacle than the first position while the rotatable plunger is at the first position and in the first orientation, wherein:

the first stop member projects from a top surface of the housing in a proximal direction away from the second end and along the first axis, wherein the top surface of the housing faces away from the second end of the solution receptacle, and the first stop member has a first height relative to the top surface of the housing; and the second stop member prevents the rotatable plunger from rotating in a first direction about the first axis while the rotatable plunger is at the first position and in the first orientation, wherein:

the second stop member projects from the top surface of the housing in the proximal direction away from the second end and along the first axis, and the second stop member has a second height relative to the top surface of the housing that is greater than the first height;

rotating the rotatable plunger in a second direction about the first axis until the rotatable plunger is in a second orientation at the first position; and while the rotatable plunger is in the second orientation, slidably displacing the rotatable plunger along the first axis until the rotatable plunger is in the second position relative to the solution receptacle, wherein slidably displacing the rotatable plunger from the first position to the second position in a distal direction dispenses a quantity of the solution contained in the solution receptacle.

13. The method of claim 12, wherein a third stop member prevents the rotatable plunger from rotating in the second direction about the first axis while the rotatable plunger is at the first position and in the second orientation.

14. The method of claim 12, wherein the quantity of the solution that is dispensed when the rotatable plunger is slidably displaced from the first position to the second position is based at least in part on the first height.

15. The method of claim 12, wherein the rotatable plunger includes a flange, wherein the flange contacts the first stop member and prevents the rotatable plunger from being slidably displaced to the second position while the rotatable plunger is at the first position and in the first orientation, and wherein the flange contacts the second stop member and prevents the rotatable plunger from rotating about the first axis in the first direction while the rotatable plunger is at the first position and in the first orientation.

16. The method of claim 12, wherein the solution dispensing device is configured to prevent the rotatable plunger from rotating about the first axis until the rotatable plunger is positioned at the first position.

17. The method of claim 12, wherein the quantity of the solution dispensed when the rotatable plunger is slidably displaced from the first position to the second position is selected from a group consisting of 5 μL, 10 μL, and 20 μL.

18. The method of claim 12, wherein the solution receptacle contains between 100 μL to 1000 μL of the solution.

19. The method of claim 12, wherein the quantity of the solution dispensed when the rotatable plunger is slidably displaced from the first position to the second position is between 2.5% and 12.5% of the solution contained in the solution receptacle.

20. The method of claim 12, wherein the solution contains a vascular endothelial growth factor (VEGF) antagonist.

21. The method of claim 12, wherein the solution contains Beovu® (brolucizumab).

22. The method of claim 12, wherein the solution contains Eylea® (aflibercept).

23. The method of claim 12, wherein the solution contains Luxturna® (Voretigene neparvovec).

24. The method of claim 12, wherein the solution contains nucleic acids.

25. The method of claim 12, wherein the method is used for a pediatric ophthalmic injection.

26. The method of claim 12, wherein the method is used for gene therapy.

* * * * *